(12) United States Patent
Jamal

(10) Patent No.: US 10,695,400 B2
(45) Date of Patent: Jun. 30, 2020

(54) COMPOSITIONS AND METHODS FOR TREATING CANCERS ASSOCIATED WITH ETBR ACTIVATION

(71) Applicant: ENB Therapeutics, Inc., New York, NY (US)

(72) Inventor: Sumayah Jamal, New York, NY (US)

(73) Assignee: ENB THERAPEUTICS, INC., New York, NY (US)

(*) Notice: Subject to any disclaimer, the term of this patent is extended or adjusted under 35 U.S.C. 154(b) by 399 days.

(21) Appl. No.: 15/227,792

(22) Filed: Aug. 3, 2016

(65) Prior Publication Data
US 2017/0035836 A1     Feb. 9, 2017

Related U.S. Application Data

(60) Provisional application No. 62/200,181, filed on Aug. 3, 2015.

(51) Int. Cl.

| | | |
|---|---|---|
| A61K 38/16 | (2006.01) |
| A61K 31/506 | (2006.01) |
| A61K 31/44 | (2006.01) |
| A61K 31/437 | (2006.01) |
| A61K 38/05 | (2006.01) |
| A61K 38/12 | (2006.01) |
| A61K 31/4025 | (2006.01) |
| A61K 31/454 | (2006.01) |
| A61K 35/00 | (2006.01) |
| A61K 31/403 | (2006.01) |
| A61K 31/455 | (2006.01) |
| A61K 45/06 | (2006.01) |
| C07K 16/26 | (2006.01) |
| G01N 33/574 | (2006.01) |
| A61P 35/00 | (2006.01) |

(52) U.S. Cl.
CPC ............ *A61K 38/16* (2013.01); *A61K 31/403* (2013.01); *A61K 31/4025* (2013.01); *A61K 31/437* (2013.01); *A61K 31/44* (2013.01); *A61K 31/454* (2013.01); *A61K 31/455* (2013.01); *A61K 31/506* (2013.01); *A61K 38/05* (2013.01); *A61K 38/12* (2013.01); *A61K 45/06* (2013.01); *A61P 35/00* (2018.01); *C07K 16/26* (2013.01); *G01N 33/5743* (2013.01); *G01N 2800/52* (2013.01); *G01N 2800/7028* (2013.01)

(58) Field of Classification Search
CPC .......... A61K 45/06; A61P 35/00; A61P 35/04
See application file for complete search history.

(56) References Cited

U.S. PATENT DOCUMENTS

| | | |
|---|---|---|
| 4,522,811 A | 6/1985 | Eppstein et al. |
| 7,566,452 B1 | 7/2009 | Schneider et al. |
| 7,713,440 B2 | 5/2010 | Anderson et al. |
| 2008/0102451 A1 | 5/2008 | Lesniewski et al. |
| 2008/0305147 A1* | 12/2008 | Macdonald ......... A61K 9/0085 424/422 |
| 2009/0005394 A1 | 1/2009 | Harbeson |
| 2009/0202507 A1 | 8/2009 | Li et al. |
| 2009/0214518 A1 | 8/2009 | Buckanovich et al. |
| 2013/0216547 A1 | 8/2013 | Morton et al. |
| 2013/0309253 A1 | 11/2013 | Schneider et al. |
| 2014/0227260 A1 | 8/2014 | Zhang |
| 2014/0341916 A1 | 11/2014 | Polakis et al. |
| 2015/0190506 A1 | 7/2015 | Cheung et al. |
| 2016/0257752 A1 | 9/2016 | Kim et al. |
| 2017/0008971 A1 | 1/2017 | Dennis et al. |
| 2018/0030138 A1 | 2/2018 | Kowanetz et al. |
| 2018/0037655 A1 | 2/2018 | Hegde et al. |
| 2019/0218251 A1 | 7/2019 | Jamal |

FOREIGN PATENT DOCUMENTS

| | | |
|---|---|---|
| WO | WO-0067024 A1 | 11/2000 |
| WO | WO-0100198 A2 | 1/2001 |
| WO | WO-2014025837 A1 | 2/2014 |
| WO | WO-2016196381 A1 | 12/2016 |

(Continued)

OTHER PUBLICATIONS

Baker et al, Drug Metabolism and Disposition, 1993, vol. 21, pp. 1170-1171) (Year: 1993).*
Buckanovich et al (Nature Medicine, 2008, vol. 14, pp. 28-36). (Year: 2008).*
Duraiswamy et al (Cancer Research, 2013, vol. 73, pp. 6900-6912) (Year: 2013).*
Deeks (Drugs, 2014, vol. 74, pp. 1233-1239). (Year: 2014).*
Greish (Journal of Drug Targeting, 2007, vol. 15, pp. 457-464) (Year: 2007).*
Sharma and Allison (Science, 2015, vol. 348, pp. 56-61) (Year: 2015).*
Kim et al (BBRC, 2015, vol. 468, pp. 485-489) (Year: 2015).*
de Tayrac et al (PLOS One, 2013, vol. 8, pp. e73332, 10 pages) (Year: 2013).*

(Continued)

*Primary Examiner* — Karen A. Canella
(74) *Attorney, Agent, or Firm* — Wilson Sonsini Goodrich & Rosati

(57) ABSTRACT

The description provides compositions and methods for treating ETBR-related cancer. In certain aspects, the description provides a delivery system for the controlled, systemic release of at least one of ETBR antagonists, caspase-8 inhibitors, or a combination thereof, optionally including an ETAR antagonist, an anti-PD-1 antibody, a bRAF inhibitor, niacinamide or a combination thereof. The compositions described are useful for the treatment of certain cancers, including, e.g., breast cancer, malignant melanoma, squamous cell carcinoma, glioblastoma, as well as others. In addition, the description provides a delivery system for the controlled release of at least one of ETBR antagonists, caspase-8 inhibitors or a combination thereof, optionally including at least one of an ETAR antagonist, an anti-PD-1 antibody, a bRAF inhibitor, niacinamide, or a combination thereof, to the central nervous system that are useful for treating cancers that have spread to the brain.

8 Claims, 16 Drawing Sheets

Specification includes a Sequence Listing.

(56) References Cited

FOREIGN PATENT DOCUMENTS

| WO | WO-2017024032 A2 | 2/2017 |
|----|------------------|--------|
| WO | WO-2017151502 A1 | 9/2017 |
| WO | WO-2017165491 A1 | 9/2017 |

OTHER PUBLICATIONS

Liu et al (Molecular Cancer Research, 2011, vol. 9, pp. 1668-1685) (Year: 2011).*
Topalian et al, Cancer Cell, 2015, vol. 27, pp. 450-461 (Year: 2015).*
Rizvi et al (The Lancet Oncology, 2015, vol. 16, pp. 257-265) (Year: 2015).*
Clinical Trials.gov, NCT01375842, first posted Jun. 17, 2011. (Year: 2011).*
Clinical Trials.gov, NCT00730639 first posted Aug. 8, 2008. (Year: 2008).*
Clinical Trials.gov, NCT01295827 first posted Feb. 15, 2011, (Year: 2011).*
Clinical Trials.gov, NCT01721772, first posted Nov. 6, 2012. (Year: 2012).*
Clinical Trials.gov, NCT01024231, first posted Dec. 2, 2009. (Year: 2009).*
How Significant Can Keytruda Be for Merck? Forbes, Oct. 2014, http://www.forbes.com/sites/greatspeculations/2014/10/03/how-significant-can-keytruda-be-for-merck/.
Asundi, J.et al MAPK pathway inhibition enhances the efficacy of an anti-endothelin B receptor drug conjugate by inducing target expression in melanoma. Mol Cancer Ther 2014: 13 (6): 1599-610 (http://mct.aacrjournals.org/content/13/6/1599.full.pdf+html).
Sosman J., Immunotherapy of advanced melanoma with immune checkpoint inhibition, Up to Date literature review (http://www.uptodate.com/contents/immunotherapy-of-advanced-melanoma-with-immune-checkpoint-inhibition).
Sosman, J. Molecularly targeted therapy for metastatic melanoma, Up to Date Literature review (http://www.uptodate.com/contents/molecularly-targeted-therapy-for-metastatic-melanoma).
Sampson JH, Carter JH, Jr., Friedman AH, Seigler HF. Demographics, prognosis, and therapy in 702 patients with brain metastases from malignant melanoma. J Neurosurg 1998; 88:11. https://app.box.com/s/0cokb7hnsuy4imcb5faocznxwbjbt2j.
Fife KM, Colman MH, Stevens GN, et al. Determinants of outcome in melanoma patients with cerebral metastases. J Clin Oncol 2004; 22:1293. http://jco.ascopubs.org/content/22/7/1293.full.pdf.
Samlowski, W. et al, Management of brain metastases in melanoma, Up to Date literature review (http://www.uptodate.com/contents/management-of-brain-metastases-in-melanoma).
Saldana-Caboverde et al,Pigment Cell and Melanoma Research; 23(2): p. 160-170, Apr. 2010 http://onlinelibrary.wiley.com/doi/10.1111/j.1755-148X.2010.00678.x/full.
Jamal, S. et al, Journal of clinical investigation, 2002:110(4):443-452. https://www.jci.org/articles/view/137/pdf.
Mangahas CR, dela Cruz GV, Schneider RJ, Jamal. S. Endothelin-1 upregulates MCAM in melanocytes. J. Invest Dermatol 2004; 123:1135-1139. http://www.jidonline.org/article/S0022-202X(15)32042-X/pdf.
Cruz-Munoz, W. et al., Roles for Endothelin Receptor B and BCL2A1 in Spontaneous CNS Metastasis of Melanoma. Cancer Research 2012; 72(19):4909-19. http://cancerres.aacrjournals.org/content/canres/72/19/4909.full.pdf.
Kamino H, Tam ST. Immunoperoxidase technique modified by counterstain with azure B as a diagnostic aid in evaluating heavily pigmented melanocytic neoplasms. J Cutan Pathol 1991; 18:436-439. https://apo.box.com/s/1g26xk7vgkjrgkgdp13kjxfayi8knv8j.
Tang L, Su M, Zhang Y, Ip W, Martinka M, Huang C, Zhou Y. Endothelin-3 is produced by metastatic melanoma cells and promotes melanoma cell suivival. J Cutan Med Surg 2008; 12:64-70. https://app.box.com/s/hokilpdxgkkxi8k7u0u0phex3yzrp7b.

Jamal S. Endothelin-1 down-regulates E-cadherin in melanocytic cells by apoptosis-independent activation of caspase-8. J Am Acad Dermatol 2000; 43:703-704. https://app.box.com/s/0memmi9fe3stiz9ei7k7i1b4vg2un5zn.
Jamal S, Schneider RJ. UV-induction of keratinocyte endothelin-1 downregulates E-cadherin in melanocytes and melanoma cells, J Clin Invest 2002; 110:443-452. https://www.jci.org/articles/view/13729/pdf.
Mangahas CR, dela Cruz GV, Friedman-Jiménez G, Jamal S. Endothelin-1 induces CXCL1 and CXCL8 secretion in human melanoma cells. J Invest Dermatol 2005; 125:307-311. http://www.sciencedirect.com/science/article/pll/S0022202X15323976.
Bagnato A, Rosanò L, Spinella F, Di Castro V, Tecce R, Natali PG. Endothelin B receptor blockade inhibits dynamics of cell interactions and communications in melanoma cell progression. Cancer Res 2004; 64:1436-1443. http://cancerres.aacrjournals.org/content/64/4/1436.
Asundi J, Lacap JA, Clark S, Nannini M, Roth L, Polakis P. MAPK pathway inhibition enhances the efficacy of an anti-endothelin B receptor drug conjugate by inducing target expression in melanoma. Mol Cancer Ther 2014; 13:1599-1610. http://mct.aacrjournals.org/content/13/6/1599.
Moretti S, Pinzi C, Spallanzani A, Berti E, Chiarugi A, Mazzola S, et al. Immunohistochemical evidence of cytokine networks during progression of human melanocytic lesions. Int J Cancer 1999; 84:160-168. http://onlinelibrary.wiley.com/doi/10.1002/(SICI)1097-0215(19990420)84:2%3C160::AID-IJC12%3E3.0.CO:2-R/epdf.
Ehrenreich H. Rieckmann P, Sinowatz F, Weih KA, Arthur LO, Goebel FD, et al. Potent stimulation of monocytic endothelin-1 production by HIV-1 glycoprotein 120. J Immunol 1993; 150:4601-4609. https://apo.box.com/s/9w91qek383mskltyajds4nbznbgk8czo.
Chiriboa L, Meehan S, Osman I, Glick M, de al Cruz Gelo, Howell BS, Friedman-Jimenez G, Schneider RJ, Jamal S. Endothelin-1 in the tumor microenvironment correlates with melanoma invasion. Melanoma Research 2016; 00(00): 1-9. https://app.box.com/s/2hvdvw0nI85dmawvdcy2fmbxo9qe95nz.
Yohn JJ, Smith C, Stevens T, Hoffman TA, Morelli JG, Hurt DL, et al. Human melanoma cells express functional endothelin-1 receptors. Biochem Biophys Res Commun 1994; 201:449-457 https://app.box.com/s/k1xwm3ei7qnxvr9m2d5if3nalk0ibrxc.
Böhm M, Schiller M, Nashan D, Stadler R, Luger TA, Metze D. Diffuse melanosis arising from metastatic melanoma: pathogenetic function of elevated melanocyte peptide growth factors, J Am Acad Dermatol 2001; 44:747-754. https://app.box.com/s/yogx7dcvo0k9ovdvr8phjy4oign15wp8.
Nelson J, Bagnato A, Battistini B, Nisen P. The endothelin axis: emerging role in cancer. Nat Rev Cancer 2003; 3:110-116. https://app.box.com/s/1wfd2sslw3twv6xsb4adoywh3v85difa.
Bagnato A, Natali PG, Endothelin receptors as novel targets in tumor therapy. J Transl Med 2004; 2:16. http://translational-medicine.biomedcentral.com/articles/10.1186/1479-5876-2-16.
Imokawa G, Kobayashi T, Miyagishi M, Higashi K, Yada Y. The role of endothelin-1 in epidermal hyperpigmentation and signaling mechanisms of mitogenesis and melanogenesis. Pigment Cell Res 1997; 10:218-228.
Saldanha G, Purnell D, Fletcher A, Potter L, Gillies A, Pringle JH. High BRAF mutation frequency does not characterize all melanocytic tumor types. Int J Cancer 2004; 111:705-710. http://onlinelibrary.wiley.com/doi/10/1002/ijc.20325/epdf.
Gray-Schopfer VC, da Rocha Dias S, Marais R. The role of B-RAF in melanoma. Cancer Metastasis Rev 2005; 24:165-183. https://app.box.com/s/4c4wfhm8h0f7rbvb7p1I00dp7p8ivx15.
Ross DT, Scherf U, Eisen MB, Perou CM, Rees C, Spellman P, et al. Systematic variation in gene expression patterns in human cancer cell lines. Nat Genet 2000; 24:227-235. https://app.box.com/s/v3kwbs9gxgtxtfhn1pfko1103cw8xyjv.
Bittner M, Meltzer P, Chen Y, Jiang Y, Seftor E, Hendrix M, et al. Molecular classification of cutaneous malignant melanoma by gene expression profiling. Nature 2000; 406:536-540. https://app.box.com/s/0phjvi3gn6wa27bl42kudlyube10vcu3.
Chiriboga et al. Endothelin-1 in the tumor microenvironment correlates with melanoma invasion. Melanoma Res. Jun. 2016; 26(3):236-44 https://app.box.com/s/2hvdvw0nl85dmawvdcy2fmbxo9qe95nz.

(56) References Cited

OTHER PUBLICATIONS

Chapman et al. Improved survival with vemurafenib in melanoma with BRAF V600E mutation. New England Journal of Medicine 364(26):2507-2516 (2011).

Lahav et al. An endothelin receptor B antagonist inhibits growth and induces cell death in human melanoma cells in vitro and in vivo. PNAS USA 96(20):11496-11500 (1999).

Takahashi. Molecular-target therapy for advanced malignant melanoma. Japanese Journal of Cancer and Chemotherapy 40(1):19-25 (2013) (English Summary).

Jones et al. Understanding Immune Cells in Tertiary Lymphoid Organ Development: It Is All Starting to Come Together. Front Immunol 7:401 (2016).

PCT/US2019/025050 International Search Report and Written Opinion dated Aug. 12, 2019.

Terrades-Garcia et al. Pathogenesis of giant-cell arteritis: how targeted therapies are influencing our understanding of the mechanisms involved. Rheumatology (Oxford) 57(supp 2):ii51-ii62 (2018).

Ishikawa et al. Biochemical and pharmacological profile of a potent and selective endothelin B-receptor antagonist, BQ-788. PNAS USA 91(11):4892-4896 (1994).

Johnstrom et al. Positron emission tomography using 18F-labelled endothelin-1 reveals prevention of binding to cardiac receptors owing to tissue-specific clearance by ET B receptors in vivo. Br J Pharmacol 144(1):115-122 (2005).

Kandalaft et al. Endothelin B receptor, a new target in cancer immune therapy. Clin Cancer Res 15(14):4521-4528 (2009).

PCT/US2019/013377 International Search Report and Written Opinion dated May 8, 2019.

PCT/US2019/013377 Invitation to Pay Additional Fees dated Mar. 12, 2019.

PCT/US2019/025050 International Application Invitation to Pay Additional Fees dated Jun. 7, 2019.

U.S. Appl. No. 16/246,398 First Action Interview dated Apr. 8, 2019.

Voronin, Kimberly. Deuteriodesilylation: a mild and selective method for the site-specific incorporation of deuterium into drug candidates and pharmaceutical structures. Thesis 2012 (132 pgs).

American Cancer Society. Cancer Facts & Figures 2015. Atlanta: American Cancer Society (2015).

Bacon et al. Serodiagnosis of Lyme disease by kinetic enzyme-linked immunosorbent assay using recombinant VlsE1 or peptide antigens of Borrelia burgdorferi compared with 2-tiered testing using whole-cell lysates. J Infect Dis 187:1187-99 (2003).

Embers et al. Dominant epitopes of the C6 diagnostic peptide of Borrelia burgdorferi are largely inaccessible to antibody on the parent VlsE molecule. Clin Vaccine Immunol 14:931-6 (2007).

Howlader et al. SEER Cancer Statistics Review, 1975-2012, National Cancer Institute. Bethesda, MD. Available at http:// seer.cancer.gov/csr/1975_2012/ (http://seer.cancer.gov/csr/ (4 pgs).

Ishikawa et al. Cyclic pentapeptide endothelin antagonists with high ETA selectivity. Potency- and solubility-enhancing modifications. Journal of Medicinal Chemistry 35(11):1239-42 (1992).

Karaki et al. Novel antagonist of endothelin ETB1 and ETB2 receptors, BQ-788: effects on blood vessel and small intestine. Biochem Biophys Res Commun. 205:168-173 (1994).

Liang et al. An immunodominant conserved region within the variable domain of VlsE, the variable surface antigen of Borrelia burgdorferi. J Immunol 163:5566-5573 (1999).

Liang et al. Sensitive and specific serodiagnosis of Lyme disease by enzyme-linked immunosorbent assay with a peptide based on an immunodominant conserved region of Borrelia burgdorferi vlsE. J Clin Microbiol 37:3990-6 (1999).

Okada. BQ-788, a selective endothelin ET(B) receptor antagonist. Cardiovascular drug reviews 20(1):53-66 (Winter 2002).

PCT/US2016/45343 International Search Report and Written Opinion dated Feb. 17, 2017.

Coffman et al. Endothelin receptor-A is required for the recruitment of antitumor T cells and modulates chemotherapy induction of cancer stem cells. Cancer Biology & Therapy 14(2):184-192 (2013).

Gangadhar et al. Clinical applications of PD-1-based therapy: a focus on pembrolizumab (MK-3475) in the management of melanoma and other tumor types. Oncotargets and Therapy 2015(8):929-937 (2015).

Lahav et al. Endothelin receptor B inhibition triggers apoptosis and enhances angiogenesis in melanomas. Cancer Research, AACR Annual Meeting 2017, Washington, D.C. 64(24):8945-8953 (2004).

Medina et al. Dabrafenib in the treatment of advanced melanoma. Drugs of today 49(6):377-385 (2013).

Rosano et al. Endothelin receptor blockade inhibits molecular effectors of Kaposi's sarcoma cell invasion and tumor growth in vivo. American Journal of Pathology 163(2):753-762 (2003).

\* cited by examiner

COMPOSITIONS AND METHODS FOR TREATING CANCERS ASSOCIATED WITH ETBR ACTIVATION

CROSS-REFERENCE TO RELATED APPLICATIONS/PATENTS

This application claims priority to U.S. Provisional Application Ser. No. 62/200,181, filed on Aug. 3, 2015, entitled "COMPOSITIONS AND METHODS FOR TREATING CANCERS ASSOCIATED WITH ETBR ACTIVATION", the entire contents of which are incorporated herein by reference in its entirety and for all purposes.

INCORPORATION BY REFERENCE

The instant application contains a Sequence Listing which has been submitted electronically in ASCII format and is hereby incorporated by reference in its entirety. Said ASCII copy, created on Aug. 19, 2016, is named "1514985_101US2_Sequence_Listing_ST25.txt" and is 727 bytes in size.

BACKGROUND

1. Field of the Discovery

The present description relates to a controlled delivery therapeutic system for the treatment of cancer, a method of treating cancer, and diagnostic screening methods. In particular, presently described are compositions and methods for administering a treatment for cancer, e.g., malignant melanoma, squamous cell carcinoma, glioblastoma, and other types of cancer.

2. Background Information

It is estimated that more than 1.6 million new cases of cancer will be diagnosed in 2015.[1] In particular, the American Cancer Society estimates that 252,310 new cases of melanoma will be diagnosed in 2015.[2] Melanoma presently accounts for 9,940 deaths in the U.S. and over 65,000 deaths worldwide.[1]

Malignant melanoma is a cancerous proliferation of melanocytes, the pigment producing cells of the epidermis. Current statistics indicate that in 2015, one in 40 Caucasian Americans will develop melanoma in their lifetime.[1] It is also estimated that there will be 73,870 new cases of advanced invasive melanoma diagnosed in the U.S., which presently has only a 16.6% five-year survival rate.[3] In addition, of those with metastatic disease, greater than 40% will have brain involvement within two years, which has a median survival of only 3-4 months.[7,8]

The primary treatment approach for malignant melanoma is surgical resection, and radiation, which carries a 50% recurrence rate within a year, and potential post radiation cognitive deficits.[9] Malignant melanomas that are in excess of 0.76 mm in thickness carry a significant risk for metastasis. However, current melanoma therapies are approved only for advanced disease. For example, of the approximately 1.7 million individuals in the U.S. and Europe currently living with melanoma, only 20% or roughly 340,000 are currently candidates for treatment.[2] Many patients do not respond to either molecularly targeted therapies or new immunologic therapies.[5,6] The development of drug resistance to currently approved drugs is also common.[4]

The Endothelin B receptor (ETBR) pathway plays a significant role in the metastatic spread of melanoma and as such, serves as a potential therapeutic target. For example, RAF and MEK kinases, current melanoma drug targets, are activated by the ETBR.[10] The Endothelin B receptor is a 7 transmembrane G-protein coupled receptor (GPCR). It is expressed at low levels in normal melanocytes but is greatly upregulated during melanoma development and progression.[10] Endothelin-1 (ET-1) and Endothelin-3 (ET-3) are ligands that activate the ETBR. ET-1 activation of ETBR causes melanoma cells to proliferate, metastasize and generate their own blood supply.[17, 24]

Squamous cell carcinoma (SCC) can affect the skin, the tongue, and the esophagous. Squamous cell carcinoma is also linked to ETBR expression. For example, high levels of ETBR expression in squamous cell tumors is an indicator of a poor prognosis. Both ETBR and ETAR antagonists have demonstrated efficacy in treating SCC in preclinical studies. As such the ETBR is also a potential therapeutic target for SCC.

Despite progress in cancer therapy development, including for melanoma and SCC, a significant unmet need remains for effective treatments. However, there are currently no melanoma drugs on the market that target ETBR.

SUMMARY

The present description relates to therapeutic compositions or formulations comprising an ETBR antagonist for the treatment of cancer. In particular, formulations as described herein are useful for treating ETBR-related cancers, e.g., melanoma, metastatic melanoma, squamous cell carcinoma, glioblastoma, or a combination thereof. As described herein, ETBR antagonists as formulated herein are surprisingly advantageous for treating ETBR-related cancers.

Thus, in one aspect, the present description provides a therapeutic composition or formulation comprising an effective amount of an ETBR antagonist, and a pharmaceutically acceptable carrier. In certain embodiments, the therapeutic composition or formulation comprises an effective amount of at least one of an ETBR antagonist, a caspase-8 inhibitor or a combination thereof, and a synergistically effective amount of at least one of an ETAR antagonist, an anti-PD1 antibody, a bRAF inhibitor, niacinamide or a combination thereof, and a pharmaceutically acceptable carrier.

As such, in another aspect, the description provides a therapeutic composition or formulation comprising an effective amount of an ETBR antagonist or a caspase-8 inhibitor or a combination thereof, and a synergistic amount of at least one additional agent selected from the group consisting of an ETAR antagonist, an anti-PD1 antibody, a bRAF inhibitor, niacinamide or a combination thereof in a biocompatible delivery system, and a pharmaceutically acceptable carrier.

In any of the embodiments or aspects described herein, the anti-PD1 antibody is at least one agent selected from the group consisting of Nivolumab, pembrolizumab, pidilizumab, or any other anti-PD1 antibody known or that becomes known to one skilled in the art.

In any of the embodiments or aspects described herein, the bRAF inhibitor is at least one agent selected from the group consisting of Dabrafenib, Sorafenib, Vemurafenib, or any other bRAF inhibitor known or that becomes known to one skilled in the art.

In any of the embodiments or aspects described herein, the ETBR antagonist is at least one of BQ788, BQ-017, A192621, a deuterated or fluorinated analog thereof, or a combination thereof.

In any of the embodiments or aspects described herein, the ETAR antagonist is BQ123.

In any of the embodiments or aspects describe herein, the caspase-8 inhibitor is a peptide with a sequence of Ac-AAVALLPAVLLAALAPIETD-CHO (SEQ ID NO:1).

In any of the embodiments or aspects described herein, a dosage of the ETBR antagonist is about 0.1 µg to about 5000 µg (e.g., about 100 µg to about 4000 µg) and/or a concentration of the ETBR antagonist is about 0.01 µg/mL to about 1000 mg/mL of the composition (e.g., about 0.1 mg/mL to about 5 mg/mL).

In any of the embodiments or aspects described herein, a dosage of the ETAR antagonist is about 0.1 µg to about 5000 µg (e.g., about 100 µg to about 4000 µg) and/or a concentration of the ETAR antagonist is about 0.01 µg/mL to about 1000 mg/mL of the composition (e.g., about 0.1 mg/mL to about 5 mg/mL).

In any of the embodiments or aspects described herein, a dosage of the anti-PD1 antibody is about 0.1 µg to about 5000 µg (e.g., about 100 µg to about 4000 µg) and/or a concentration of the anti-PD1 antibody is about 0.01 µg/mL to about 1000 mg/mL of the composition (e.g., about 0.1 mg/mL to about 5 mg/mL).

In any of the embodiments or aspects described herein, a dosage of the bRAF inhibitor is about 0.1 µg to about 5000 µg (e.g., about 100 µg to about 4000 µg) and/or a concentration of the bRAF inhibitor is about 0.01 µg/mL to about 1000 mg/mL of the composition (e.g., about 0.1 mg/mL to about 5 mg/mL).

In any of the embodiments or aspects described herein, a dosage of the niacinamide is about 0.1 µg to about 5000 µg (e.g., about 100 µg to about 4000 µg) and/or a concentration of the niacinamide is about 0.01 µg/mL to about 1000 mg/mL of the composition (e.g., about 0.1 mg/mL to about 5 mg/mL).

In any of the embodiments or aspects described herein, a dosage of the caspase-8 inhibitor is about 0.1 µg to about 5000 µg (e.g., about 100 µg to about 4000 µg or about 1 µg to about 4000 µg) and/or a concentration of the caspase-8 inhibitor is about 0.01 µg/mL to about 1000 mg/mL of the composition (e.g., about 0.1 mg/mL to about 5 mg/mL).

In any of the embodiments or aspects described herein, the composition further comprises at least one excipient selected from the group consisting of LyoCell®, soybean oil, dimethyl sulfoxide (DMSO), Intravail®, Protek®, and Aegis Hydrogel™. For example, the DMSO is an about 5% to about 100% DMSO solution.

In any of the aspects or embodiments described herein, the pharmaceutically acceptable carrier is selected from the group consisting of a solid lipid nanoparticle, a liposome, and a biocompatible polymer. For example, the therapeutic composition or formulation may comprise a liposome or nanoparticle or combination thereof having an interior volume comprising an ETBR antagonist or a caspase-8 inhibitor or a combination thereof, and at least one of an ETAR antagonist, an anti-PD1 antibody, a bRAF inhibitor, niacinamide or a combination thereof. In certain embodiments, the formulation includes a liposome comprising at least one of a neutral lipid, a basic (having a net positive charge) lipid, an acidic (having a net negative charge) lipid, cholesterol, or a combination thereof. In certain additional embodiments, the liposome further comprises a polymeric component. In certain embodiments, the interior volume of the liposome is at least partially aqueous, and comprises at least one of an ETBR antagonist, a caspase-8 inhibitor or a combination thereof, and at least one of an ETAR antagonist, an anti-PD1 antibody, a bRAF inhibitor, niacinamide or a combination thereof.

In any of the aspects or embodiments described herein, the liposome is configured to effectuate the controlled release of the ETBR antagonist and/or a caspase-8 inhibitor and/or at least one of an ETAR antagonist, an anti-PD1 antibody, a bRAF inhibitor, niacinamide or a combination thereof. In certain embodiments, the liposome is configured to effectuate rapid release of the ETBR antagonist. In any of the embodiments or aspects described herein, the liposome is configured or formulated to effectuate extended release the ETBR antagonist and/or a caspase-8 inhibitor and/or at least one of an ETAR antagonist, an anti-PD1 antibody, a bRAF inhibitor, niacinamide or a combination thereof. In any of the embodiments or aspects described herein, the liposome is configured to result in both the rapid and extended release of at least one of an ETBR antagonist, caspase-8 inhibitor or a combination thereof, and at least one of an ETAR antagonist, an anti-PD1 antibody, a bRAF inhibitor, niacinamide or a combination thereof.

In any of the embodiments or aspects described herein, the description provides a therapeutic composition or formulation comprising a hydrogel including a biocompatible polymer and an effective amount of an ETBR antagonist.

In any of the aspects or embodiments described herein, the therapeutic composition or formulation comprises at least one of an effective amount of a RAF kinase antagonist, a MEK antagonist or a combination thereof.

In any of the aspects or embodiments described herein, the therapeutic composition or formulation comprises an effective amount of at least one additional anti-cancer or chemotherapeutic agent.

In a further aspect, a controlled release subcutaneous or intramuscular dosage formulation is provided. The formulation comprises a uniform dispersion of active ingredients including: an ETBR antagonist or a caspase-8 inhibitor or a combination thereof; and a synergistic amount at least one additional agent selected from the group consisting of an ETAR antagonist, an anti-PD1 antibody, a bRAF inhibitor, niacinamide or a combination thereof in a biocompatible delivery system, wherein following administration the ETBR antagonist and additional agent are released slowly and simultaneously from the formulation into the systemic circulation.

In any of the aspects or embodiments described herein, at least one of: (1) the anti-PD1 antibody is at least one agent selected from the group consisting of Nivolumab, pembrolizumab, pidilizumab, or any other anti-PD1 antibody known or that becomes known to one skilled in the art; (2) the bRAF inhibitor is at least one agent selected from the group consisting of Dabrafenib, Sorafenib, Vemurafenib, or any other bRAF inhibitor known or that becomes known to one skilled in the art; (3) the ETBR antagonist is at least one of BQ788, BQ-017, A192621, a deuterated or fluorinated analog thereof, or a combination thereof; (4) the ETAR antagonist is BQ123; or (5) the caspase-8 inhibitor is a peptide with a sequence of Ac-AAVALLPAVLLAALAPIETD-CHO (SEQ ID NO:1).

In any of the aspects or embodiments described herein, the delivery system is selected from the groups consisting of: (1) a biocompatible polymer, (2) a liposome preparation; (3) a DMSO solution, (4) LyoCell®, and (5) a solid lipid nanoparticle preparation.

In any of the aspects or embodiments described herein, the biocaompatible polymer is selected from the group consisting of poly(lactides), poly(glycolides), poly(lactideco-glycolides), poly(lactic acid)s, poly(glycolic acid)s, poly (lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof.

In any of the aspects or embodiments described herein, the liposome preparation is selected from the group consisting of phosphatidylethanolamines (PE) such as dipalmitoyl PE (DPPE), and partially unsaturated phosphatidylcholine (PC), such as egg PC (EPC) or SPC, fully unsaturated PC such as HSPC, PG, phosphatidylserine (PS) and phosphatidylinositol (PI), a partially unsaturated PG, Dipalmitoylphosphatidylglycerol (DPPG), cholesterol, DSPE-PEG2000.

In any of the aspects or embodiments described herein, the solid lipid nanoparticle preparation is selected from the group consisting of triglycerides (Compritol 888 ATO and Dynasan 112), carnauba wax, beeswax, cetyl alcohol, emulsifying wax, cholesterol, cholesterol butyrate and poly(ethylene)glycol (PEG) derivatives.

In any of the aspects or embodiments described herein, the DMSO solution is about 5% to about 100% DMSO.

In still another aspect, the description provides methods for treating or ameliorating a disease, disorder or symptom thereof in a subject or a patient, e.g., an animal such as a human, comprising administering to a subject in need thereof an effective amount, e.g., a therapeutically effective amount, of a therapeutic composition or formulation as described herein, wherein the composition is effective for treating or ameliorating the disease or disorder or symptom thereof in the subject. In certain embodiments, the disease or disorder is an ETBR-related cancer. In still additional embodiments, the ETBR-related cancer is at least one of breast cancer, melanoma, squamous cell carcinoma or a combination thereof.

In any of the aspects or embodiments described herein, a dosage of at least one of the ETBR antagonist, the ETAR antagonist, the anti-PD1 antibody, the bRAF inhibitor, the niacinamide, and the caspase-8 inhibitor is about 100 µg to about 4000 µg at a concentration of at least one of the ETBR antagonist, the ETAR antagonist, the anti-PD1 antibody, the bRAF inhibitor, the niacinamide, and the caspase-8 inhibitor is about 0.1 to about 5.0 mg/mL of the composition.

In any of the aspects or embodiments described herein, a dosage of at least one of the ETBR antagonist, the ETAR antagonist, the anti-PD1 antibody, the bRAF inhibitor, the niacinamide, and the caspase-8 inhibitor is about 0.1 µg to about 5000 µg at a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the aspects or embodiments described herein, a dosage of at least one of the ETBR antagonist, the ETAR antagonist, the anti-PD1 antibody, the bRAF inhibitor, the niacinamide, and the caspase-8 inhibitor is about 0.1 µg to about 5000 µg.

In any of the aspects or embodiments described herein, a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the aspects or embodiments described herein, the formulation further comprises an excipient selected from the group consisting of Intravail®, Protek®, and Aegis Hydrogel™.

In a further aspect, a method for treating cancer in a patient is provided. The method comprises administering to a patient in need thereof the composition or formulation of the present disclosure.

In any of the aspects or embodiments described herein, the composition or formulation is delivered intranasally or intravenously or intracranially.

In an aspect, a method of determining sensitivity of cancer cells to an endothelin receptor antagonist is provided. The method comprises: method of determining sensitivity of cancer cells to an endothelin receptor antagonist, the method comprising: a) providing a cancer tissue sample from a patient; b) incubating the tissue sample in the presence of an antibody that binds specifically to ET-1 and/or an antibody that binds specifically to ET-3; and c) detecting the amount of antibody bound to ET-1 and/or ET-3, wherein when ET-1 and/or ET-3 are actively expressed in the cancer, the cancer will be sensitive to an endothelin receptor antagonist therapy.

In any of the aspects or embodiments described herein, following c) detecting, the method further comprises d) administering an effective amount of an endothelin receptor antagonist or an inhibitor of ETBR signaling (such as a caspase-8 inhibitor), e.g., when the cancer is sensitive to an endothelin receptor antagonist therapy or an inhibitor of ETBR signaling.

In any of the aspects or embodiments described herein, detecting the amount of antibody bound to ET-1 and/or ET-3 is performed with a secondary antibody conjugated to a detectable label.

In any of the aspects or embodiments described herein, the endothelin receptor antagonist is a selective ETBR antagonist and/or a selective ETAR antagonist, for example, BQ788 and/or BQ123. In any of the aspects or embodiments described herein, the endothelin receptor agonist is BQ788, BQ-017, a deuterated or fluorinated analog of BQ788, a deuterated or fluorinated analog of BQ-017, and/or BQ123.

In another aspect, the description provides a method for diagnosing an ETBR-related cancer in an individual comprising: a) obtaining a biological sample from a subject; b) contacting the sample with an agent capable of detecting ET-1 nucleic acid or polypeptide (e.g., nucleic acid-based probe, or antibody or fragment thereof) and/or an agent capable of detecting ET-3 nucleic acid or polypeptide (e.g., nucleic acid-based probe, or antibody or fragment thereof); c) detecting binding of the agent to ET-1 and/or ET-3 in the sample; and d) comparing the amount of agent bound to ET-1 and/or ET-3 from the subject with a control, wherein increased ET-1 and/or ET-3 is indicative of a subject with an ETBR-related cancer, and thereby diagnosing a subject as having an ETBR-related cancer.

In additional aspects, the description provides methods of selecting an appropriate therapeutic treatment for a subject having an ETBR-related cancer including the steps of: a) obtaining a biological sample from a subject; b) contacting the sample with an agent capable of detecting ET-1 nucleic acid or polypeptide (e.g., nucleic acid-based probe, or antibody or fragment thereof) and/or an agent capable of detecting ET-3 nucleic acid or polypeptide (e.g., nucleic acid-based probe, or antibody or fragment thereof); c) detecting binding of the agent to ET-1 and/or ET-3 in the sample; d) comparing the amount of agent bound to ET-1 from the subject with a control, wherein increased ET-1 and/or ET-3 is indicative of a subject with an ETBR-related cancer, and thereby diagnosing a subject as having an ETBR-related cancer; and e) administering a therapeutic composition as described herein. In certain embodiments, the method includes the step of repeating steps a)-d) thereby determining whether the subject is responding to the treatment.

In additional aspects, the description provides methods of monitoring a therapeutic treatment response in a subject having an ETBR-related cancer including the steps of: a) providing a subject diagnosed with having an ETBR-related cancer; b) administering a therapeutic for the treatment of the cancer; c) obtaining a sample from the subject after therapeutic treatment; d) contacting the sample with an agent capable of detecting ET-1 nucleic acid or polypeptide and/or an agent capable of detecting ET-3 nucleic acid or polypeptide; e) detecting binding of the agent to ET-1 and/or ET-3 in the sample; and f) comparing the amount of agent bound to ET-1 and/or ET-3 from the subject with a control thereby evaluating the therapeutic treatment response, wherein an elevated level of ET-1 and/or ET-3 is indicative of little or no therapeutic response, and reduced level of ET-1 and/or ET-3 is indicative of a positive therapeutic response.

In any of the aspects or embodiments described herein, the diagnostic methods comprise the additional step of administering a therapeutic. In certain embodiments, the same amount of therapeutic is administered. In additional embodiments, a higher dose is administered. In still additional embodiments, the methods include the step of altering the therapeutic treatment and/or regimen. In certain embodiments, the same amount of therapeutic is administered. In additional embodiments, a higher dose is administered. In still additional embodiments, the methods include the step of altering the therapeutic treatment and/or regimen. In certain embodiments, the ETBR-related cancer is at least one of breast cancer, melanoma, squamous cell carcinoma, glioblastoma or a combination thereof.

In a further aspect, a method for treating ETBR-related metastatic brain cancer is provided. The method comprises administering an effective amount to a subject in need thereof the composition or formulation of the present disclosure, wherein the composition or formulation is effective for treating or ameliorating a symptom of ETBR-related metastatic brain cancer.

In any of the aspects or embodiments described herein, the ETBR-related metastatic brain cancer is metastatic melanoma-related brain cancer, metastatic squamous cell carcinoma-related brain cancer, glioblastoma or a combination thereof.

In an aspect, a method of determining sensitivity of cancer cells to an immune based therapy is provided. The method comprises: a) providing a tissue sample from cancer cells from a patient that has a cancer; b) incubating the tissue sample in the presence of an antibody that binds ET-1 and/or an antibody that binds ET-3; and c) detecting the amount of antibody bound to ET-1 and/or ET-3, wherein when ET-1 and/or ET-3 are actively expressed in the tumor and thus indicating that the cancer will not be responsive to the immune based therapy.

In any of the aspects or embodiments described herein, detecting the amount of antibody bound to ET-1 and/or ET-3 is performed with at least one secondary antibody conjugated to a detectable label.

In any of the aspects or embodiments described herein, following c) detecting, the method further comprises d) administering an effective amount of an immune based therapy, e.g., when the cancer is responsive to the immune based therapy.

In any of the aspects or embodiments described herein, the immune based therapy is selected from the group consisting of an immune checkpoint inhibitor, a cancer vaccine, and a Chimeric Antigen Receptor T-Cell (CAR-T) therapy.

In any of the aspects or embodiments described herein, the immune checkpoint inhibitor is an anti-PD-1 antibody.

The preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
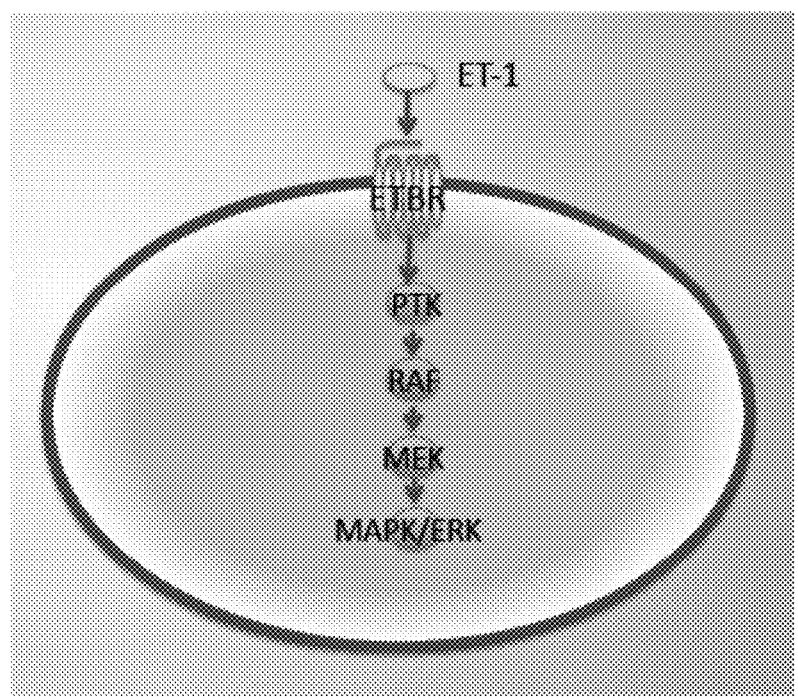
FIG. 1. Endothelin B receptor (ETBR) cell signal pathway. ETBR is a seven transmembrane G-protein coupled receptor (GPCR). Endothelin-1 (ET-1) is the ligand for the ETBR. Binding of ET-1 to the receptor results in the activation of a number of downstream kinases, including PTK, RAF, MEK, MAPK/ERK.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Presently described are compositions and methods that relate to the surprising discovery of agents useful for the treatment of cancer. In particular, formulations as described herein are useful for treating ETBR-related cancers, e.g., melanoma, metastatic melanoma, squamous cell carcinoma, glioblastoma, or a combination thereof. As described herein, ETBR antagonists as formulated herein are surprisingly advantageous for treating ETBR-related cancers.

The description provides therapeutic compositions and methods for co-administration (in a single dosage form or separate dosage forms administered approximately contemporaneously) of at least one of an ETBR antagonist, a caspase-8 inhibitor or a combination thereof, with at least one of an ETAR antagonist, an anti-PD1 antibody, a bRAF inhibitor, niacinamide or a combination thereof.

It was also surprisingly discovered that compositions comprising an effective amount of at least one of an ETBR antagonist, a caspase-8 inhibitor or a combination thereof, in combination with an effective amount (e.g., a synergistically effective amount) of an ETAR antagonist act synergistically to enhance the beneficial effects of an ETBR antagonist while minimizing adverse events or side effects. It was also surprising that an effective amount (e.g., a synergistically effective amount) of niacinamide was effective at synergistically minimizing adverse events or side effects, such as weight loss, from the ETBR antagonist. The formulations as described herein are useful for the treatment of cancer in a patient, for example, melanoma, SCC, glioblastoma, or both.

Furthermore, it was surprisingly discovered that compositions comprising an effective amount of at least one of an ETBR antagonist, a caspase-8 inhibitor or a combination thereof, in combination with an effective amount (e.g., a synergistically effective amount) of an anti-PD1 antibody act synergistically to enhance the beneficial effects of an ETBR antagonist, while minimizing adverse events or side effects. The formulations as described herein are useful for the treatment of cancer in a patient, for example, melanoma, SCC, glioblastoma, or both.

Additionally, it was surprisingly discovered that compositions comprising an effective amount of at least one of an ETBR antagonist, a caspase-8 inhibitor or a combination thereof, in combination with an effective amount (e.g., a synergistically effective amount) of a bRAF inhibitor act synergistically to enhance the beneficial effects of an ETBR antagonist. The formulations as described herein are useful for the treatment of cancer in a patient, for example, melanoma, SCC, glioblastoma, or both.

Furthermore, it was surprisingly discovered that compositions comprising an effective amount of an ETBR antagonist in combination with an effective amount (e.g., a synergistically effective amount) of a caspase-8 inhibitor act synergistically to enhance the beneficial effects of an ETBR antagonist. The formulations as described herein are useful for the treatment of cancer in a patient, for example, melanoma, SCC, glioblastoma, or both.

The preferred compositions and/or formulations as described herein demonstrate a synergistic effect in that the compositions and/or formulations achieve at least one of: a greater therapeutic effect (i.e., more efficacious) than the additive therapeutic effect obtained by administration of the constituent ingredients alone, a greater therapeutic effect than achieved by administration of a higher dose of the constituent ingredients alone, a similar or greater therapeutic effect but with a decrease in adverse events or side effects relative to that observed by administration of the constituent ingredients alone (i.e., improved therapeutic window), or a similar or greater therapeutic effect at a smaller dose of one or both of the constituent ingredients or a combination thereof.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anti-cancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "patient" or "subject" is used throughout the specification to describe an animal, preferably a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

The term "effective" is used to describe an amount of a compound, composition or component which, when used within the context of its intended use, effects an intended result. The term "effective" subsumes all other effective amount or effective concentration terms, which are otherwise described or used in the present application.

The Endothelin B receptor (ETBR) pathway (FIG. 1) plays a significant role in the metastatic spread of melanoma, and therefore, is a target for therapeutic intervention. The Endothelin B receptor is a 7 transmembrane G-protein coupled receptor (GPCR). It is expressed at very low levels in normal melanocytes, but is upregulated during melanoma development and progression.[10] RAF and MEK kinases, current melanoma drug targets, are activated by the ETBR.[10]

Figure 2:
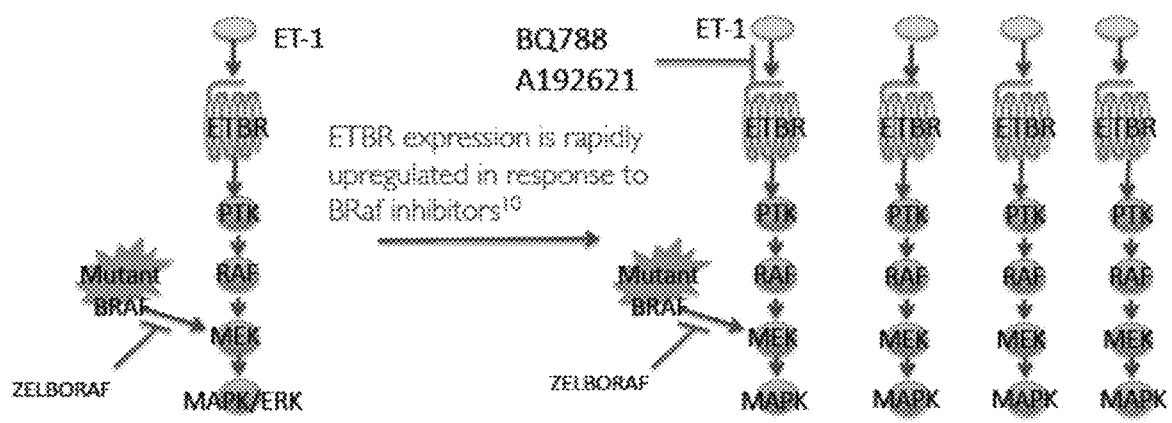
FIG. 2. Drug resistance to bRAF inhibitors is due to ETBR upregulation. Upregulation of ETBR allows melanoma cells to bypass the block to MAPK/ERK activation. ETBR antagonists, e.g., BQ788, A192621, block ET-1 binding.
Figure 3:
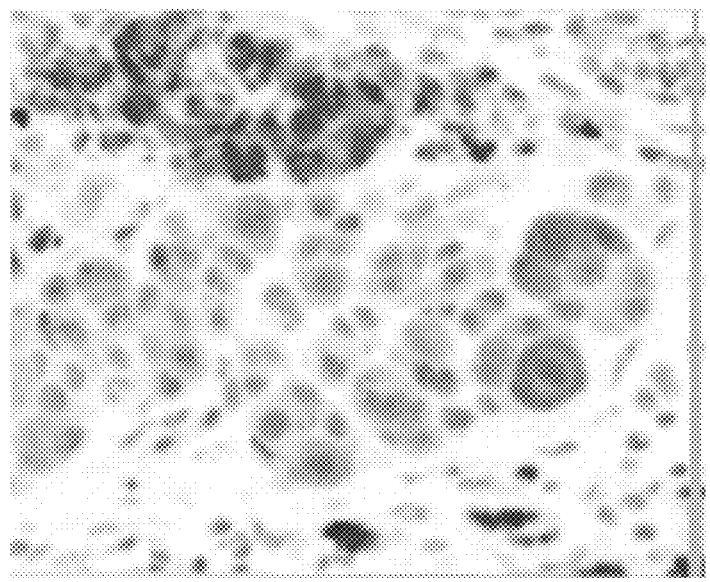
FIG. 3. ET-1 is expressed by advanced melanomas. ET-1 is the ligand that activates the ETBR, which causes melanoma cells to proliferate, metastasize, and generate their own blood supply. The tissue section is from a human invasive melanoma specimen stained with an ET-1 specific label. The photograph indicates that the melanoma is positive for ET-1. Invasive and metastatic melanomas produce ET-1.

Endothelin-1 (ET-1) (and Endothelin-3, not shown) is a ligand that activates the ETBR (FIG. 2). ET-1 activation of ETBR causes melanoma cells to proliferate, metastasize and generate their own blood supply.[17] Our studies show that the majority of pigmented invasive melanomas and metastatic melanomas produce ET-1 (FIG. 3).

Compositions

The formulations as described herein are useful for the treatment of ETBR-related cancer in a patient. In certain embodiments, the cancer is at least one of breast cancer, melanoma, SCC, glioblastoma, or a combination thereof.

In one aspect, the present description provides a therapeutic composition or formulation comprising an effective amount of an ETBR antagonist, and a pharmaceutically acceptable carrier.

In certain embodiments, the therapeutic composition or formulation comprises an effective amount of at least one of an ETBR antagonist, a caspase-8 inhibitor or a combination thereof, and an effective amount (e.g., a synergistically effective amount) of at least one of an additional anti-cancer agent, and a pharmaceutically acceptable carrier. In certain additional embodiments, the additional anti-cancer agent is selected from the group consisting of an ETAR antagonist, an anti-PD1 antibody, a bRAF inhibitor, niacinamide or a combination thereof.

In certain embodiments, the therapeutic composition or formulation comprises an effective amount (e.g., a synergistically effective amount) of at least two of an ETBR antagonist, a caspase-8 inhibitor, an ETAR antagonist, an anti-PD1 antibody, a bRAF inhibitor, niacinamide or a combination thereof.

In certain embodiments, the ETBR antagonist is selected from the group consisting of BQ788, BQ-017, A192621, and a combination thereof, including analogs, derivatives, polymorphs, prodrugs, and salts thereof, including deuterated and fluorinated analogues. For example, the ETBR antagonist can be a deuterated or fluorinated analog of BQ788 or a deuterated or fluorinated analog of BQ-017.

BQ788 ((2R)-2-[[(2R)-2-amino-3-(1-methoxycarbonylindol-3-yl)propanoyl]-[(2S)-2-[[(2R,6S)-2,6-dimethylpiperidine-1-carbonyl]amino]-4,4-dimethylpentanoyllamino] hexanoate or [N-cis-2,6-dimethylpiperidinocarbonyl-L-gamma-methylleucyl-D-1-methoxycarbonyltryptophanyl-D-norleucine], structure below) is an ETBR antagonist that has shown efficacy in treating malignant melanoma in pre-clinical studies (Okada, M; Nishikibe, M (Winter 2002). "BQ-788, a selective endothelin ET(B) receptor antagonist." Cardiovascular drug reviews 20 (1): 53-66, which is incorporated herein by reference). BQ788 is available commercially from, e.g., MolPort (MolPort-019-939-166)

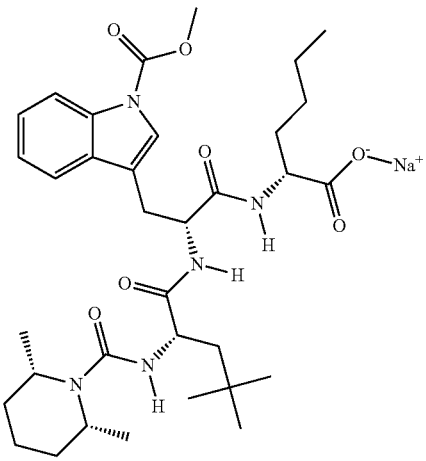

(BQ788; MW = 663 Da)

A192621 ((2R,3R,4S)-4-(1,3-benzodioxol-5-yl)-1-[2-(2,6-diethylanilino)-2-oxoethyl]-2-(4-propoxyphenyl)pyrrolidine-3-carboxylic acid or (2R-(2alpha,3beta,4alpha)-4-(1,3-benzodioxol-5-yl)-1-(2-(2,6-diethylphenyl)amino)-2-oxoethyl)-2-(4-propoxyphenyl)-3-pyrrolidinecarboxylic acid) is a potent ETBR antagonist. A192621 is available commercially from, e.g., ABI Chem (AC1NSJS8).

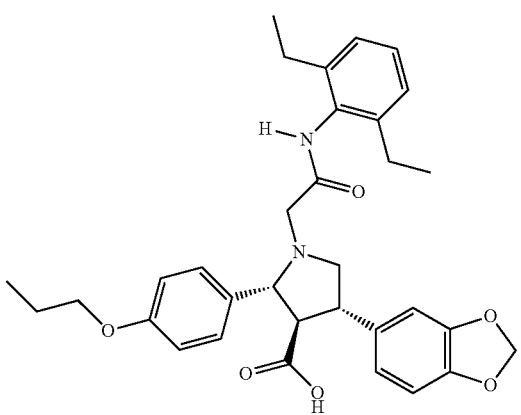

(A192621; MW = 558 Da)

However the physiologic role of the ETBR is to clear excess levels of endothelin-1 (ET-1), from the circulation. Administering BQ788 prevents ET-1 clearance and elevates serum ET-1 levels. Elevated serum levels of ET-1 are associated with a variety of adverse effects due to its activation of the Endothelin A receptor (ETAR) including, hypertension, pulmonary hypertension and renal vasoconstriction. As such, in order to minimize the unwanted effect of ETAR activation, in certain aspects, the description provides therapeutic compositions and methods for co-administration (in a single dosage form or separate dosage forms administered approximately contemporaneously) of an ETBR antagonist with an ETAR antagonist.

In certain embodiments, the ETAR antagonist is BQ123. BQ123 (2-[(3R,6R,9S,12R,15S)-6-(1H-indol-3-ylmethyl)-9-(2-methylpropyl)-2,5,8,11,14-pentaoxo-12-propan-2-yl-1,4,7,10,13-pentazabicyclo[13.3.0]octadecan-3-yl] acetic acid or cyclo(D-Trp-D-Asp-Pro-D-Val-Leu)) is a selective ETAR antagonist. (Ishikawa et al., (1992). "Cyclic pentapeptide endothelin antagonists with high ETA selectivity. Potency- and solubility-enhancing modifications." Journal of Medicinal Chemistry 35 (11): 1239-42, which is incorporated herein by reference). BQ123 is available commercially from, e.g., ABI Chem (AC1L9EDH).

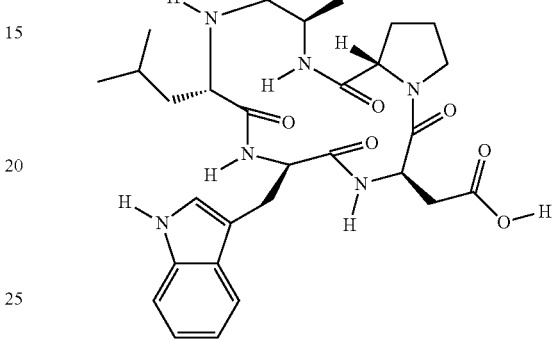

(BQ123; MW = 610 Da)

It was also surprisingly discovered that compositions comprising an effective amount of an ETBR antagonist in combination with an effective amount of an ETAR antagonist act synergistically to enhance the beneficial effects of an ETBR antagonist while minimizing adverse events or side effects. As such, in another aspect, the description provides a therapeutic composition or formulation comprising an effective amount of an ETBR antagonist in combination with an effective amount of an ETAR antagonist, and a pharmaceutically acceptable carrier. In certain embodiments, the effective amount of an ETAR is a synergistically effective amount. In certain embodiments, the ETBR antagonist is selected from the group consisting of BQ788, A192621, and a combination thereof, including analogs, derivatives, polymorphs, prodrugs, and salts thereof.

In certain embodiments, the ETAR antagonist is BQ123, including analogs, derivatives, polymorphs, prodrugs, and salts thereof.

Caspase-8 is a downstream effector of the ETBR. Caspase-8 inhibitors block molecular events that promote invasion and metastasis that are triggered as a result of ETBR activation. As such, caspase-8 inhibitors can be classified as a caspase-8 antagonist or an antagonist/inhibitor of ETBR signaling. In any of the aspects or embodiments described herein, the caspase-8 inhibitor peptide with a sequence of Ac-AAVALLPAVLLAALAPIETD-CHO (SEQ ID NO:1), which is commercially available from EMD Millipore (Billerica, Mass. 01821, USA).

In any of the aspects or embodiments described herein, the therapeutic composition or formulation comprises at least one additional anti-cancer agent. In any of the aspects or embodiments described herein, the additional anti-cancer agent is another ETBR antagonist.

In certain embodiments, the therapeutic composition or formulation comprises an effective amount of an ETBR antagonist or a caspase-8 inhibitor or a combination thereof, and an effective amount of at least one of an additional ETBR antagonist, an ETAR antagonist or a combination thereof, and a pharmaceutically acceptable carrier. In certain embodiments, the composition comprises a synergistically effective amount of at least one of an additional ETBR antagonist, an ETAR antagonist or combination thereof. In particular embodiments, the therapeutic composition or formulation further comprises an effective amount (e.g., a synergistically effective amount) of at least one of an additional ETBR antagonist, an ETAR antagonist, a bRAF inhibitor, niacinamide or a combination thereof.

In a further aspect, the description provides a therapeutic composition or formulation comprising an effective amount of at least one of an ETBR antagonist, a caspase-8 inhibitor or a combination thereof, in combination with an effective amount of an anti-PD1 antibody, and a pharmaceutically acceptable carrier. In certain embodiments, the effective amount of an anti-PD1 antibody is a synergistically effective amount. In particular embodiments, the therapeutic composition or formulation further comprises an effective amount (e.g., a synergistically effective amount) of at least one of an additional ETBR antagonist, an ETAR antagonist, a bRAF inhibitor, niacinamide or a combination thereof.

In any of the aspects or embodiments described herein, the anti-PD1 antibody is at least one agent selected from the group consisting of Nivolumab, pembrolizumab, pidilizumab, or any other anti-PD1 antibody known or that becomes known to one skilled in the art.

In yet another aspect, the description provides a therapeutic composition or formulation comprising an effective amount of at least one of an ETBR antagonist, a caspase-8 inhibitor or a combination thereof, in combination with an effective amount of a bRAF inhibitor, and a pharmaceutically acceptable carrier. In certain embodiments, the effective amount of a bRAF inhibitor is a synergistically effective amount. In particular embodiments, the therapeutic composition or formulation further comprises an effective amount of at least one of an additional ETBR antagonist, an ETAR antagonist, an anti-PD1 antibody or a combination thereof.

In any of the aspects or embodiments described herein, the bRAF inhibitor is at least one agent selected from the group consisting of Dabrafenib, Sorafenib, Vemurafenib, or any other bRAF inhibitor known or that becomes known to one skilled in the art.

In any of the aspects or embodiments described herein, the therapeutic composition or formulation comprises an effective or synergistically effective amount of at least one additional anti-cancer agent.

In certain embodiments, the additional cancer agent is a RAF kinase antagonist, a MEK antagonist or a combination thereof.

In certain embodiments, the additional anti-cancer agent is selected from the group consisting of ipilimumab, vemurafenib, dacabazine, nivolumab, pembrolizumab, niacinamide, interleukin-2, DEDN6526, Talimogene laherparepvec, tumor infiltrating lymphocytes, an anti-angiogenic agent, adriamycin, camptothecin, carboplatin, cisplatin, daunorubicin, doxorubicin, alpha, beta, or gamma interferon, irinotecan, docetaxel, paclitaxel, topotecan, atrasentan, tezosentan, bosentan, sitaxsentan, enrasentan, Ro468443, TBC10950, TBC10894, A192621, A308165, SB209670, SB17242, A182086, (s)-Lu302872, J-104132, TAK-044, Sarafoxtoxin 56c, IRL2500, RES7011, Aselacins A, B, and C, Ro470203, Ro462005, sulfamethoxazole, cochinmicin I, II, and III, L749329, L571281, L754142, J104132, CGS27830, PD142893, PD143296, PD145065, PD156252, PD159020, PD160672, PD160874, TM-ET-1, IRL3630, Ro485695, L75037, LU224332, PD142893, LU302872, PD145065, Ro610612, SB217242, and combinations thereof.

In certain embodiments, the anti-angiogenic agent is selected from the group consisting of thalidomide, marimastat, COL-3, BMS275291, squalamine, 2-ME, SU6668, neovastat, Medi522, EMD121974, CAI, celecoxib, interleukin-12, IM862, TNP470, avastin, gleevac, herceptin, and combinations thereof.

In any of the aspects or embodiments described herein, the therapeutic composition or formulation comprises an effective or synergistically effective amount of niacinamide. The niacinamide can attenuate or lessen the renal vasoconstriction side-effect of the ETBR antagonists. In a particular embodiment, the therapeutic composition or formulation comprises an effective amount of an ETBR antagonist (or a caspase-8 inhibitor or an ETBR antagonist and a caspase-8 inhibitor), an effective or synergistically effective amount of an ETBR antagonist, an effective or synergistically effective amount of niacinamide, and a pharmaceutically acceptable carrier. The niacinamide can attenuate or lessen the renal vasoconstriction side-effect of the ETBR antagonists.

In any of the aspects or embodiments described herein, a dosage of at least one of the ETBR antagonist, the ETAR antagonist, the anti-PD1 antibody, the bRAF inhibitor, the niacinamide, and the caspase-8 inhibitor is about 0.1 µg to about 5000 µg. In any of the aspects or embodiments described herein, a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the embodiments or aspects described herein, a dosage of the ETBR antagonist is about 100 µg to about 4000 µg and/or a concentration of the ETBR antagonist is about 0.1 to about 5.0 mg/mL of the composition.

In any of the embodiments or aspects described herein, a dosage of the ETAR antagonist is about 100 µg to about 4000 µg and/or a concentration of the ETAR antagonist is about 0.1 to about 5.0 mg/mL of the composition.

In any of the embodiments or aspects described herein, a dosage of the anti-PD1 antibody is about 100 µg to about 4000 µg and/or a concentration of the anti-PD1 antibody is about 0.1 to about 5.0 mg/mL of the composition.

In any of the aspects or embodiments described herein, a dosage of the bRAF inhibitor is about 100 µg to about 4000 µg and/or a concentration of the bRAF inhibitor is about 0.1 to about 5.0 mg/mL of the composition.

In any of the aspects or embodiments described herein, a dosage of the niacinamide is about 100 µg to about 4000 µg and/or a concentration of the niacinamide is about 0.1 to about 5.0 mg/mL of the composition.

In any of the aspects or embodiments described herein, a dosage of the caspase-8 inhibitor is about 1.0 µg to about 4000 µg and/or a concentration of the caspase-8 inhibitor is about 0.1 to about 5.0 mg/mL of the composition.

For example, the concentration of the ETBR antagonist, the ETAR antagonist, the anti-PD1 antibody, the bRAF inhibitor, the niacinamide, and the caspase-8 inhibitor can independently be about 0.01 µg/mL to about 1000 mg/mL, about 0.01 µg/mL to about 750 mg/mL, about 0.01 µg/mL to about 500 mg/mL, about 0.01 µg/mL to about 300 mg/mL, about 0.01 µg/mL to about 150 mg/mL, about 0.01 µg/mL to about 100 mg/mL, about 0.01 µg/mL to about 50 mg/mL, about 0.01 µg/mL to about 25 mg/mL, about 0.01 µg/mL to about 10 mg/mL, about 0.01 µg/mL to about 1.0 mg/mL, about 0.01 µg/mL to about 0.1 µg/mL, about 0.1 µg/mL to about 750 mg/mL, about 0.1 µg/mL to about 500 mg/mL, about 0.1 µg/mL to about 300 mg/mL, about 0.1 µg/mL to about 150 mg/mL, about 0.1 µg/mL to about 100 mg/mL, about 0.1 µg/mL to about 50 mg/mL, about 0.1 µg/mL to about 25 mg/mL, about 0.1 µg/mL to about 10 mg/mL, about 0.1 µg/mL to about 1.0 mg/mL, about 1.0 µg/mL to about 750 mg/mL, about 1.0 µg/mL to about 500 mg/mL, about 1.0 µg/mL to about 300 mg/mL, about 1.0 µg/mL to about 150 mg/mL, about 1.0 µg/mL to about 100 mg/mL, about 1.0 µg/mL to about 50 mg/mL, about 1.0 µg/mL to about 25 mg/mL, about 1.0 µg/mL to about 10 mg/mL, about 10 µg/mL to about 750 mg/mL, about 10 µg/mL to about 500 mg/mL, about 10 µg/mL to about 300 mg/mL, about 10 µg/mL to about 150 mg/mL, about 10 µg/mL to about 100 mg/mL, about 10 µg/mL to about 50 mg/mL, about 10 µg/mL to about 25 mg/mL, about 25 µg/mL to about 750 mg/mL, about 25 µg/mL to about 500 mg/mL, about 25 µg/mL to about 300 mg/mL, about 25 µg/mL to about 150 mg/mL, about 25 µg/mL to about 100 mg/mL, about 25 µg/mL to about 50 mg/mL, about 50 µg/mL to about 750 mg/mL, about 50 µg/mL to about 500 mg/mL, about 50 µg/mL to about 300 mg/mL, about 50 µg/mL to about 150 mg/mL, about 50 µg/mL to about 100 mg/mL, about 100 µg/mL to about 750 mg/mL, about 100 µg/mL to about 500 mg/mL, about 100 µg/mL to about 300 mg/mL, about 100 µg/mL to about 150 mg/mL, about 150 µg/mL to about 750 mg/mL, about 150 µg/mL to about 500 mg/mL, about 150 µg/mL to about 300 mg/mL, about 300 µg/mL to about 750 mg/mL, about 300 µg/mL to about 500 mg/mL, or about 500 µg/mL to about 750 mg/mL of the composition For example, the dosage of the ETBR antagonist, the ETAR antagonist, the caspase-8 inhibitor, the bRAF inhibitor, niacinamide, and anti-PD1 antibody can independently be about 0.1 µg to about 5000 µg, about 0.1 µg to about 4500 µg about 0.1 µg to about 4000 µg, about 0.1 µg to about 3500 µg, about 0.1 µg to about 3000 µg, about 0.1 µg to about 2500 µg, about 0.1 µg to about 2000 µg, about 0.1 µg to about 1500 µg, about 0.1 µg to about 1000 µg, about 0.1 µg to about 500 µg, about 1.0 µg to about 5000 µg, about 1.0 µg to about 4500 µg, about 1.0 µg to about 4000 µg, about 1.0 µg to about 3500 µg, about 1.0 µg to about 3000 µg, about 1.0 µg to about 2500 µg, about 1.0 µg to about 2000 µg, about 1.0 µg to about 1500 µg, about 1.0 µg to about 1000 µg, about 1.0 µg to about 500 µg, about 100 µg to about 5000 µg, about 100 µg to about 4500 µg, about 100 µg to about 4000 µg, about 100 µg to about 3500 µg, about 100 µg to about 3000 µg, about 100 µg to about 2500 µg, about 100 µg to about 2000 µg, about 100 µg to about 1500 µg, about 100 µg to about 1000 µg, about 100 µg to about 500 µg, about 250 µg to about 5000 µg, about 250 µg to about 4500 µg, about 250 µg to about 4000 µg, about 250 µg to about 3500 µg, about 250 µg to about 3000 µg, about 250 µg to about 2500 µg, about 250 µg to about 2000 µg, about 250 µg to about 1500 µg, about 250 µg to about 1000 µg, about 250 µg to about 500 µg, about 500 µg to about 5000 µg, about 500 µg to about 4500 µg, about 500 µg to about 4000 µg, about 500 µg to about 3500 µg, about 500 µg to about 3000 µg, about 500 µg to about 2500 µg, about 500 µg to about 2000 µg, about 500 µg to about 1500 µg, about 500 µg to about 1000 µg, about 750 µg to about 5000 µg, about 750 µg to about 4500 µg, about 750 µg to about 4000 µg, about 750 µg to about 3500 µg, about 750 µg to about 3000 µg, about 750 µg to about 2500 µg, about 750 µg to about 2000 µg, about 75 µg to about 1500 µg, about 750 µg to about 1000 µg, about 1500 µg to about 5000 µg, about 1500 µg to about 4500 µg, about 1500 µg to about 4000 µg, about 1500 µg to about 3500 µg, about 1500 µg to about 3000 µg, about 1500 µg to about 2500 µg, about 1500 µg to about 2000 µg, about 2000 µg to about 5000 µg, about 2000 µg to about 4500 µg, about 2000 µg to about 4000 µg, about 2000 µg to about 3500 µg, about 2000 µg to about 3000 µg, about 2000 µg to about 2500 µg, about 2500 µg to about 5000 µg, about 2500 µg to about 4500 µg, about 2500 µg to about 4000 µg, about 2500 µg to about 3500 µg, about 2500 µg to about 3000 µg, about 3000 µg to about 5000 µg, about 3000 µg to about 4500 µg, about 3500 µg to about 4000 µg, about 3500 µg to about 5000 µg, about 3500 µg to about 4500 µg, about 3500 µg to about 4000 µg, about 4000 µg to about 5000 µg, about 4000 µg to about 4500 µg, or about 4500 µg to about 5000 µg.

In any of the embodiments or aspects described herein, a dosage of the anti-PD1 antibody is about 0.1 mg/kg to about 9.0 mg/kg. For example, the dosage of the anti-PD1 antibody is about 0.1 mg/kg to about 9.0 mg/kg, about 0.1 mg/kg to about 8.0 mg/kg, about 0.1 mg/kg to about 7.0 mg/kg, about 0.1 mg/kg to about 6.0 mg/kg, about 0.1 mg/kg to about 5.0 mg/kg, about 0.1 mg/kg to about 4.0 mg/kg, about 0.1 mg/kg to about 3.0 mg/kg, about 0.1 mg/kg to about 2.0 mg/kg, about 0.1 mg/kg to about 1.0 mg/kg, about 1.0 mg/kg to about 9.0 mg/kg, about 1.0 mg/kg to about 8.0 mg/kg, about 1.0 mg/kg to about 7.0 mg/kg, about 1.0 mg/kg to about 6.0 mg/kg, about 1.0 mg/kg to about 5.0 mg/kg, about 1.0 mg/kg to about 4.0 mg/kg, about 1.0 mg/kg to about 3.0 mg/kg, about 1.0 mg/kg to about 2.0 mg/kg, about 2.0 mg/kg to about 9.0 mg/kg, about 2.0 mg/kg to about 8.0 mg/kg, about 2.0 mg/kg to about 7.0 mg/kg, about 2.0 mg/kg to about 6.0 mg/kg, about 2.0 mg/kg to about 5.0 mg/kg, about 2.0 mg/kg to about 4.0 mg/kg, about 2.0 mg/kg to about 3.0 mg/kg, about 3.0 mg/kg to about 9.0 mg/kg, about 3.0 mg/kg to about 8.0 mg/kg, about 3.0 mg/kg to about 7.0 mg/kg, about 3.0 mg/kg to about 6.0 mg/kg, about 3.0 mg/kg to about 5.0 mg/kg, about 3.0 mg/kg to about 4.0 mg/kg, about 4.0 mg/kg to about 9.0 mg/kg, about 4.0 mg/kg to about 8.0 mg/kg, about 4.0 mg/kg to about 7.0 mg/kg, about 4.0 mg/kg to about 6.0 mg/kg, about 4.0 mg/kg to about 5.0 mg/kg, about 5.0 mg/kg to about 9.0 mg/kg, about 5.0 mg/kg to about 8.0 mg/kg, about 5.0 mg/kg to about 7.0 mg/kg, about 5.0 mg/kg to about 6.0 mg/kg, about 6.0 mg/kg to about 9.0 mg/kg, about 6.0 mg/kg to about 8.0 mg/kg, about 6.0 mg/kg to about 7.0 mg/kg, about 7.0 mg/kg to about 9.0 mg/kg, about 7.0 mg/kg to about 8.0 mg/kg, or about 8.0 mg/kg to about 9.0 mg/kg.

In any of the embodiments or aspects described herein, a dosage of the bRAF inhibitor is about 1 mg to about 1500 mg. For example, the dosage of the bRAF inhibitor about 1 mg to about 1500 mg, about 1 mg to about 1250 mg, about 1 mg to about 1000 mg, about 1 mg to about 750 mg, about 1 mg to about 500 mg, about 1 mg to about 250 mg, about 250 mg to about 1500 mg, about 250 mg to about 1250 mg, about 250 mg to about 1000 mg, about 250 mg to about 750 mg, about 250 mg to about 500 mg, about 500 mg to about 1500 mg, about 500 mg to about 1250 mg, about 500 mg to about 1000 mg, about 500 mg to about 750 mg, about 750 mg to about 1500 mg, about 750 mg to about 1250 mg, about 750 mg to about 1000 mg, about 1000 mg to about 1500 mg, about 1000 mg to about 1250 mg, or about 1250 mg to about 1500 mg.

In any of the embodiments or aspects described herein, a dosage of the niacinamide is about 1 mg to about 3000 mg. For example, the dosage of the niacinamide is about 1 mg to about 3000 mg, about 1 mg to about 2750 mg, about 1 mg to about 2500 mg, about 1 mg to about 2250 mg, about 1 mg to about 2000 mg, about 1 mg to about 1750 mg, about 1 mg to about 1500 mg, about 1 mg to about 1250 mg, about 1 mg to about 1000 mg, about 1 mg to about 750 mg, about 1 mg to about 500 mg, about 1 mg to about 250 mg, about 250 mg to about 3000 mg, about 250 mg to about 2750 mg, about 250 mg to about 2500 mg, about 250 mg to about 2250 mg, about 250 mg to about 2000 mg, about 250 mg to about 1750 mg, about 250 mg to about 1500 mg, about 250 mg to about 1250 mg, about 250 mg to about 1000 mg, about 250 mg to about 750 mg, about 250 mg to about 500 mg, about 500 mg to about 3000 mg, about 500 mg to about 2750 mg, about 500 mg to about 2500 mg, about 500 mg to about 2250 mg, about 500 mg to about 2000 mg, about 500 mg to about 1750 mg, about 500 mg to about 1500 mg, about 500 mg to about 1250 mg, about 500 mg to about 1000 mg, about 500 mg to about 750 mg, about 750 mg to about 3000 mg, about 750 mg to about 2750 mg, about 750 mg to about 2500 mg, about 750 mg to about 2250 mg, about 750 mg to about 2000 mg, about 750 mg to about 1750 mg, about 750 mg to about 1500 mg, about 750 mg to about 1250 mg, about 750 mg to about 1000 mg, about 1000 mg to about 3000 mg, about 1000 mg to about 2750 mg, about 1000 mg to about 2500 mg, about 1000 mg to about 2250 mg, about 1000 mg to about 2000 mg, about 1000 mg to about 1750 mg, about 1000 mg to about 1500 mg, about 100 mg to about 1250 mg, about 1250 mg to about 3000 mg, about 1250 mg to about 2750 mg, about 1250 mg to about 2500 mg, about 1250 mg to about 2250 mg, about 1250 mg to about 2000 mg, about 1250 mg to about 1750 mg, about 1250 mg to about 1500 mg, about 1500 mg to about 3000 mg, about 1500 mg to about 2750 mg, about 1500 mg to about 2500 mg, about 1500 mg to about 2250 mg, about 1500 mg to about 2000 mg, about 1500 mg to about 1750 mg, about 1750 mg to about 3000 mg, about 1750 mg to about 2750 mg, about 1750 mg to about 2500 mg, about 1750 mg to about 2250 mg, about 1750 mg to about 2000 mg, about 2000 mg to about 3000 mg, about 2000 mg to about 2750 mg, about 2000 mg to about 2500 mg, about 2000 mg to about 2250 mg, about 2250 mg to about 3000 mg, about 2250 mg to about 2750 mg, about 2250 mg to about 2500 mg, about 2500 mg to about 3000 mg, about 2500 mg to about 2750 mg, or about 2750 mg to about 3000 mg Based on the present description, the provided exemplary dosage ranges can be combined in order to maximize or optimize the synergistic effect observed, as discussed above, when co-administered using routine methodologies.

Pharmaceutical compositions as described herein, include combination of active compounds in combination with a pharmaceutically effective amount of a carrier, additive or excipient, represents a further aspect of the present disclosure. In a particular embodiment, the excipient selected from the group consisting of Intravail®, Protek®, and Aegis Hydrogel™. In another embodiment, the composition or formulation includes at least one excipient selected from the group consisting of LyoCell®, soybean oil, dimethyl sulfoxide (DMSO), Intravail®, Protek®, and Aegis Hydrogel™. For example, the DMSO is a DMSO solution comprising about 5% to about 100% DMSO, about 25% to about 100% DMSO, about 50% to about 100% DMSO, about 75% to about 100% DMSO, about 5% to about 75% DMSO, about 25% to about 75% DMSO, about 50% to about 75% DMSO, about 5% to about 50% DMSO, about 25% to about 50% DMSO, or about 5% to about 25% DMSO.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form nontoxic base salts with such compounds. Such nontoxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent(s) chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, dimethyl sulfoxide (DMSO), soybean oil as a carrier, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil, castor oil or soybean oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, DMSO, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques described herein relating to pharmaceutical formulation and may be prepared as solutions in saline, employing benzyl alcohol or other suitable preservatives, absorption promoters to enhance bioavailability, fluorocarbons, and/or other conventional solubilizing or dispersing agents. In certain embodiments, the description provides formulations comprising liposomes including an effective amount (e.g., a synergistically effective amount) of at least one of a ETBR antagonist or a caspase-8 inhibitor or a combination thereof, and/or an effective amount (e.g., a synergistically effective amount) of at least one of an ETAR antagonist, an anti-PD1 antibody, a bRAF inhibitor, niacinamide or a combination thereof, wherein the liposome formulation is configured or adapted for intranasal delivery or sublingual delivery. In a further embodiment, the liposomes further comprise an additional anti-cancer agent as described above.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to, one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug, as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

Solutions or suspensions used for parenteral, intradermal, subcutaneous, or topical application can include the following components: a sterile diluent such as water for injection, saline solution, fixed oils (e.g., soybean oil), polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In certain embodiments, the liposome is configured to effectuate the controlled release of the therapeutic compositions or formulations. In certain embodiments, the liposome is configured to effectuate rapid release of the therapeutic compositions or formulations. In other embodiments, the liposome is configured or formulated to effectuate extended release the therapeutic compositions or formulations. In still additional embodiments, the liposome is configured to result in both the rapid and extended release of therapeutic compositions or formulations.

In certain embodiments, the liposome is configured to effectuate the controlled release of the ETBR antagonist or the caspase-8 inhibitor or a combination thereof. In certain embodiments, the liposome is configured to effectuate rapid release of the ETBR antagonist or the caspase-8 inhibitor or a combination thereof. In other embodiments, the liposome is configured or formulated to effectuate extended release the ETBR antagonist or the caspase-8 inhibitor or a combination thereof. In still additional embodiments, the liposome is configured to result in both the rapid and extended release of the ETBR antagonist or the caspase-8 inhibitor or a combination thereof.

In additional embodiments, the description provides a controlled release subcutaneous or intramuscular dosage formulation comprising a uniform dispersion of an ETBR antagonist (e.g., B Q788, BQ-017, A192621, a deuterated or fluorinated analog thereof, or combinations thereof) and an ETAR antagonist (e.g., BQ123) in a biocompatible delivery system whereby following administration the ETBR and ETAR antagonists are released slowly and simultaneously from the formulation into the systemic circulation.

In certain embodiments, the controlled release delivery system composition comprises a biocompatible polymer. In certain embodiments, the active compounds are prepared with carriers that will protect the compound against rapid elimination from the body, such as a controlled release formulation, including implants, hydrogels, thermo-sensitive hydrogels, and microencapsulated delivery systems. Biodegradable, biocompatible polymers can be used, such as ethylene vinyl acetate, acrylates, polycarboxylic acids, polyanhydrides, polyglycolic acid, collagen, polyorthoesters, and polylactic acid.

In certain embodiments, the therapeutic composition as described herein is formulated into a controlled release delivery system comprising a biocompatible polymer selected from the group consisting of poly(lactides), poly (glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

In any of the aspects or embodiments described herein, the therapeutic composition or formulation comprises a liposome having an interior volume comprising an ETBR antagonist or a caspase-8 inhibitor or a combination thereof, and an effective amount of at least one of an ETAR antagonist, an anti-PD1 antibody, a bRAF inhibitor, niacinamide or a combination thereof. In certain embodiments, the liposome comprises at least one of a neutral lipid, a basic (having a net positive charge) lipid, an acidic (having a net negative charge) lipid, cholesterol, or a combination thereof. In certain additional embodiments, the liposome further comprises a polymeric component. In certain embodiments, the interior volume of the liposome is at least partially aqueous, and comprises an ETBR antagonist.

In certain embodiments, the description provides the therapeutic composition as described herein in a liposomal delivery system selected from the group consisting of phosphatidylethanolamines (PE) such as dipalmitoyl PE (DPPE), and partially unsaturated phosphatidylcholine (PC), such as egg PC (EPC) or SPC, Fully unsaturated PC such as HSPC, PG, phosphatidylserine (PS) and phosphatidylinositol (PI). One preferred phospholipid is a partially unsaturated PG, Dipalmitoylphosphatidylglycerol (DPPG), cholesterol, DSPE-PEG2000. In certain embodiments, the liposomal delivery system is a controlled release system, selected from the group consisting of rapid release, extended release, rapid and extended release, delayed release, and combinations thereof. In certain embodiments, the delivery system is LyoCell®.

In still additional embodiments, the therapeutic composition as described herein is formulated in a solid lipid nanoparticle preparation selected from the group consisting of triglycerides (Compritol 888 ATO and Dynasan 112), carnauba wax, beeswax, cetyl alcohol, emulsifying wax, cholesterol, cholesterol butyrate, and poly(ethylene)glycol (PEG) derivatives, and combinations thereof.

In a further aspect, the description provides a therapeutic composition or formulation comprising an effective amount of at least one of an ETBR antagonist, a caspase-8 inhibitor or a combination thereof, in combination with an effective amount of at least one of an ETAR antagonist, an anti-PD1 antibody, a bRAF inhibitor, niacinamide or a combination thereof, and a pharmaceutically acceptable carrier. In certain embodiments, the effective amount of the ETAR antagonist, the anti-PD1 antibody, the bRAF inhibitor, the niacinamide and/or a combination thereof is a synergistically effective amount. In particular embodiments, the therapeutic composition or formulation further comprises an effective amount of at least one of an additional anti-cancer agent, as described above.

In any of the aspects or embodiments described herein, the anti-PD1 antibody is at least one agent selected from the group consisting of Nivolumab, pembrolizumab, pidilizumab, or any other anti-PD1 antibody known or that becomes known to one skilled in the art.

In yet another aspect, the description provides a therapeutic composition or formulation comprising an effective amount of an ETBR antagonist or a caspase-8 inhibitor or a combination thereof, in combination with an effective amount of a bRAF inhibitor, and a pharmaceutically acceptable carrier. In certain embodiments, the effective amount of a bRAF inhibitor is a synergistically effective amount. In particular embodiments, the therapeutic composition or formulation further comprises an effective amount of at least one of an additional ETBR antagonist, an ETAR antagonist, an anti-PD-1 antibody or a combination thereof.

In any of the aspects or embodiments described herein, the bRAF inhibitor is at least one agent selected from the group consisting of Dabrafenib, Sorafenib, Vemurafenib, or any other nRAF inhibitor known or that becomes known to one skilled in the art.

In a further aspect, a controlled release subcutaneous or intramuscular dosage formulation is provided. The formulation comprises a uniform dispersion of active ingredients including: at least one of an ETBR antagonist, a caspase-8 inhibitor or a combination thereof; and a synergistic amount at least one additional agent selected from the group consisting of an ETAR antagonist, an anti-PD1 antibody, a bRAF inhibitor, niacinamide or a combination thereof in a biocompatible delivery system, wherein following administration the ETBR antagonist and additional agent are released slowly and simultaneously from the formulation into the systemic circulation.

In any of the aspects or embodiments described herein, at least one of: (1) the anti-PD1 antibody is at least one agent selected from the group consisting of Nivolumab, pembrolizumab, pidilizumab, or any other anti-PD1 antibody known or that becomes known to one skilled in the art; (2) the bRAF inhibitor is at least one agent selected from the group consisting of Dabrafenib, Sorafenib, Vemurafenib, or any other bRAF inhibitor known or that becomes known to one skilled in the art; (3) the ETBR antagonist is at least one of BQ788, BQ-017, A192621, a deuterated or fluorinated analog thereof, or a combination thereof; (4) the ETAR antagonist is BQ123; or (5) the caspase-8 inhibitor is a peptide with a sequence of Ac-AAVALLPAVLLAALAPIETD-CHO (SEQ ID NO:1).

In any of the aspects or embodiments described herein, the delivery system is selected from the groups consisting of: (1) a biocompatible polymer, (2) a liposome preparation; (3) a DMSO solution, (4) LyoCell®, and (5) a solid lipid nanoparticle preparation.

In any of the aspects or embodiments described herein, the biocaompatible polymer is selected from the group consisting of poly(lactides), poly(glycolides), poly(lactide-co-glycolides), poly(lactic acid)s, poly(glycolic acid)s, poly (lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof.

In any of the aspects or embodiments described herein, the liposome preparation is selected from the group consisting of phosphatidylethanolamines (PE) such as dipalmitoyl PE (DPPE), and partially unsaturated phosphatidylcholine (PC), such as egg PC (EPC) or SPC, Fully unsaturated PC such as HSPC, PG, phosphatidylserine (PS) and phosphatidylinositol (PI), a partially unsaturated PG, Dipalmitoyl-phosphatidylglycerol (DPPG), cholesterol, DSPE-PEG2000.

In any of the aspects or embodiments described herein, the solid lipid nanoparticle preparation is selected from the group consisting of triglycerides (Compritol 888 ATO and Dynasan 112), carnauba wax, beeswax, cetyl alcohol, emulsifying wax, cholesterol, cholesterol butyrate and poly(ethylene)glycol (PEG) derivatives.

Methods of Treatment

Activation of the ETBR by endothelins such as ET-1 and ET-3, results in a variety of molecular events that promote melanoma invasion and metastasis. While the majority of melanomas express ETBR, a subset of these also express the ETBR activator ET-1 and/or ET-3. It is this subset that is therefore most likely dependent upon ETBR activation for viability, invasive potential and metastatic potential. Thus, this subset of patients is most likely to respond to ETBR blockade. Furthermore, this subset of patents are least likely to response to immune based therapy. As such, the present disclosure concerns the use of a screening test for ET-1 and/or ET-3 expression as a companion diagnostic for the administration of an ETBR inhibitor (such as BQ788, BQ-017, A192621, a deuterated or fluorinated analog thereof, or a combination thereof) and/or a caspase-8 inhibitor and/or a ETAR inhibitor (such as BQ123).

Thus, in still another aspect, the description provides methods for treating or ameliorating a disease, disorder or symptom thereof in a subject or a patient, e.g., an animal such as a human, comprising administering to a subject in need thereof an effective amount, e.g., a therapeutically effective amount or a synergistically effective amount, of a therapeutic composition or formulation as described herein, wherein the composition is effective for treating or ameliorating the disease or disorder or symptom thereof in the subject. In certain embodiments, the disease or disorder is an ETBR-related cancer or a cancer that is insensitive to immune based therapy. In still additional embodiments, the ETBR-related cancer is at least one of breast cancer, melanoma, squamous cell carcinoma, glioblastoma or a combination thereof. In any of the aspects or embodiments described herein, the immune based therapy is selected from the group consisting of an immune checkpoint inhibitor (e.g., an anti-PD-1 antibody), a cancer vaccine, and a Chimeric Antigen Receptor T-Cell (CAR-T) therapy.

In certain embodiments, the description provides a method of inhibiting melanoma invasion and metastasis in a patient comprising administering to a subject in need thereof an effective amount, e.g., a therapeutically effective amount or a synergistically effective amount, of a therapeutic composition or formulation as described herein, wherein the composition is effective for inhibiting melanoma invasion and metastasis.

In certain embodiments, the description provides a method of inducing melanoma cell death (apoptosis) comprising administering to a subject in need thereof an effective amount, e.g., a therapeutically effective amount or a synergistically effective amount, of a therapeutic composition or formulation as described herein, wherein the composition is effective for inducing melanoma cell death.

In certain embodiments, the description provides a method of inhibiting blood supply to melanoma tumors in a patient comprising administering to a subject in need thereof an effective amount, e.g., a therapeutically effective amount or a synergistically effective amount, of a therapeutic composition or formulation as described herein, wherein the composition is effective for inhibiting blood supply to melanoma tumors.

In certain embodiments, the description provides a method of treating an ETBR-related cancer, including ETBR-related metastatic brain cancer, comprising administering intranasally to a subject in need thereof an effective amount (e.g., a therapeutically effective amount or a synergistically effective amount) of a composition or formulation described herein, including a liposomal formulation as described herein, wherein the composition or formulation is effective for treating the ETBR-related metastatic brain cancer. In certain embodiments, the ETBR-related metastatic brain cancer is a metastatic melanoma brain cancer, a metastatic squamous cell carcinoma, metastatic breast cancer, glioblastoma or a combination thereof.

In certain embodiments, the description provides a method of treating melanoma brain metastasis in a patient comprising administering to a subject in need thereof an effective amount, e.g., a therapeutically effective amount or synergistically effective amount, of a therapeutic composition or formulation as described herein, wherein the composition is effective for treating melanoma brain metastasis.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a composition or formulation according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression and/or under expression of a protein, which leads to a disease state and/or condition.

The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents.

The term "additional anti-cancer agent" is used to describe an anti-cancer agent, which may be combined with compounds according to the present invention to treat cancer. These agents include, for example, everolimus, niacinamide, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

The therapeutic composition of the invention comprises about 1% to about 95% of the active ingredient, single-dose forms of administration preferably comprising about 20% to about 90% of the active ingredient and administration forms which are not single-dose preferably comprising about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier. The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient. The active ingredient is preferably administered to achieve peak plasma concentrations of the active compound of about 0.00001-30 mM, preferably about 0.1-30 µM.

Diagnostic Methods

A diagnostic method provides an indicator that a disease is or is not present. By "diagnosing" and the like as used herein refers to a clinical or other assessment of the condition of a subject based on observation, testing, or circumstances for identifying a subject having a disease, disorder, or condition based on the presence of at least one indicator, such as a sign or symptom of the disease, disorder, or condition. In certain aspects, diagnosing using the methods of the disclosure includes the observation of the subject for multiple indicators of the disease, disorder, or condition in conjunction with the methods provided herein.

A "sample" as used herein refers to a biological material that is isolated from its environment (e.g., blood or tissue from an animal, cells, or conditioned media from tissue culture) and is suspected of containing, or known to contain a diagnostic target of interest, e.g., protein, analyte, nucleic acid, etc. A sample can also be a partially purified fraction of a tissue or bodily fluid (e.g., serum or plasma). A reference sample or a control sample can be a sample from a donor not having the disease or condition, including fluid or tissue from a subject or from the same subject. A reference or control sample can also be from an untreated donor or cell culture not treated with an active agent (e.g., no treatment or administration of vehicle only). A reference or control sample can also be taken at a time point prior to contacting the cell or subject with an agent or therapeutic intervention to be tested or at the start of a prospective study.

In another aspect, the description provides a method for diagnosing an ETBR-related cancer in an individual comprising: a) obtaining a biological sample from a subject; b) contacting the sample with an agent capable of detecting ET-1 nucleic acid or polypeptide (e.g., nucleic acid-based probe, or antibody or fragment thereof) and/or an agent capable of detecting ET-3 nucleic acid or polypeptide (e.g., nucleic acid-based probe, or antibody or fragment thereof); c) detecting binding of the agent to ET-1 and/or ET-3 in the sample; and d) comparing the amount of agent bound to ET-1 and/or ET-3 from the subject with a control, wherein increased ET-1 and/or ET-3 is indicative of a subject with an ETBR-related cancer, and thereby diagnosing a subject as having an ETBR-related cancer. In any of the aspects or embodiments described herein, the method can further comprise e) administering a therapeutic composition/formulation as described herein.

In additional aspects, the description provides methods of selecting an appropriate therapeutic treatment for a subject having an ETBR-related cancer including the steps of: a) obtaining a biological sample from a subject; b) contacting the sample with an agent capable of detecting ET-1 nucleic acid or polypeptide (e.g., nucleic acid-based probe, or antibody or fragment thereof) and/or an agent capable of detecting ET-3 nucleic acid or polypeptide (e.g., nucleic acid-based probe, or antibody or fragment thereof); c) detecting binding of the agent to ET-1 and/or ET-3 in the sample; d) comparing the amount of agent bound to ET-1 and/or ET-3 from the subject with a control, wherein increased ET-1 and/or ET-3 is indicative of a subject with an ETBR-related cancer, and thereby diagnosing a subject as having an ETBR-related cancer; and e) administering a therapeutic composition as described herein. In certain embodiments, the method includes the step of repeating steps a)-d) thereby determining whether the subject is responding to the treatment.

In additional aspects, the description provides methods of monitoring a therapeutic treatment response in a subject having an ETBR-related cancer including the steps of: a) providing a subject diagnosed with having an ETBR-related cancer; b) administering a therapeutic for the treatment of the cancer; c) obtaining a sample from the subject after therapeutic treatment; d) contacting the sample with an agent capable of detecting ET-1 nucleic acid or polypeptide and/or an agent capable of detecting ET-3 nucleic acid or polypeptide; e) detecting binding of the agent to ET-1 and/or ET-3 in the sample; and f) comparing the amount of agent bound to ET-1 and/or ET-3 from the subject with a control thereby evaluating the therapeutic treatment response, wherein an elevated level of ET-1 and/or ET-3 is indicative of little or no therapeutic response, and reduced level of ET-1 and/or ET-3 is indicative of a positive therapeutic response.

In certain embodiments, the diagnostic methods comprise the additional step of administering a therapeutic. In certain embodiments, the same amount of therapeutic is administered. In additional embodiments, a higher dose is administered. In still additional embodiments, the methods include the step of altering the therapeutic treatment and/or regimen. In certain embodiments, the same amount of therapeutic is administered. In additional embodiments, a higher dose is administered. In still additional embodiments, the methods include the step of altering the therapeutic treatment and/or regimen. In certain embodiments, the ETBR-related cancer is at least one of breast cancer, melanoma, squamous cell carcinoma, glioblastoma or a combination thereof.

In an aspect, the description provides a method of determining sensitivity of cancer cells to an endothelin receptor antagonist. The method comprises: a) providing a cancer tissue sample from a patient; b) incubating the tissue sample in the presence of an antibody that binds specifically to ET-1 and/or an antibody that binds specifically to ET-3; and c) detecting the amount of antibody bound to ET-1 and/or ET-3, wherein when ET-1 and/or ET-3 are actively expressed in the cancer, the cancer will be sensitive to an endothelin receptor antagonist therapy.

Detecting the amount of antibody bound to ET-1 and/or ET-3 can be performed with at least one secondary antibody conjugated to a detectable label. That is, the secondary antibody conjugated to a detectable label to that binds to the antibody that binds ET-1, the antibody that binds ET-3, or to both the antibody that binds ET-1 and the antibody that binds ET-3. Furthermore, a further step following c) detecting can include d) administering an effective amount of an endothelin receptor antagonist or an inhibitor of ETBR signaling (such as a caspase-8 inhibitor). For example, administering a therapeutic composition/formulation as described herein.

In another aspect, the description provides a method of determining sensitivity of cancer cells to an endothelin receptor antagonist, the method comprising: providing a tissue sample from cancer cells from a patient that has a cancer; fixing the sample in formalin, embedding in paraffin, cutting sections with a microtome and transferring sections to glass slides suitable for immunohistochemistry; incubating the slides in the presence of an antibody that detects the presence of ET-1 and/or an antibody that detects the presence of ET-3 (e.g., an anti-ET-1 antibody and an anti-ET-3 antibody), at least one secondary antibody which binds to the antibody or antibodies that bind ET-1 and/or ET-3 and is conjugated to a molecule that allows for visualization of the bound antibody complex (e.g., a secondary antibody directed to the anti-ET-1 antibody and an additional secondary antibody directed to the anti-ET-3 antibody), thereby determining that ET-1 and/or ET-3 are actively expressed in the tumor and thus indicating that inhibition of ET-1 and ET-3 binding to an endothelin receptor will exert a therapeutic effect.

In a further aspect, a method of determining sensitivity of cancer cells to an immune based therapy is provide, the method comprises: a) providing a tissue sample from cancer cells from a patient that has a cancer; b) incubating the tissue sample in the presence of an antibody that binds ET-1 and/or an antibody that binds ET-3; and c) detecting the amount of antibody bound to ET-1 and/or ET-3, wherein when ET-1 and/or ET-3 are actively expressed in the tumor and thus indicating that the cancer will not be responsive to the immune based therapy. The amount of antibody bound to ET-1 and/or ET-3 can be performed with at least one secondary antibody conjugated to a detectable label. That is, the secondary antibody conjugated to a detectable label to that binds to the antibody that binds ET-1, the antibody that binds ET-3, or to both the antibody that binds ET-1 and the antibody that binds ET-3. Furthermore, a further step following c) detecting can include d) administering an effective amount of an immune based therapy.

The immune based therapy can be selected from the group consisting of an immune checkpoint inhibitor (e.g., an anti-PD-1 antibody), a cancer vaccine, and a Chimeric Antigen Receptor T-Cell (CAR-T) therapy.

In an aspect, a method of determining sensitivity of cancer cells to an immune based therapy is provided. The method comprises: a) providing a tissue sample from cancer cells from a patient that has a cancer; b) fixing the sample in formalin, c) embedding in paraffin, d) cutting sections with a microtome and transferring sections to glass slides suitable for immunohistochemistry; e) incubating the slides in the presence of an antibody that detects the presence of ET-1 and/or an antibody that detects the presence of ET-3, at least one additional secondary antibody which binds to the antibody that binds to ET-1 and/or ET-3 and is conjugated to a molecule that allows for visualization of the bound antibody complex, thereby determining that ET-1 and/or ET-3 are actively expressed in the tumor and thus indicating that the cancer will not be responsive to the immune based therapy.

In the above aspects, detection of binding of the nucleic acid or antibody to the diagnostic target, e.g., ET-1 nucleic acid or protein can be assayed for by any method well-known in the art. In embodiments, detection includes detection using a reporter system, such as a radiographic or fluorescent label, or an enzymatic reaction. Enzymatic reactions can be catalyzed by an enzyme, for example, luciferase, alkaline phosphatase, or beta-galactosidase. In certain embodiments, the methods include isolating the antibody-antigen complex from the sample, for example by binding the antigen-antibody complex to a solid substrate. In certain embodiments, the antibody-antigen complex is formed in solution. In embodiments, the assay is an immunoassay. Immunoassays include, but are not limited to, competitive and non-competitive assay systems using techniques such as luciferase immunoprecipitation systems (LIPS), BIAcore analysis, fluorescent-activated cell sorter (FACS) analysis, immunofluorescence, immunocytochemistry, Western blots, radioimmunoassays, enzyme-linked immunosorbent assay (ELISA), "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. See Ausubel et al, eds, 1994, Current Protocols in Molecular Biology, Vol. 1, John Wiley & Sons, Inc., New York, which is hereby incorporated by reference.

A variety of immunoassays, including immunofluorescence assays, Western blot, and ELISAs have been employed to detect proteins. (Bacon, et al., 2003. *J Infect Dis* 187:1187-99; Embers, et al., 2007. *Clin Vaccine Immunol* 14:931-6.; Liang, et al., 1999. *J Immunol* 163:556673; and Liang, et al., 1999. *J Clin Microbiol* 37:3990-6).

In certain embodiments, the reporter is a polypeptide that can be readily detected, preferably quantitatively detected, either directly or indirectly. A reporter polypeptide typically has an enzymatic activity, luciferase activity, alkaline phosphatase activity, beta-galactosidase activity, acetyl transferase activity, or the like, wherein catalysis of a reaction with a substrate by the enzyme results in the production of a product, e.g., light, that can be detected at a specific wavelength of light, radioactivity, or the like, such that the amount of the reporter peptide can be determined in the sample, either as a relative amount, or as an absolute amount by comparison to control samples.

Kits

In another aspect, the description provides a kit comprising a container, and reagents for performing any of the methods described herein, or comprising a therapeutic composition as described herein and instructions for their use. In certain embodiments, the kit comprises a container and reagents for detecting a patient that is a candidate for treatment with an Endothelin receptor antagonist, wherein: the kit comprises an antibody specific for ET-1 and/or an antibody specific for ET-3; a secondary antibody that can bind to the ET-1/ET-3 antibodies and is conjugated to a molecule that allows for detection of the bound antibody complex; and a suitable detection system.

Examples

Figure 4A:
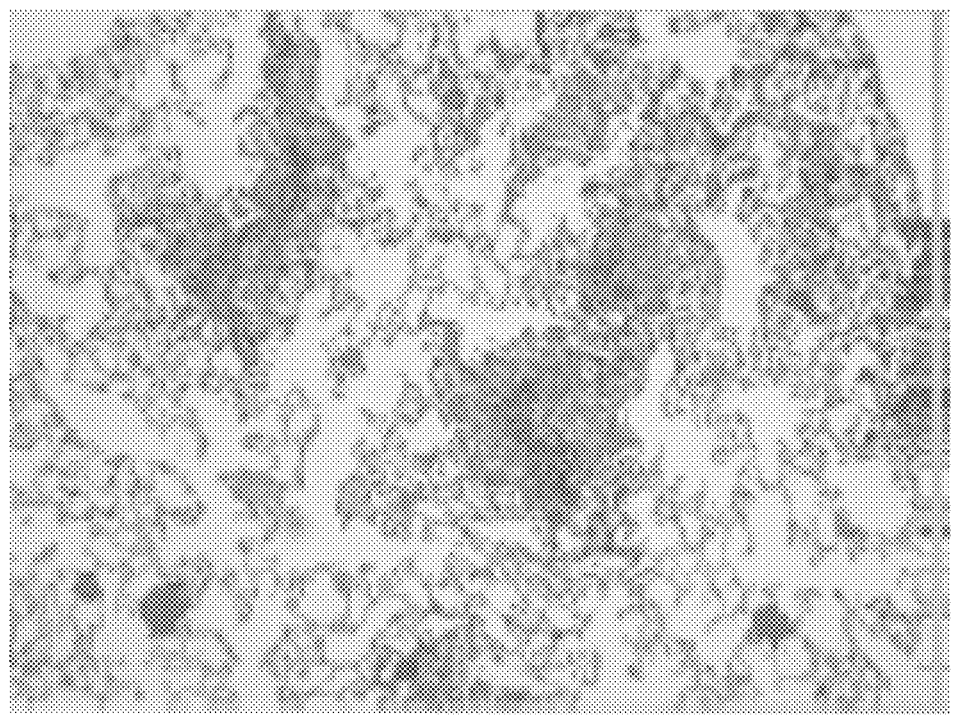
FIGS. 4A and 4B. BQ788 inhibits melanoma growth and metastasis. BQ788 (IC50 1.2 nM, Ki=17.8 nM) is a potent inhibitor of ETBR-related melanoma cell growth. BQ788 induces apoptosis in melanoma tumor cells.
Figure 4B:
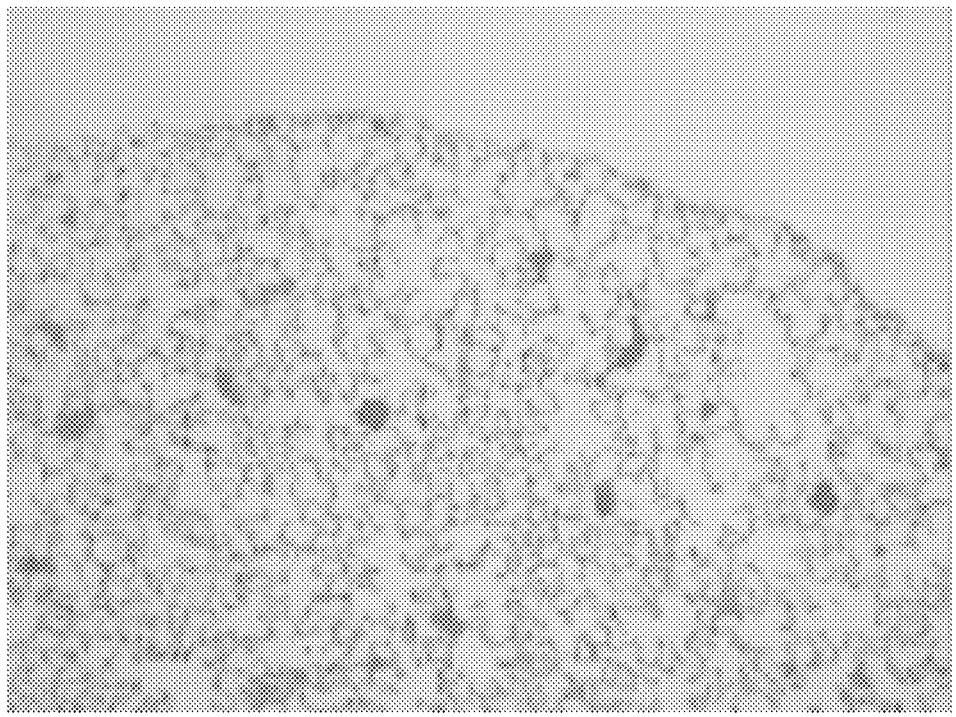
Figure 5A:
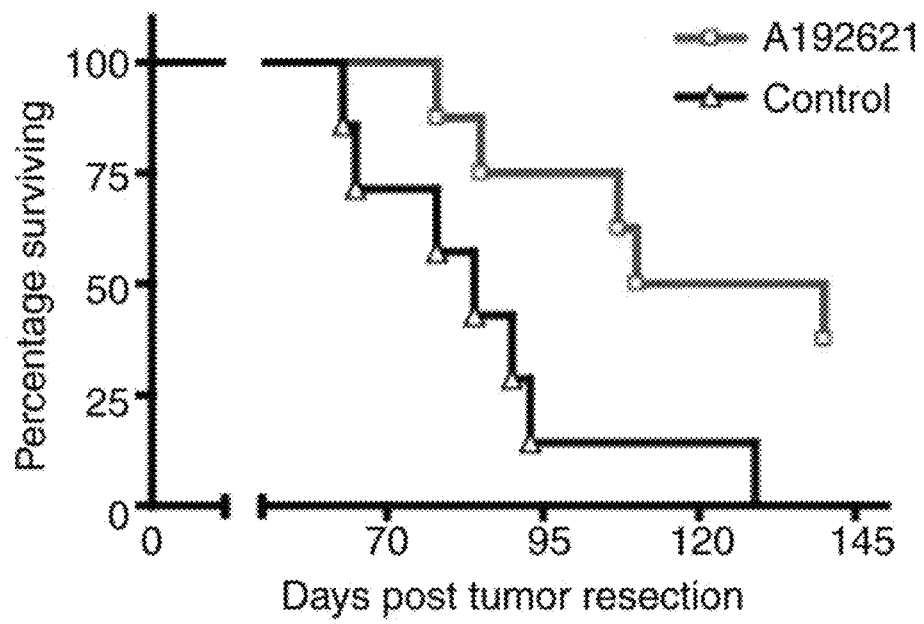
FIGS. 5A, 5B, 5C, 5D, and 5E. ETBR antagonist inhibits melanoma brain metastasis in mice. A192621 (IC50 4.5 nM, Ki=8.8 nM) was administered at a dose of 60 mg/kg/day using a mouse melanoma model. (A) A192621 increases survival; (B-C) shrinks brain melanoma metastases; and (D-E) shrinks CNS melanoma tumors. In this study, lentiviral vectors were used to overexpress ETBR in melanoma cell lines, which were in turn used to implant xenografts in mice.
Figure 5B:
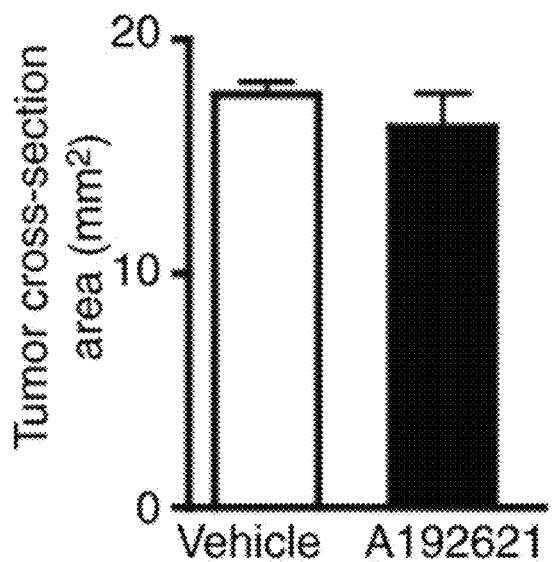
Figure 5C:
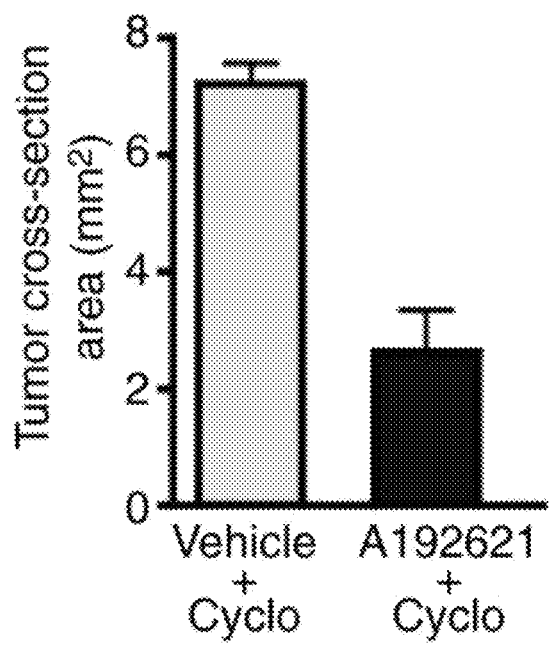
Figure 5D:
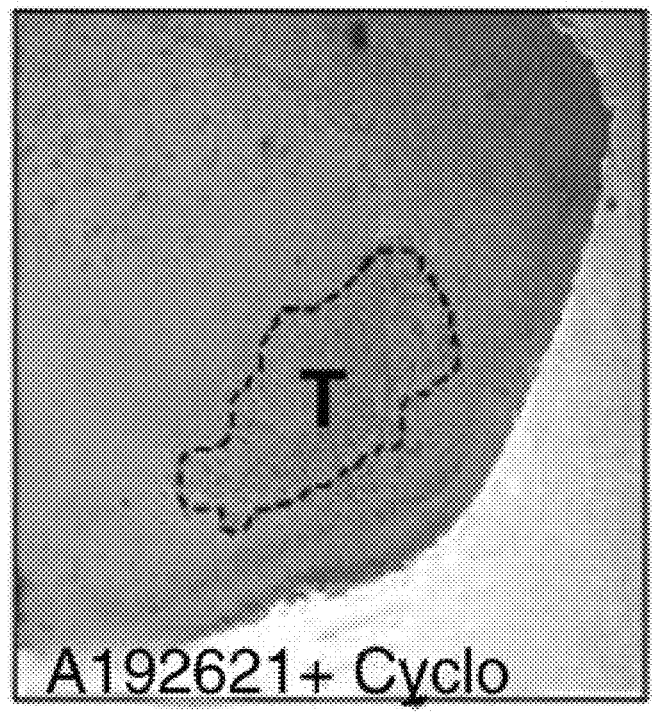
Figure 5E:
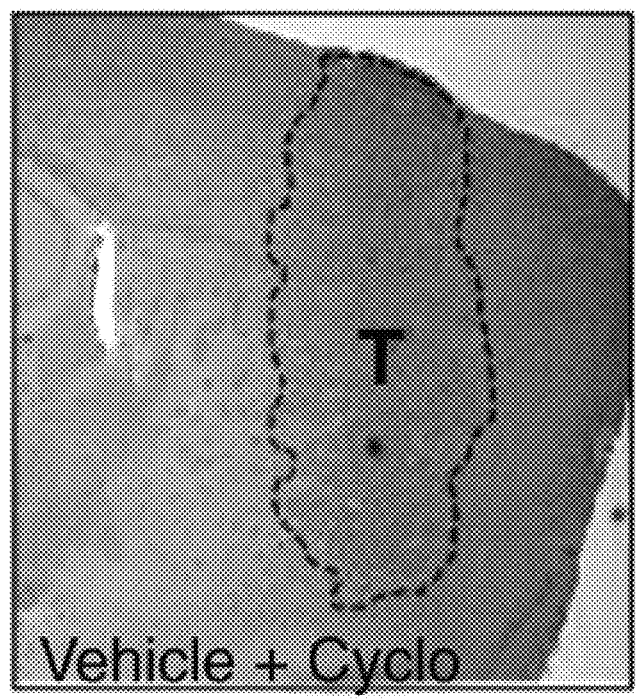

BQ788 Inhibits Melanoma Growth and Metastasis (FIGS. 4A and 4B).

BQ788 is a potent inhibitor of ETBR-related melanoma cell growth (IC50 of 1.2 nM, Ki=17.8 nM). BQ788 induces apoptosis in melanoma tumor cells. Mice were implanted with $1 \times 10^6$ SKMEL28 human melanoma cells. Tumors were established for 10 days until palpable then 120 ng (~60 ug/kg) BQ788 dissolved in DMSO was injected IP 3×per week×6 weeks. Mice were then sacrificed and lungs harvested and tumors weighed. A 75% reduction in tumor weight was observed. Lung specimens harvested from control mice (FIG. 4A) demonstrated numerous metastases whereas specimens harvested form mice treated with BQ788 demonstrated >95% clearance of lung metastases (FIG. 4B).

A192621 Inhibits Melanoma Brain Metastasis in Mice (FIGS. 5A, 5B, 5C, 5D, and 5E).

A192621 demonstrates an IC50 of 4.5 nM, and Ki=8.8 nM. A192621 was administered at a dose of 60 mg/kg/day using a mouse melanoma model. (A) A192621 increases survival; and (B-C-D-E) shrinks brain melanoma metastases. In this study, lentiviral vectors were used to overexpress ETBR in melanoma cell lines, which were in turn used to implant xenografts in mice. In this study, lentiviral vectors were used to overexpress ETBR in melanoma cell lines, which were in turn used to implant xenografts in mice.

Figure 6:
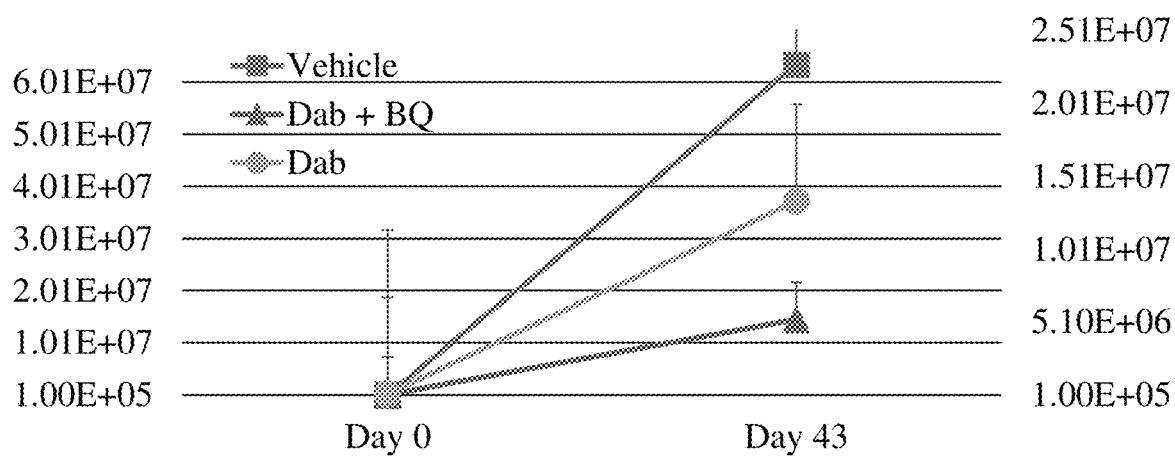
FIG. 6. ETBR antagonist BQ788 synergizes with bRAF inhibitor Dabrafenib in treating brain melanoma xenografts in mice. Nude mice were innoculated intracranially with SKMEL28 human melanoma cells tagged with luciferase. Tumors were allowed to grow for 1 week then mice were randomized into groups (n=8) based on average luminescence of tumors. Mice were treated with Dabrafenib 100 mg/Kg PO daily or Dabrafenib+BQ788 10 ng intranasally TIW. Mice treated with the combination of BQ788+Dabrafenib demonstrated greater growth suppression of brain melanoma xenografts than those that were treated with Dabrafenib alone.

The low side effect profile of BQ788 and A192621 in combination with a SC route of administration will make feasible the treatment of both advanced and earlier stage melanoma patients ETBR Antagonist B0788 Synergizes with a bRAF Inhibitor in Treating Brain Melanoma Xenografts in Mice (FIG. 6).

Nude mice were innoculated intracranially with $1 \times 10^5$ SKMEL28 human melanoma cells tagged with luciferase. Tumors were allowed to grow for 1 week, then mice were randomized into groups (n=8) based on average luminescence of tumors. Mice were treated with Dabrafenib 100 mg/Kg PO daily or Dabrafenib+BQ788 10 ng intranasally TIW. Control mice were treated with vehicle. Tumor luminescence was measured over a period of 43 days. Mice treated with the combination of BQ788+Dabrafenib demonstrated greater growth suppression of brain melanoma xenografts than those that were treated with Dabrafenib alone.

Figure 7:
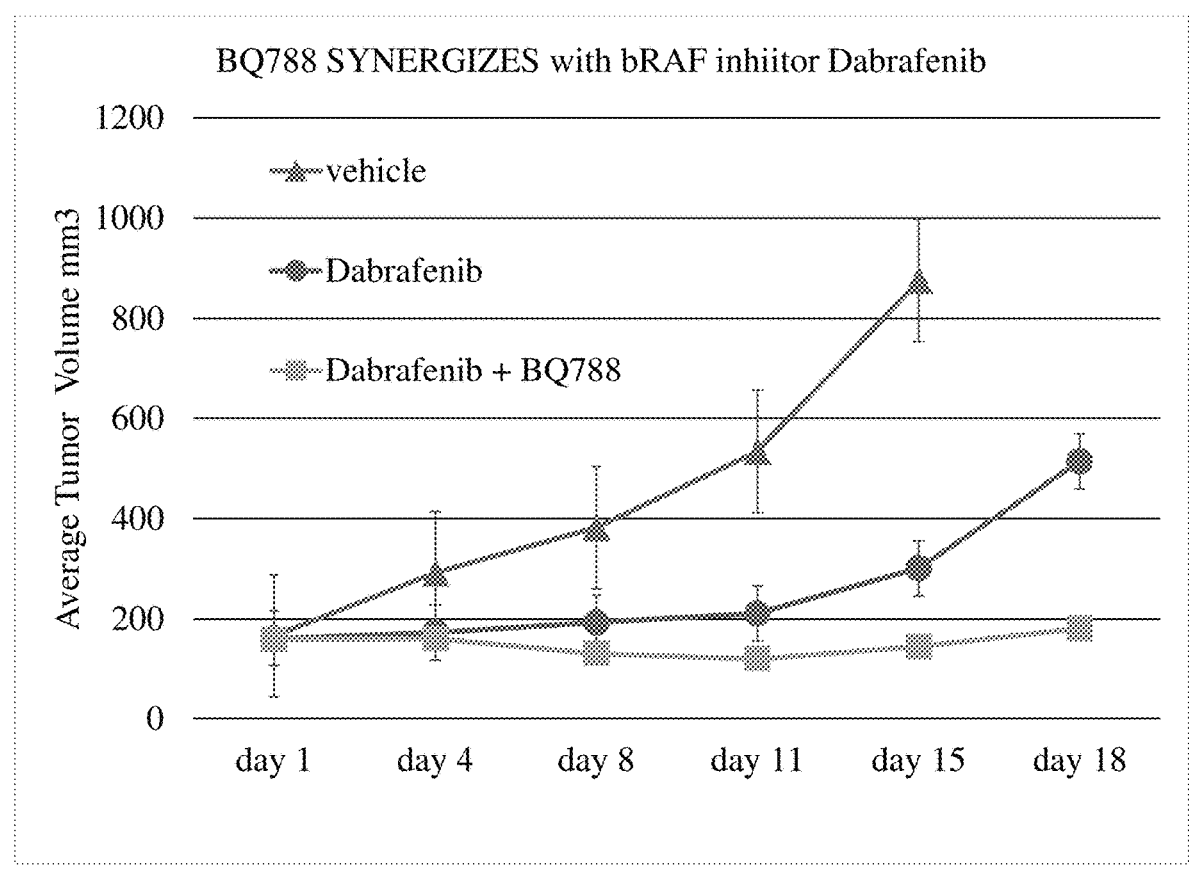
FIG. 7. BQ788 synergizes with Dabrafenib in vivo. A375 human melanoma cells were implanted subcutaneously into the rear flank of Nu/J nude mice and allowed to grow to 150 mm3-200 mm3 prior to randomization and initiation of treatment. The mice received the following treatments: (1) vehicle (n=8), (2) Dabrafenib 100 mg/Kg PO daily (n=5), and (3) Dabrafenib+BQ788 600 ng IP TIW (n=5). Dabrafenib alone retarded tumor growth. Dabrafenib in combination with BQ788 resulted in tumor shrinkage below baseline by day 11 ($p<0.05$).

BQ788 Synergizes with a bRAF Inhibitor In Vivo (FIG. 7).

A375 human melanoma cells ($3 \times 10^6$) were implanted subcutaneously into the rear flank of Nu/J nude mice and allowed to grow to 150 mm3-200 mm3 prior to randomization and initiation of treatment. The treatment groups were as follows: (1) vehicle (n=8), Dabrafenib 100 mg/Kg PO daily (n=5), (2) Dabrafenib+BQ788 600 ng IP 3×per week (n=5). While Dabrafenib alone retarded the growth of tumors, the addition of BQ788 resulted in tumor shrinkage below baseline by day 11 ($p<0.05$).

Figure 8:
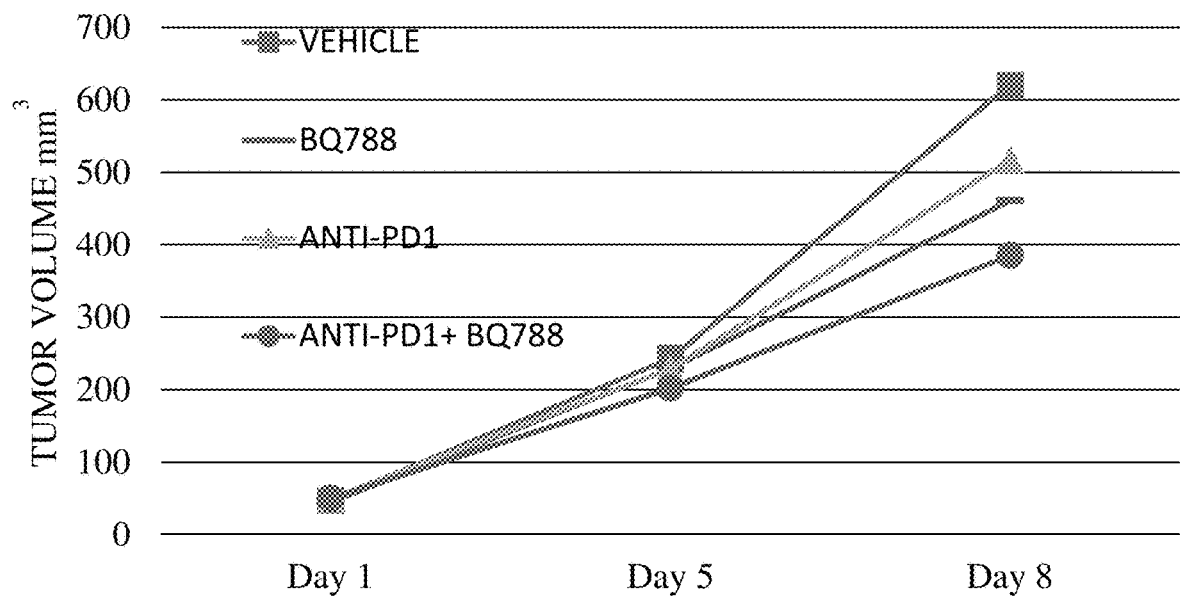
FIG. 8. BQ788 synergizes with anti-PD1 antibody in syngeneic mouse melanoma model. C57Bl/6 mice were inoculated with B16F10 mouse melanoma cells into the rear flank. Once tumors were palpable, mice were randomized into 4 groups (n=5) and treated as follows: (1) vehicle, (2) BQ788, (3) Anti-PD1, or (4) Anti-PD1+BQ788. The data in the graph reflect tumor growth after 3 doses of test articles and demonstrates a synergism between BQ788 and anti-PD1.

BQ788 Synergizes with Anti-PD1 Antibody in Syngeneic Mouse Melanoma Model (FIG. 8).

C57Bl/6 mice were innoculated with $2 \times 10^5$ B16F10 mouse melanoma cells into the rear flank. Once tumors were palpable, mice were randomized into 4 groups (n=5) and treated as follows: (1) vehicle (10 ul DMSO I.P. TIW, 100 ug isotype control antibody I.P. TIW), (2) BQ788 (600 ng BQ788 I.P. TIW, 100 ug isotype control antibody I.P. TIW), (3) Anti-PD1 (10 uL DMSO I.P. TIW, 100 ug mouse anti-PD1 I.P. TIW), or (4) Anti-PD1+ENB001 (600 ng BQ788 I.P. TIW, 100 ug mouse anti-PD1 I.P. TIW). The data in the graph reflect tumor growth after 3 doses of test articles and demonstrates a synergism between BQ788 and anti-PD1.

Figure 9:
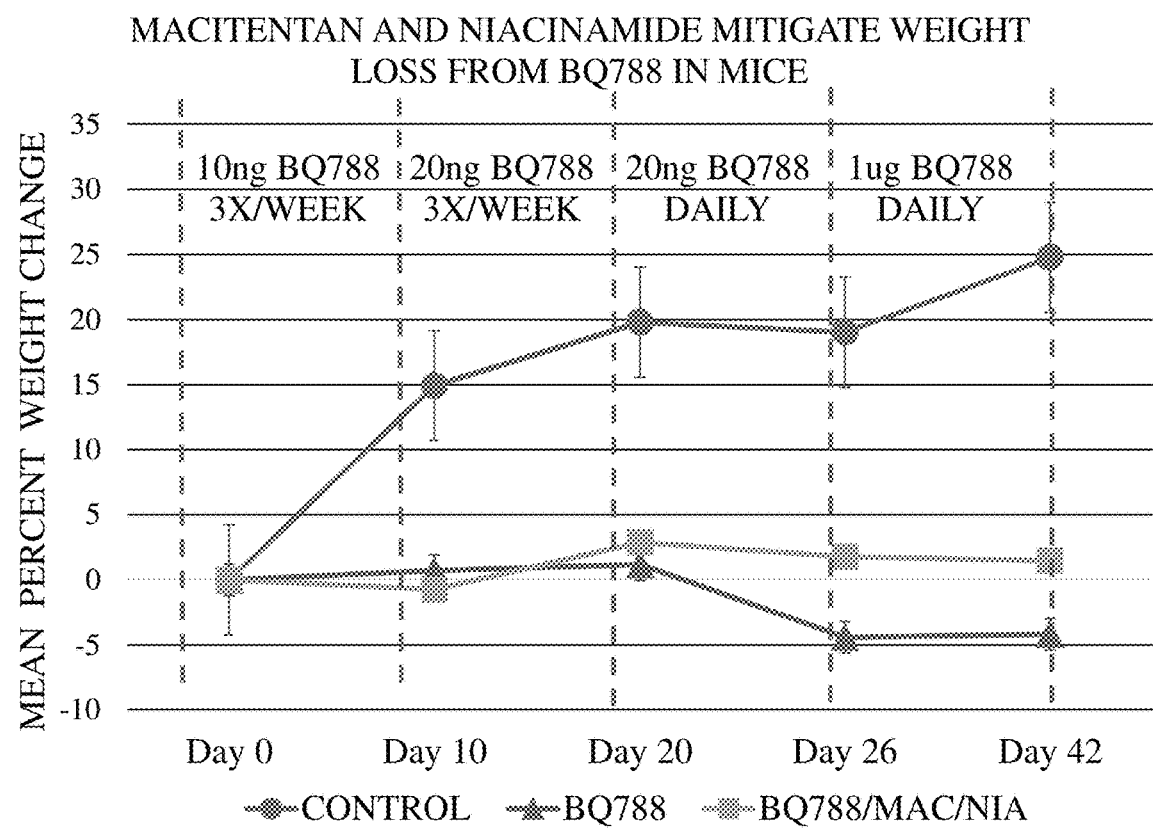
FIG. 9. ETAR antagonist and Niacinamide mitigate weight loss from BQ788. Six week old athymic nude mice were administered the ETBR antagonist BQ788 intranasally in 20% DMSO at the indicated ascending doses over a period of 42 days. One group was additionally administered the ETAR antagonist Macitentan orally at a dose of 5 mg/kg daily. The drinking water of these mice was supplemented with the B vitamin niacinamide at a concentration of 0.3 mg/mL. Animals treated with BQ788 alone failed to thrive and experienced an average weight loss of 5% relative to baseline body weight by the end of the study. Co-administration of the ETAR antagonist Macitentan with niacinamide supplementation mitigated this weight loss. Animals thus treated were able to maintain body weight throughout the study. Co-administration of ETAR antagonists and niacinamide with ETBR antagonists mitigated the adverse effects of ETBR antagonists when administered for therapeutic purposes.

ETAR Antagonist and Niacinamide Mitigate Weight Loss from BQ788 (FIG. 9).

Six week old athymic nude mice (n=3 per group) were administered the ETBR antagonist BQ788 intranasally in 20% DMSO at the indicated ascending doses over a period of 42 days. One group was additionally administered the ETAR antagonist Macitentan orally at a dose of 5 mg/kg daily. The drinking water of these mice was supplemented with the B vitamin niacinamide at a concentration of 0.3 μg/mL. Animals treated with BQ788 alone failed to thrive and experienced an average weight loss of 5% relative to baseline body weight by the end of the study. Co-administration of the ETAR antagonist Macitentan with niacinamide supplementation mitigated this weight loss. Animals thus treated were able to maintain body weight throughout the study. Co-administration of ETAR antagonists and niacinamide with ETBR antagonists mitigated the adverse effects of ETBR antagonists when administered for therapeutic purposes.

Endothelin-1 in the Tumor Microenvironment Correlates with Melanoma Invasion.

Tissue Specimens.

Formalin-fixed, paraffin-embedded, deidentified human tissue specimens of melanocytic nevi, melanoma in situ, invasive melanomas, and blue nevi were obtained from the archives of the Dermatopathology Section, New York University School of Medicine. Specimens are described in Table 1. Specimens were not archived for a period exceeding 2 years. All protocols associated with this study received the approval of the institutional review board.

Immunohistochemistry.

Figure 10A:
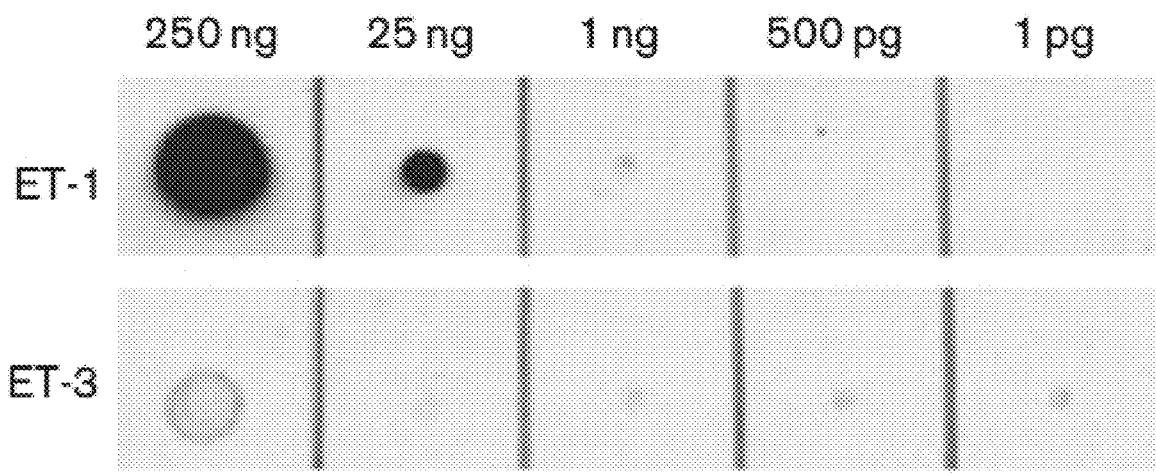
FIGS. 10A, 10B, and 10C. Endothelin-1 (ET-1) immunohistochemical staining of melanocytic nevi. (A) ET-1 and ET-3 peptides ranging from 1 pg to 250 ng in concentration were immobilized on membranes and hybridized using an anti-ET-1 monoclonal antibody. (B) A representative compound congenital melanocytic nevus. (C) A representative dysplastic nevus with severe cytologic atypia. Scattered cells in the perilesional environment in both specimens are positive for ET-1 (arrows). Melanocytes in these specimens are negative for ET-1. Hematoxylin and eosin (H&E) stained sections are shown in the left panels. ET-1 immunohistochemical stains of specimens are shown in the right panels. ET-1 stains red.
Figure 10B:
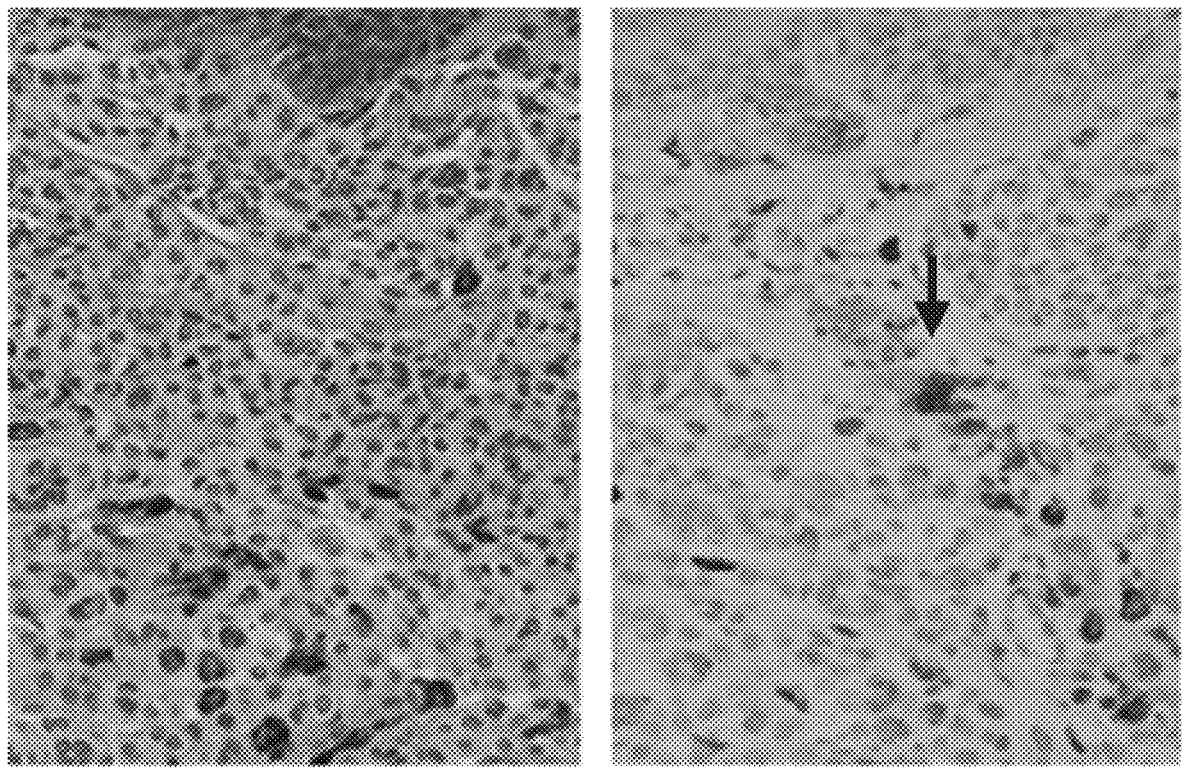
Figure 10C:
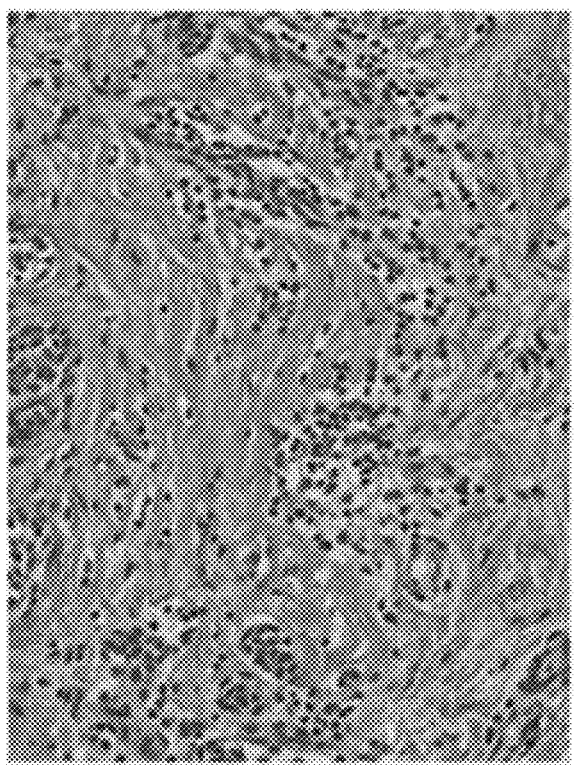
Figure 10C:
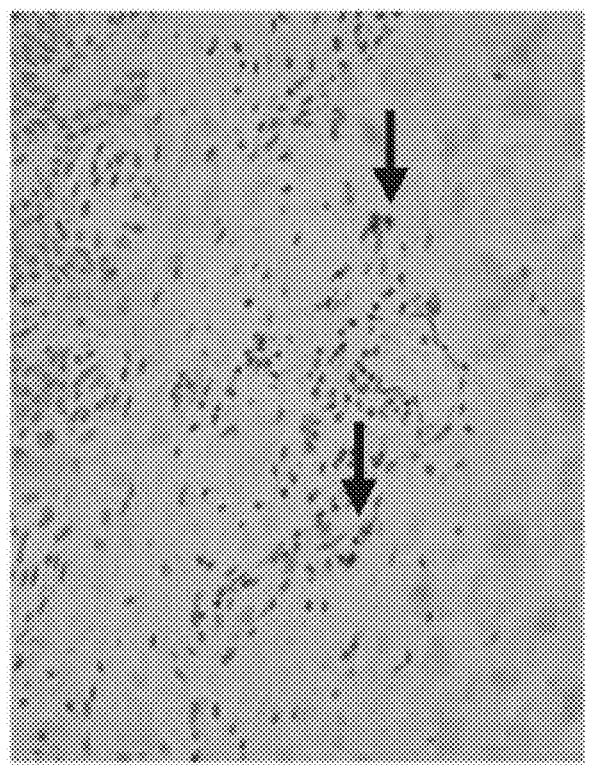
Figure 11A:
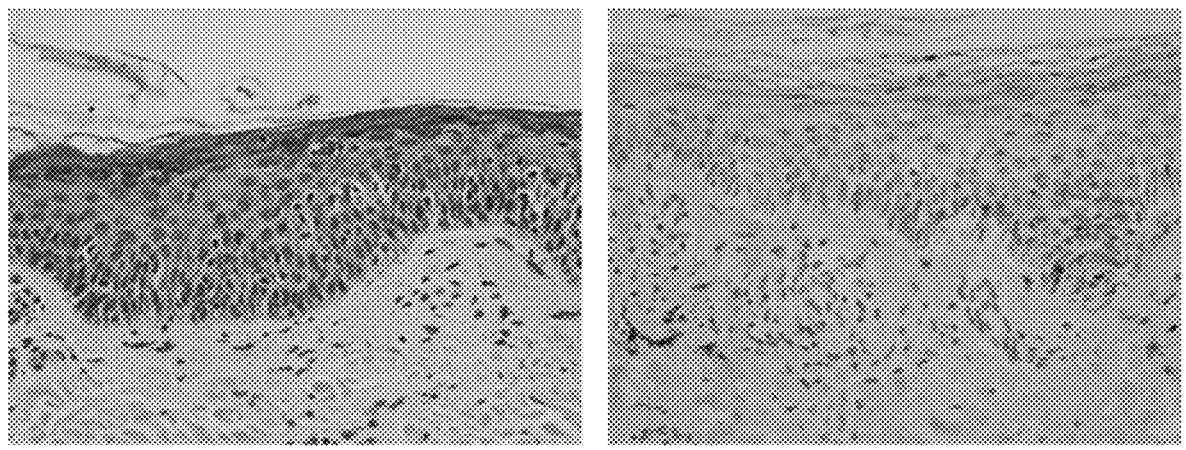
FIGS. 11A and 11B. Endothelin-1 (ET-1) immunohistochemical staining of melanoma in situ specimens. (A) A representative melanoma in situ specimen that is negative for ET-1-positive cells in the dermal infiltrate [hematoxylin and eosin (H&E) staining: left panel, ET-1 immunohistochemical (IHC) staining: right panel]. (B) A representative melanoma in situ specimen with numerous ET-1-positive cells in the dermal infiltrate (indicated by arrows). H&E stain: left panel, ET-1 IHC: middle and lower panels (high magnification).
Figure 11B:
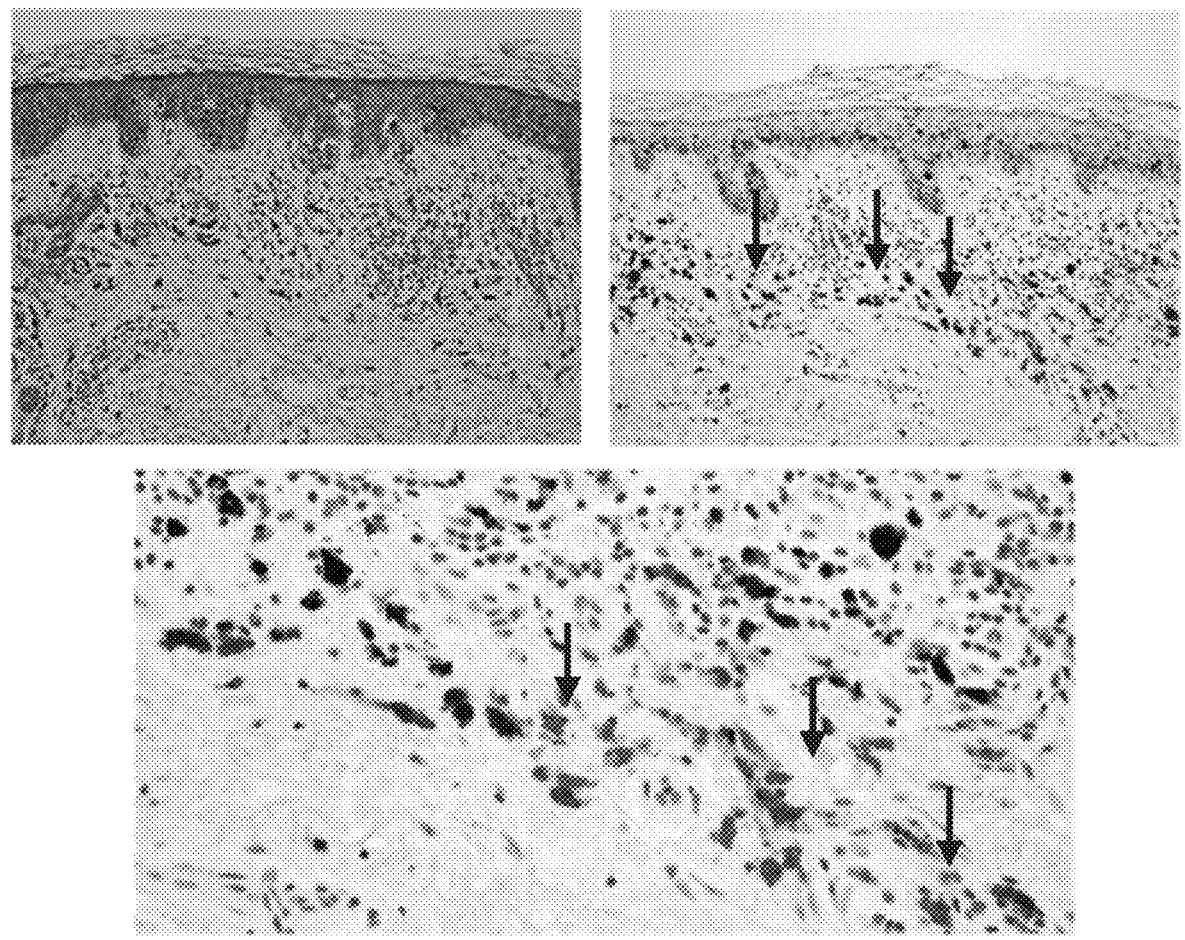

Immunohistochemical (IHC) analysis was carried out on 4 μm-thick, formalin-fixed, paraffin-embedded tissue sections with the following antibodies: mouse antihuman ET-1, clone TR.ET.48.5 (Affinity Bioreagents, Golden, Colo., USA); mouse anti-human CD68, clone KP1 (Dako, Carpinteria, Calif., USA); and mouse antihuman melanosome, clone HMB45 (Ventana Medical Systems, Tucson, Ariz., USA). IHC staining conditions were determined using a 3-mm tissue macroarray consisting of normal skin, melanoma, lymph nodes, and thymus. Antigen retrieval requirements were first determined, and then the antibody was serially diluted to determine the optimum dilution/concentration. For double-label IHC staining and azure B counterstaining we optimized the CD68 and HMB45 stain to the ET-1 antigen retrieval conditions and then used an ET-1-brown and HMB45/CD68 red sequential label protocol. Briefly, sections were deparaffinized in xylene (three changes), rehydrated through graded alcohol (three changes 100% ethanol, three changes 95% ethanol), and rinsed in distilled water. Heat-induced epitope retrieval was performed in 10 mmol/l citrate buffer (pH 6.0) in a 1200 W microwave oven at 90% power. ET-1 and CD68 were retrieved for 10 and 5 min, respectively. Sections were allowed to cool for 30 min and then rinsed in distilled water. Antibody incubation and detection were carried out on a NEXes platform (Ventana Medical Systems Tucson, Ariz., USA) using Ventana's buffer and detection system, unless otherwise specified. Both CD68 and melanosome were applied neat (prediluted) and incubated for 30 min at 40° C. ET-1 was diluted 1:800 in Dulbecco's PBS (Life Technologies Grand Island, N.Y., USA) and incubated overnight at room temperature. All three antibodies were detected using iView biotinylated goat anti-mouse antibody, followed by application of the streptavidin-alkaline phosphatase conjugate. The complex was visualized with Naphthol-AS-MX phosphatase and Fast Red complex. The slides were washed in distilled water, counterstained with hematoxylin, dehydrated, and mounted with permanent media. Positive (tissue macroarray) and negative (PBS substituted antibody) controls were included with the sections. Staining was optimized using normal skin specimens to determine the dilution of antibody that yielded no background staining in controls specimens. Doublelabeling for ET-1/CD68 and ET-1/melanosome was performed in sequence on the NEXes platform, with peroxidase/3,3 diaminobenzidene enzyme detection first, followed by alkaline phosphatase/Fast Red detection. Briefly, antigen retrieval was performed for ET-1 and CD68 as described above. Endogenous peroxidase activity was blocked with hydrogen peroxide. ET-1 was diluted and incubated overnight as described above. ET-1 was detected with iView biotinylated goat antimouse antibody, followed by application of the streptavidin-horseradish peroxidase conjugate. For specimens to be considered positive for ET-1 staining, there had to be a clear focus of ET-1-positive macrophages or melanoma cells. The cutoff for ET-1 staining was the presence of at least 5% of cells in a given population, and it took into consideration the percentage of positive cells as follows: +1, less than 33% but greater than 5%; +2, greater than 33% but less than 65%; +3, greater than 66%; and +3=strong; +2=moderate; +1=weak; 0=no staining. The complex was visualized with 3,3 diaminobenzidene and enhanced with copper sulfate. The slides were then washed extensively and labeled for CD68 or melanosome with alkaline phosphatase/Fast Red as described above. Counterstaining with Azure b was performed according to the method of Kamino and Tam[14], without modification.

archived human tissue specimens were analyzed for this study (Table 1). An alkaline phosphatase stain using a red chromogen was used to permit differentiation between melanin (brown) and a positive signal for ET-1 (red). In 26% of melanocytic nevi, ET-1-positive cells were detected in the perilesional dermal infiltrate. However, most specimens tested demonstrated no or rare ET-1-positive melanocytes (FIGS. 10B and 10C). Melanoma in situ lesions are superficial noninvasive melanomas. Of these lesions, 44% demonstrated ET-1-positive cells in the perilesional dermal infiltrate and 22% demonstrated ET-1-positive melanoma cells (FIG. 11).

Figure 12A:
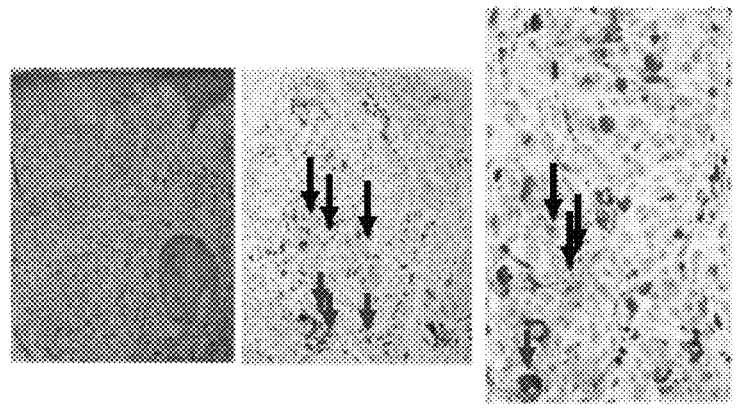
FIGS. 12A, 12B, 12C, and 12D. Endothelin-1 (ET-1) immunohistochemical staining of invasive melanomas. (A, B) Two different specimens of invasive melanomas are shown at low magnification (left, center panels) and high magnification (right panel). Left panels are hematoxylin and eosin (H&E) stains for each. Middle and right panels are immunohistochemical (IHC) stains. Numerous ET-1-positive cells in the dermal infiltrates (short, blue arrows) are indicated, as well as ET-1-positive melanoma cells (long, black arrows). (C) High magnification of a third specimen stained for H&E (left panel) and ET-1 (right panel). (D) ET-1-positive cells in the microenvironment of invasive melanoma cells express the macrophage marker CD68. A representative slide is shown that is stained for both anti-ET-1 (brown) and anti-CD68 (red) antibodies. Short, blue arrows indicate cells that were only positive for CD68. Long, black arrows indicate cells that are positive for both ET-1 and CD68.
Figure 12B:
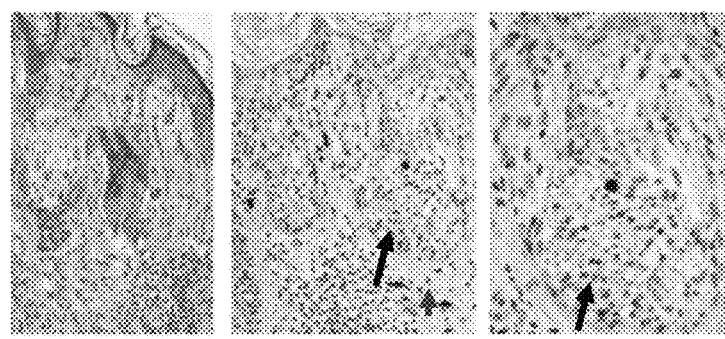
Figure 12C:
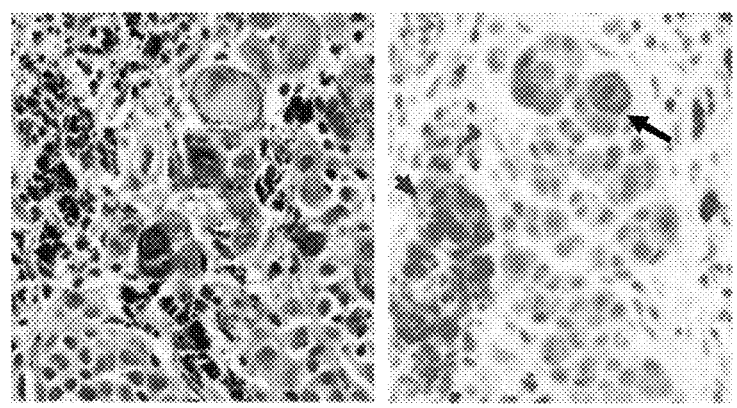

In sharp contrast to melanocytic nevi and melanoma in situ specimens, the majority of invasive melanomas contained numerous cells positive for ET-1 expression in the tumor microenvironment (FIGS. 12A-12C). In addition, nests of melanoma cells strongly positive for ET-1 were observed. Of the 23 invasive melanomas analyzed, 74% overall were associated with numerous ET-1-positive cells in the tumor microenvironment. However, 100% of moderately to highly pigmented invasive melanomas were associated with an ET-1-positive tumor microenvironment, in contrast to 33% of hypopigmented melanomas. Thereby

TABLE 1

Tissues and characteristics

| Type | N | ET-1 + infiltrate [n (%)] | ET-1 + melanocytes/melanoma cells [n (%)] |
|---|---|---|---|
| Melanocytic nevi | 19 | 5 (26) | Rare, few ET-1 + cells in four specimens |
| Melanoma in situ | 9 | 4 (44) | 2 (22) |
| Invasive melanoma | 23 | 17 (74) | 12 (52) |
| Invasive melanoma, moderately to heavily pigmented | 14 | 14 (100) | 11 (79) |
| Metastatic melanoma | 68 | 15 (22) | 29 (43) |
| Metastatic melanoma moderately to heavily pigmented | 29 | 14 (48) | 18 (62) |
| Blue nevi | 18 | 16 (89) | Rare, few ET-1 + cells in three specimens |

ET-1, endothelin-1.

Statistical Analyses.

$\chi^2$-Tests were used to test the hypotheses for statistical significance in categorical comparisons, and Fisher's exact tests were used when sample sizes were too small for $\chi^2$-tests. Statistical significance of the associations is reported using two-sided P-values, with a P-value less than 0.05 as the criterion for significance. Odds ratios (ORs) were used as a measure of strength of the association and are presented with 95% confidence intervals (CIs). SPSS version 22 (SPSS Inc., Chicago, Ill., USA) was used for statistical calculations.

Anti-ET-1 Antibody Demonstrates Very Low Cross-Reactivity to the ET-3 Isoform.

A previous study reported low levels of ET-1 expression in metastatic melanoma cells but elevated levels of expression of the ET isoform, ET-315. As ET-1 and ET-3 are closely related, we determined the specificity of the ET-1 antibody by a dot-blot analysis of immobilized ET-1 and ET-3 (FIG. 10). Only a very weak cross-reacting signal was found for the anti-ET-1 antibody with 250 ng of ET-3, an extremely high and nonphysiological level of protein, which was not seen at lower levels of protein. The ET-1 antibody is therefore highly specific for ET-1.

Figure 12D:
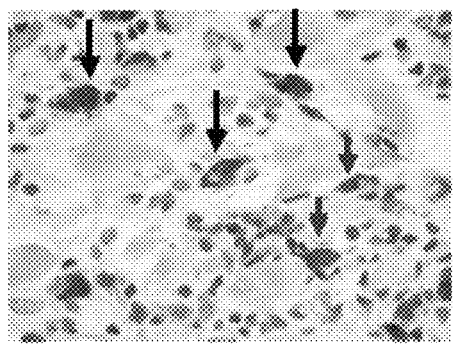

Endothelin-1 expression in melanocytic cells and the tumor microenvironment increases with the extent of melanoma tumor progression. To determine whether ET-1 is expressed in the microenvironment of pigmented lesions, we performed an IHC screen of melanocytic nevi and melanoma in situ lesions. Formalin-fixed, paraffin-embedded, demonstrating a correlation between ET-1 expression and melanoma invasion, as well as melanoma pigment production. Histologic features of ET-1-positive cells in the dermal microenvironment of pigmented lesions suggested that they might be of macrophage origin. We therefore carried out IHC analysis of specimens using antibodies directed against CD68, a standard macrophage marker. The dermal infiltrate associated with invasive melanoma was double stained with anti-ET-1 (brown chromogen) and anti-CD68 (red chromogen; FIG. 12D). The short, blue arrows in FIG. 12 indicate cells that express CD68 alone. These cells are bright red/pink in color. The black, long arrows in FIG. 12 point to cells that express both ET-1 and CD68. These cells have a darker brown-red hue than the singly stained cells because of the presence of both brown and red stains that represent ET-1 and CD68 expression, respectively. These results demonstrate that the ET-1-positive cells in the tumor microenvironment are of macrophage origin.

Co-Localization of ET-1 with Melanoma Tumor Marker HMB45 in Invasive Melanomas.

Figure 13A:
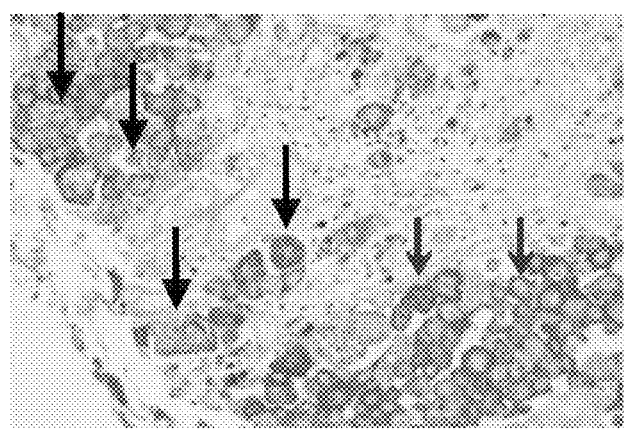
FIGS. 13A and 13B. Endothelin-1 (ET-1) and HMB45 immunohistochemical staining of an invasive melanoma. (A) An invasive melanoma specimen double stained with ET-1 (brown) and HMB45 (red) and counterstained with azure blue (left panel). Short, blue arrows indicate cells that are positive for HMB45. Long, black arrows indicate cells that are positive for HMB45 as well as ET-1. (B) Azure blue counterstain alone.

FIG. 13 represents an invasive melanoma specimen with nests of large ET-1-positive cells with an epithelioid morphology. To verify that these ET-1-positive cells are indeed melanoma cells, the specimens were stained for both ET-1 and HMB45, a melanoma tumor marker, and then counterstained with azure blue, which stains melanin granules green-blue, to facilitate interpretation. As shown in FIG. 13A, scattered cells within the cluster of melanoma cells are positive for ET-1 (brown chromogen) as well as HMB45

Figure 13B:
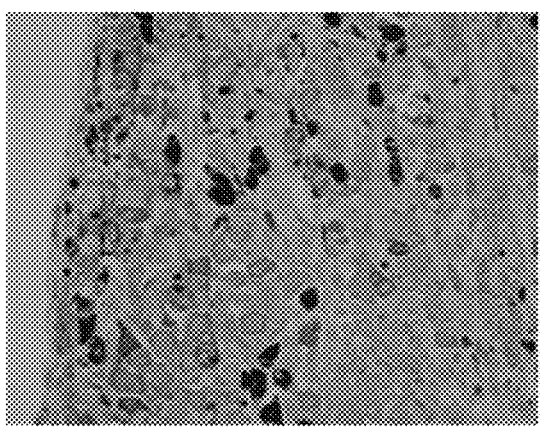

(red chromogen). The same specimen stained with azure blue alone demonstrates no brown pigment from melanin (FIG. 13B). Thus, the ET-1-expressing cells are melanoma cells in origin.

ET-1 Expression in Metastatic Melanomas and Blue Nevi.

Figure 14A:
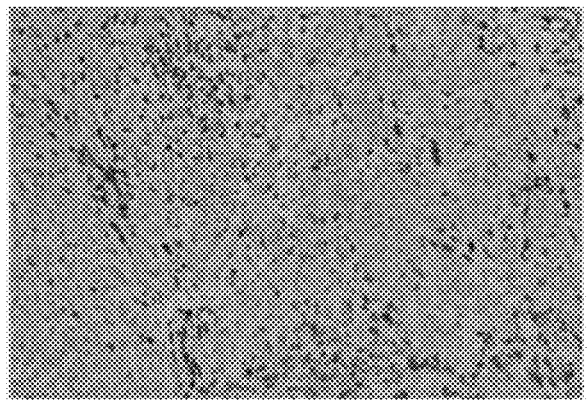
FIGS. 14A, 14B, 14C, 14D, and 14E. ET-1 expression in metastatic melanomas and blue nevi. (A) A metastatic melanoma specimen stained with ET-1. (B) The same specimen stained with melanoma tumor marker HMB45. (C) A blue nevus stained with hematoxylin and eosin. (D, E) The same specimen stained for ET-1 (red chromogen). The short, blue arrow points to an ET-1-positive macrophages. The long, black arrow points to an ET-1-negative melanocyte in blue nevi.
Figure 14B:
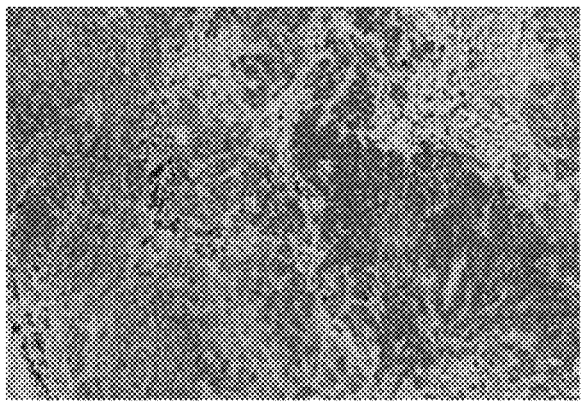

Melanoma metastases (FIG. 14, representative images) were stained for ET-1 expression (red chromogen, FIG. 14A) and for expression of the melanoma tumor marker HMB45 (red chromogen, FIG. 14B). Of the highly pigmented metastatic melanomas, 62% demonstrated ET-1 expression in melanoma cells, in contrast to 28% of hypopigmented metastatic melanomas, again demonstrating a significant correlation between ET-1 expression and pigment production. The overall percentage of metastatic melanoma specimens with cells expressing ET-1 was 43%, as compared with 52% of invasive melanomas. A possible reason for this finding is that the majority of metastatic specimens tested were hypopigmented (57%). However, the true incidence of hypopigmented melanomas is approximately 5% or less; hence, these lesions were disproportionately represented in our study. As ET-1 expression is lower in hypopigmented melanomas, the true overall incidence of ET-1 expression in metastatic melanoma is likely much higher than the 43% observed in our study.

Figure 14C:
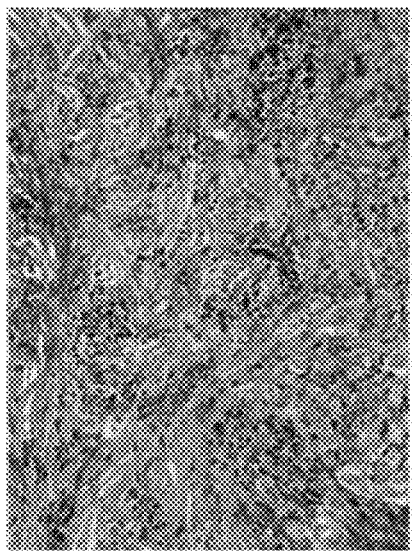
Figure 14D:
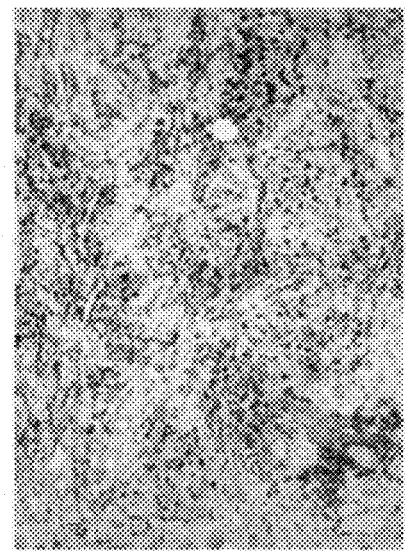
Figure 14E:
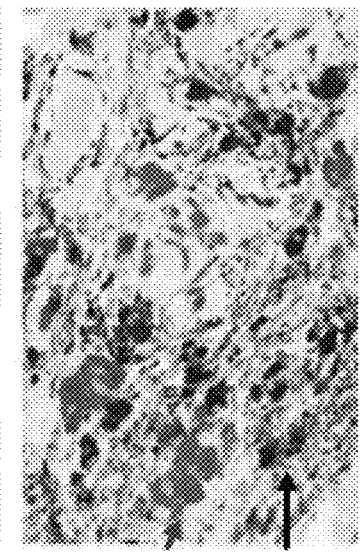

We also analyzed blue nevi for ET-1 expression. Blue nevi are a special subset of melanocytic nevi that are localized to the deep dermis and are thought to represent proliferations of melanocytes that were interrupted in their embryonic migration to the epidermis. Sixteen of 18 (89%) blue nevi contained numerous ET-1-positive cells in the dermal infiltrate (FIGS. 14C-14E). The ET-1-positive cells within these lesions demonstrate histopathologic features consistent with macrophages and melanophages and were positive for CD68 expression (data not shown). As observed with melanocytic nevi, no or rare ET-1 expression was detected in melanocytes within blue nevi.

ET-1 Expression is Significantly Correlated with Invasion, Pigmentation, and Melanoma Progression.

For statistical hypothesis testing, ET-1 positively, invasiveness, and pigmentation were determined for each biopsy specimen and were defined as categorical variables with two categories each. An ET-1-positive specimen was defined as having greater than 5% of cells expressing ET-1, whereas a negative specimen had 5% or less. Noninvasive lesions included melanocytic nevi and melanoma in situ, invasive lesions included invasive melanomas and, when feasible in some analyses, metastatic melanomas. Pigmentation categories were hypopigmented and pigmented (including moderately to highly pigmented). We first determined whether the increase in ET-1 expression in the perilesional infiltrate observed in invasive specimens relative to noninvasive specimens was statistically significant. Nine of 28 (32.1%) noninvasive lesions (nevi and melanoma in situ lesions combined) demonstrated ET-1 positively of the perilesional infiltrate. Seventeen of 23 (73.9%) invasive melanomas tested demonstrated an ET-1-positive perilesional infiltrate. The proportion of positive tests was significantly higher for the invasive group relative to the noninvasive group [P<0.01, OR=6.0 (95% CI 1.8, 20.3)]. Metastatic melanomas were excluded from this analysis because in many cases, because of their large mass, biopsies only captured tumor tissue and excluded peripheral tissues. Blue nevi were excluded from this analysis because of their different biological origin. Next, we analyzed differences in ET-1 expression in melanocytes and melanoma cells, comparing invasive with noninvasive specimens. Two of 28 (7.1%) noninvasive specimens demonstrated ET-1 expression in melanocytic cells. In contrast, 41 of 91 (45.1%) invasive specimens demonstrated ET-1 expression in melanoma cells (invasive melanomas and metastatic melanomas combined). The proportion of positive tests was significantly higher for the invasive group than for the noninvasive group [P<0.01, OR 10.7 (95% CI 2.4, 48)]. Therefore, the association between ET-1 expression and invasion is of statistical significance.

The correlation between pigmentation and ET-1 expression was examined next. Nevi and melanoma in situ lesions were excluded from these analyses because there was no hypopigmented subset for these groups. Fourteen of 14 (100%) invasive melanomas that were moderately to highly pigmented demonstrated ET-1 expression in the perilesional infiltrate, whereas three of nine (33%) hypopigmented melanomas demonstrated ET-1 positively of melanoma cells. The proportion of positive tests in the pigmented group was significantly greater than in the hypopigmented group (P<0.01, OR was infinitely large because of zero ET-1-negative strongly or moderately pigmented lesions). In terms of ET-1 expression of melanoma cells, 11 of 14 (79%) moderately to highly pigmented invasive melanomas demonstrated ET-1-positive melanoma cells. One of nine (11%) hypopigmented invasive melanomas demonstrated ET-1 expression in melanoma cells. The proportion of positive tests was significantly higher for the pigmented group than for the hypopigmented group [P<0.01, OR of 29 (95% CI 2.6, 336)]. Eighteen of 29 (62%) moderately to strongly pigmented metastatic melanomas demonstrated ET-1 expression in melanoma cells, whereas 11 of 39 (28%) hypopigmented metastatic melanomas demonstrated ET-1 expression in melanoma cells. The proportion of positive tests in the pigmented group was significantly higher than in the hypopigmented group [P<0.01, OR of 4.2 (95% CI 1.5, 11.6)]. Overall, we conclude that there is a statistically significant association between ET-1 expression and pigmentation in both invasive melanomas and metastatic melanomas.

Next, we analyzed whether the increase in ET-1 expression in the microenvironment during melanoma progression is statistically significant. Metastatic melanomas were excluded from this analysis for the abovementioned reasons. Of regular nevi, melanoma in situ lesions, and invasive melanomas, 26, 44, and 74%, respectively, demonstrated ET-1 expression in the perilesonal infiltrate. The proportion of infiltrate cells with positive ET-1 tests was thus higher in the more progressed disease states, and this was statistically significant (P<0.01).

DISCUSSION

The data presented here provide the first in-vivo evidence associating ET-1 in the tumor microenvironment to melanoma progression in humans. Although it is well documented that ET-1 stimulation of melanocytes and melanoma cells elicits molecular events known to promote melanoma invasion and metastasis, all data generated to date have been from in-vitro studies or from studies in mice[16, 17, 18, 19, 20]. The microenvironment of melanocytic cells in vivo can have a marked effect on their phenotype, altering it significantly from what is observed in vitro. A strong association between ET-1 expression in the tumor microenvironment and melanoma progression is demonstrated herein. It is likely that, in vivo, melanoma cells are initially stimulated in a paracrine manner with macrophage-derived ET-1, which would elicit proinvasive responses that ET-1 stimulation exerts on melanoma cells. These responses include the downregulation of E-cadherin[21], the upregulation of melanoma cell adhesion molecule, CXCL1, and CXCL8[21], the activation of matrix metalloproteinases, the activation of the SNAIL gene[21], and the inhibition of apoptosis[21]. Our findings further demonstrate that a high percentage of invasive and metastatic melanoma cells express ET-1 and, as such, are likely stimulated by ET-1 in an autocrine rather than a paracrine manner. A previous study has also demonstrated endothelin expression by invasive melanomas, but this study focused on ET-3 expression in melanoma cells and did not investigate ET-1 expression in the tumor microenvironment[15]. We hypothesize that ET-1 expression by macrophages in the tumor microenvironment occurs by way of an aberrant cytokine network initiated by both melanoma cells and nevus cells. Melanoma cells secrete tumor necrosis factor α (TNFα), which is known to induce ET-1 secretion in macrophages[22,23]. Nevus cells also secrete TNFα but at lower levels than that observed in melanoma cells[22]. These differential levels of TNFα expression could explain the more robust ET-1 expression observed in the dermal infiltrates associated with invasive melanomas as compared with the infiltrates associated with melanocytic nevi. We further hypothesize that ET-1 expression in the dermal microenvironment likely plays a critical role in the progression of melanoma from the in-situ to the invasive stage. ET-1 is a chemotactic and promigratory factor for melanoma cells and melanocytes[18,25] Expression of ET-1 by macrophages in the dermis underlying melanoma in situ lesions may elicit a migration of epidermal melanoma cells into the underlying dermis. Although ET-1 expression by the dermal infiltrate may be sufficient for a localized melanoma invasion, it is likely insufficient for metastasis to distant sites. We hypothesize that the acquisition of endogenous ET-1 expression by melanoma cells may allow them to escape the dermis and metastasize to distant sites, consistent with studies showing significant elevations in plasma levels of ET-1 in patients with metastatic melanoma[26]. As such, ET-1 may serve as an autocrine growth factor in melanoma, as it does in a variety of other cancers including ovarian, prostate, and colon cancer[27,28].

The data also demonstrates that ET-1 plays an etiologic role in the formation of blue nevi. As ET-1 exerts a chemotactic effect on melanocytes, localized concentrations of ET-1-secreting macrophages may serve to sequester melanocytes in the dermis, leading to the development of blue nevi. Because ET-1 is also a potent stimulator of melanogenesis, this would explain the prominent deposition of pigment in blue nevi, as well as in many invasive and metastatic melanomas[29]. The robust ET-1 expression by infiltrating macrophages and melanophages in blue nevi suggests that, although ET-1 expression in the dermal microenvironment alone may be sufficient to induce an invasive phenotype, it is not sufficient to induce a malignant phenotype in melanocytes. However, because of the striking number of ET-1-positive macrophages in these lesions, we speculate that ET-1 plays an important role in the formation of blue nevi and helps maintain the dermal localization of these lesions.

It is interesting to note that, although melanocytes in blue nevi rarely express bRAF in its constitutively active form, 80% of melanocytes in melanocytic nevi express a constitutively activated bRAF kinase[30,31] As shown in our study, the microenvironment of melanocytic nevi rarely demonstrates ET-1 expression. In light of these observations, it is suggested that exposure of normal melanocytes that do not express constitutively active bRAF to ET-1 may cause dermal localization without malignant transformation, as seen in a blue nevus. However, melanocytes expressing constitutively active bRAF and/or mutation of the p16 melanoma susceptibility gene are likely to progress to an invasive malignant phenotype if additionally exposed to ET-1 in the microenvironment. Those invasive melanoma cells that also acquire endogenous expression of either ET-1 or ET-3 would then display a metastatic phenotype. Upregulation of the ETB receptor observed in melanoma cells is almost certainly a prerequisite for melanoma progression, irrespective of the bRAF phenotype[32,33] The rapid development of drug resistance observed in melanoma cells in response to treatment with bRAF inhibitors occurs as a result of upregulation of ETB receptors[21].

The data demonstrates that ET-1 expression in the dermal microenvironment is strongly correlated with melanoma invasion. However, there were rare melanocytic nevi and melanoma in situ lesions in which the associated infiltrate was ET-1 positive. As the incidence of ET-1 expression in the dermal microenvironment increases with the extent of melanoma progression, it is possible that the presence of dermal ET-1 is a marker indicating a greater likelihood for nevi and melanoma in situ lesions to progress to more advanced lesions. Consistent with this possibility, the presence of ET-1-positive melanoma cells in locally invasive melanomas exhibit a greater chance of progression to metastasis. Overall, these new findings implicate the endothelin pathway as a novel target for the treatment or prevention of melanoma invasion and metastasis.

Adult mice have weights in a range from about 10 g to about 32 g (e.g., about 15 g to about 27 g).

Dosage Regimen.

Based on the present description, the provided exemplary dosage ranges included throughout the description can be combined to maximize or optimize the synergistic effect observed, as discussed above, when co-administered using routine methodologies.

The treatment regimen includes a dosage formulation or composition with about 100 µg to about 4000 µg of each included active ingredient (i.e., at least one of the ETBR antagonist, the ETAR antagonist, the anti-PD1 antibody, the bRAF inhibitor, the niacinamide, or the caspase-8 inhibitor). The dosage can be a sustained release dosage in which about 50 µg to about 3000 µg of each of the active ingredients is an initial burst, while about 50 µg to about 3000 µg of the each of the active ingredients is a sustained release over 2 hours.

For example, each of the active ingredient of a formulation or composition of the present disclosure can be present in any of the dosage formulation (e.g., initial burst, sustained release dosage, etc.) in about 100 µg to about 4000 µg, about 100 µg to about 3750 µg, about 100 µg to about 3500 µg, about 100 µg to about 3250 µg, about 100 µg to about 3000 µg, about 100 µg to about 2750 µg, about 100 µg to about 2500 µg, about 100 µg to about 2250 µg, about 100 µg to about 2000 µg, about 100 µg to about 1750 µg, about 100 µg to about 1500 µg, about 100 µg to about 1250 µg, about 100 µg to about 1000 µg, about 100 µg to about 750 µg, about 100 µg to about 500 µg, about 250 µg to about 4000 µg, about 250 µg to about 3750 µg, about 250 µg to about 3500 µg, about 250 µg to about 3250 µg, about 250 µg to about 3000 µg, about 250 µg to about 2750 µg, about 250 µg to about 2500 µg, about 250 µg to about 2250 µg, about 250 µg to about 2000 µg, about 250 µg to about 1750 µg, about 250 µg to about 1500 µg, about 250 µg to about 1250 µg, about 250 µg to about 1000 µg, about 250 µg to about 750 µg, about 250 µg to about 500 µg, about 500 µg to about 4000µ, about 500 µg to about 3750 µg, about 500 µg to about 3500

μg, about 500 μg to about 3250 μg, about 500 μg to about 3000 μg, about 500 μg to about 2750 μg, about 500 μg to about 2500 μg, about 500 μg to about 2250 μg, about 500 μg to about 2000 μg, about 500 μg to about 1750 μg, about 500 μg to about 1500 μg, about 500 μg to about 1250 μg, about 500 μg to about 1000 μg, about 500 μg to about 750 μg, about 750 μg to about 4000 μg, about 750 μg to about 3750 μg, about 750 μg to about 3500 μg, about 750 μg to about 3250 μg, about 750 μg to about 3000 μg, about 750 μg to about 2750 μg, about 750 μg to about 2500 μg, about 750 μg to about 2250 μg, about 750 μg to about 2000 μg, about 750 μg to about 1750 μg, about 750 μg to about 1500 μg, about 750 μg to about 1250 μg, about 750 μg to about 1000 μg, about 1000 μg to about 4000 μg, about 1000 μg to about 3750 μg, about 1000 μg to about 3500 μg, about 1000 μg to about 3250 μg, about 1000 μg to about 3000 μg, about 1000 μg to about 2750 μg, about 1000 μg to about 2500 μg, about 1000 μg to about 2250 μg, about 1000 μg to about 2000 μg, about 1000 μg to about 1750 μg, about 1000 μg to about 1500 μg, about 1000 μg to about 1250 μg, about 1250 μg to about 4000 μg, about 1250 μg to about 3750 μg, about 1250 μg to about 3500 μg, about 1250 μg to about 3250 μg, about 1250 μg to about 3000 μg, about 1250 μg to about 2750 μg, about 1250 μg to about 2500 μg, about 1250 μg to about 2250 μg, about 1250 μg to about 2000 μg, about 1250 μg to about 1750 μg, about 1250 μg to about 1500 μg, about 1500 μg to about 4000 μg, about 1500 μg to about 3750 μg, about 1500 μg to about 3500 μg, about 1500 μg to about 3250 μg, about 1500 μg to about 3000 μg, about 1500 μg to about 2750 μg, about 1500 μg to about 2500 μg, about 1500 μg to about 2250 μg, about 1500 μg to about 2000 μg, about 1500 μg to about 1750 μg, about 1750 μg to about 4000 μg, about 1750 μg to about 3750 μg, about 1750 μg to about 3500 μg, about 1750 μg to about 3250 μg, about 1750 μg to about 3000 μg, about 1750 μg to about 2750 μg, about 1750 μg to about 2500 μg, about 1750 μg to about 2250 μg, about 1750 μg to about 2000 μg, about 2000 μg to about 4000 μg, about 2000 μg to about 3750 μg, about 2000 μg to about 3500 μg, about 2000 μg to about 3250 μg, about 2000 μg to about 3000 μg, about 2000 μg to about 2750 μg, about 2000 μg to about 2500 μg, about 2000 μg to about 2250 μg, about 2250 μg to about 4000 μg, about 2250 μg to about 3750 μg, about 2250 μg to about 3500 μg, about 2250 μg to about 3250 μg, about 2250 μg to about 3000 μg, about 2250 μg to about 2750 μg, about 2250 μg to about 2500 μg, about 2500 μg to about 4000 μg, about 2500 μg to about 3750 μg, about 2500 μg to about 3500 μg, about 2500 μg to about 3250 μg, about 2500 μg to about 3000 μg, about 2500 μg to about 2750 μg, about 2750 μg to about 4000 μg, about 2750 μg to about 3750 μg, about 2750 μg to about 3500 μg, about 2750 μg to about 3250 μg, about 2750 μg to about 3000 μg, about 3000 μg to about 4000 μg, about 3000 μg to about 3750 μg, about 3000 μg to about 3500 μg, about 3000 μg to about 3250 μg, about 3250 μg to about 4000 μg, about 3250 μg to about 3750 μg, about 3250 μg to about 3500 μg, about 3500 μg to about 4000 μg, about 3500 μg to about 3750 μg, or about 3750 μg to about 4000 μg.

Each active ingredient of a formulation/composition of the present disclosure can be present in about 0.1 mg/mL to about 5.0 mg/mL of the dosage formulation or composition (e.g., about 0.1 mg/mL to about 4.5 mg/mL, about 0.1 mg/mL to about 4.0 mg/mL, about 0.1 mg/mL to about 3.5 mg/mL, about 0.1 mg/mL to about 3.0 mg/mL, about 0.1 mg/mL to about 2.5 mg/mL, about 0.1 mg/mL to about 2.0 mg/mL, about 0.1 mg/mL to about 1.5 mg/mL, about 0.1 mg/mL to about 1.0 mg/mL, about 0.1 mg/mL to about 0.5 mg/mL, about 0.5 mg/mL to about 4.5 mg/mL, about 0.5 mg/mL to about 4.0 mg/mL, about 0.5 mg/mL to about 3.5 mg/mL, about 0.5 mg/mL to about 3.0 mg/mL, about 0.5 mg/mL to about 2.5 mg/mL, about 0.5 mg/mL to about 2.0 mg/mL, about 0.5 mg/mL to about 1.5 mg/mL, about 0.5 mg/mL to about 1.0 mg/mL, about 1.0 mg/mL to about 4.5 mg/mL, about 1.0 mg/mL to about 4.0 mg/mL, about 1.0 mg/mL to about 3.5 mg/mL, about 1.0 mg/mL to about 3.0 mg/mL, about 1.0 mg/mL to about 2.5 mg/mL, about 1.0 mg/mL to about 2.0 mg/mL, about 1.0 mg/mL to about 1.5 mg/mL, about 1.5 mg/mL to about 4.5 mg/mL, about 1.5 mg/mL to about 4.0 mg/mL, about 1.5 mg/mL to about 3.5 mg/mL, about 1.5 mg/mL to about 3.0 mg/mL, about 1.5 mg/mL to about 2.5 mg/mL, about 1.5 mg/mL to about 2.0 mg/mL, about 2.0 mg/mL to about 4.5 mg/mL, about 2.0 mg/mL to about 4.0 mg/mL, about 2.0 mg/mL to about 3.5 mg/mL, about 2.0 mg/mL to about 3.0 mg/mL, about 2.0 mg/mL to about 2.5 mg/mL, about 2.5 mg/mL to about 4.5 mg/mL, about 2.5 mg/mL to about 4.0 mg/mL, about 2.5 mg/mL to about 3.5 mg/mL, about 2.5 mg/mL to about 3.0 mg/mL, about 3.0 mg/mL to about 4.5 mg/mL, about 3.0 mg/mL to about 4.0 mg/mL, about 3.0 mg/mL to about 3.5 mg/mL, about 3.5 mg/mL to about 4.5 mg/mL, about 3.5 mg/mL to about 4.0 mg/mL, or about 3.5 mg/mL to about 4.5 mg/mL relative to the formulation/composition).

The dosage formulation or compositions of the present disclosure can be administered orally, sublingually, parenterally, intranasally, intravenously, intradermally, subcutaneously, or topically.

Exemplary Formulations of the Disclosure

Any of the aspects or embodiments described herein can be a single-component oil phase formulation/composition, as described above, wherein each active ingredient can be at any of the dosages or concentrations described above. The single-component oil phase can be a fixed oil, such as soybean oil. For example, the formulation or composition can comprise about 0.1 mg to about 5.0 mg of each active ingredient in 1 mL of the single-component oil (i.e., about 0.5 mg/mL, about 1 mg/mL, or about 1.5 mg/mL of each active ingredient in the single-component oil). The single-component oil phase formulation/composition can be prepared by adding each active ingredient (e.g., about 1 mg to about 50 mg of each of the active ingredient(s)) to about 10 mL of the single-component oil solution.

Any of the aspects or embodiments described herein can be a DMSO formulation/composition, as described above, wherein the active ingredient or ingredients can be at any of the dosages or concentrations described above. The formulation/composition can include a DMSO solution that is about 5% to about 100% DMSO (e.g., about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 30% to about 95%, about 45% to about 95%, about 75% to about 95%, about 30% to about 90%, about 45% to about 90%, about 75% to about 90%, about 30% to about 85%, about 45% to about 85%, or about 75% to about 85%). For example, the formulation or composition can comprise about 0.1 mg to about 5.0 mg of each active ingredient in 1 mL of DMSO (i.e., about 0.5 mg/mL, about 1 mg/mL, or about 1.5 mg/mL of each active ingredient in DMSO). The DMSO formulation/composition can be prepared by adding each active ingredient (e.g., about 1 mg to about 50 mg of each of the active ingredient(s)) to about 10 mL of the DMSO solution.

Any of the aspects or embodiments described herein can be a LyoCell® formulation/composition, as described above, wherein the active ingredient can be at any of the dosages or concentrations described above. For example, the formulation or composition can comprise about 0.1 mg to about 5.0 mg of each active ingredient in 1 mL of LyoCell® (i.e., about 0.5 mg/mL, about 1 mg/mL, or about 1.5 mg/mL of each active ingredient in LyoCell®). The LyoCell® formulation/composition can be prepared by adding about 1 mg to about 50 mg of the active ingredient(s) to about 10 mL of LyoCell®. LyoCell® can be prepared in accordance to U.S. Pat. No. 7,713,440 or purchased commercially from Particle Sciences® (Bethlehem, Pa. 18017-8920).

Any of the aspects or embodiments described herein can include nanoparticles, as described above, wherein each active ingredient can be at any of the dosages or concentrations described above. For example, the formulation or composition can comprise about 0.1 mg to about 5.0 mg of the active ingredient(s) in about a 1 mL nanoparticle suspension (e.g., a solid lipid nanoparticle suspension). As such, the nanoparticle formulation comprises, e.g., about 0.5 mg/mL, about 1.0 mg/mL, or about 1.5 mg/mL of each active ingredient in a nanoparticle suspension. The nanoparticles formulation/composition can be prepared by adding about 1 mg to about 50 mg of each active ingredient to 240 mg of lipid phase, and emulsifying in 9.75 mL aqueous phase, thereby forming a solid lipid nanoparticles suspension in an about 10 mL total batch (about 2.5% solids). The nanoparticle formulations/compositions can comprise about 2% to about 8% carnauba (e.g., 5.0%), about 0.5% to about 3.5% soybean oil (e.g., about 2.0%), about 85.0% to about 97.0% aqueous solution (e.g., about 92.0%, about 0.5% to about 1.5% polysorbate (e.g., about 1.0%), and the active ingredient(s) in about 0.1 mg/mL to about 5.0 mg/mL (e.g., about 0.1 mg/mL to about 5.0 mg/mL).

Specific Embodiments

In an aspect, a therapeutic composition is provided. The comprises: an effective amount of at least one of an ETBR antagonist, a caspase-8 inhibitor or a combination thereof; a synergistically effective amount of at least one of an ETAR antagonist, an anti-PD1 antibody, a bRAF inhibitor, niacinamide or a combination thereof; and a pharmaceutically acceptable carrier.

In any of the embodiments or aspects described herein, at least one of: (1) the anti-PD1 antibody is at least one agent selected from the group consisting of Nivolumab, pembrolizumab, pidilizumab, or any other anti-PD1 antibody known or that becomes known to one skilled in the art; (2) the bRAF inhibitor is at least one agent selected from the group consisting of Dabrafenib, Sorafenib, Vemurafenib, or any other bRAF inhibitor known or that becomes known to one skilled in the art; (3) the ETBR antagonist is at least one of BQ788, BQ-017, A192621, a deuterated or fluorinated analog thereof, or a combination thereof; (4) the ETAR antagonist is BQ123; or (5) the caspase-8 inhibitor is a peptide with a sequence of Ac-AAVALLPAVLLAALAPIETD-CHO (SEQ ID NO:1).

In any of the embodiments or aspects described herein, (1) the anti-PD1 antibody is at least one agent selected from the group consisting of Nivolumab, pembrolizumab, pidilizumab, or any other anti-PD1 antibody known or that becomes known to one skilled in the art; or (2) the bRAF inhibitor is at least one agent selected from the group consisting of Dabrafenib, Sorafenib, Vemurafenib, or any other bRAF inhibitor known or that becomes known to one skilled in the art; or (3) the ETBR antagonist is at least one of BQ788, BQ-017, A192621, a deuterated or fluorinated analog thereof, or a combination thereof; or (4) the ETAR antagonist is BQ123; or (5) the caspase-8 inhibitor is a peptide with a sequence of Ac-AAVALLPAVLLAALAPIETD-CHO (SEQ ID NO:1).

In any of the embodiments or aspects described herein, (1) the anti-PD1 antibody is at least one agent selected from the group consisting of Nivolumab, pembrolizumab, pidilizumab, or any other anti-PD1 antibody known or that becomes known to one skilled in the art; and/or (2) the bRAF inhibitor is at least one agent selected from the group consisting of Dabrafenib, Sorafenib, Vemurafenib, or any other bRAF inhibitor known or that becomes known to one skilled in the art; and/or (3) the ETBR antagonist is at least one of BQ788, BQ-017, A192621, a deuterated or fluorinated analog thereof, or a combination thereof; and/or (4) the ETAR antagonist is BQ123; and/or (5) the caspase-8 inhibitor is a peptide with a sequence of Ac-AAVALLPAVLLAALAPIETD-CHO (SEQ ID NO:1).

In any of the embodiments or aspects described herein, the anti-PD1 antibody is at least one agent selected from the group consisting of Nivolumab, pembrolizumab, pidilizumab, and a combination thereof.

In any of the embodiments or aspects described herein, the bRAF inhibitor is at least one agent selected from the group consisting of Dabrafenib, Sorafenib, Vemurafenib, and a combination thereof.

In any of the embodiments or aspects described herein, the ETBR antagonist is at least one of BQ788, BQ-017, A192621, a deuterated or fluorinated analog thereof, or a combination thereof.

In any of the embodiments or aspects described herein, the ETAR antagonist is BQ123.

In any of the embodiments or aspects described herein, the caspase-8 inhibitor is a peptide with a sequence of Ac-AAVALLPAVLLAALAPIETD-CHO (SEQ ID NO:1).

In any of the embodiments or aspects described herein, a dosage of at least one of the ETBR antagonist, the ETAR antagonist, the anti-PD1 antibody, the bRAF inhibitor, the niacinamide, and the caspase-8 inhibitor is about 100 µg to about 4000 µg and/or a concentration of at least one of the ETBR antagonist, the ETAR antagonist, the anti-PD1 antibody, the bRAF inhibitor, the niacinamide, and the caspase-8 inhibitor is about 0.1 to about 5.0 µg/mL of the composition.

In any of the embodiments or aspects described herein, a dosage of at least one of the ETBR antagonist, the ETAR antagonist, the anti-PD1 antibody, the bRAF inhibitor, the niacinamide, and the caspase-8 inhibitor is about 0.1 µg to about 5000 µg.

In any of the embodiments or aspects described herein, a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the embodiments or aspects described herein, the composition further comprising at least one excipient selected from the group consisting of LyoCell®, soybean oil, dimethyl sulfoxide (DMSO), Intravail®, Protek®, and Aegis Hydrogel™

In any of the embodiments or aspects described herein, the DMSO is an about 5% to about 100% DMSO solution.

In any of the embodiments or aspects described herein, the pharmaceutically acceptable carrier is selected from the group consisting of a solid lipid nanoparticle, a liposome, and a biocompatible polymer.

In another aspect, a controlled release subcutaneous or intramuscular dosage formulation is provided. The formulations comprises a uniform dispersion of active ingredients including: an ETBR antagonist or a caspase-8 inhibitor or a combination thereof; and a synergistic amount of at least one additional agent selected from the group consisting of an ETAR antagonist, an anti-PD1 antibody, a bRAF inhibitor, niacinamide or a combination thereof in a biocompatible delivery system, wherein following administration the ETBR antagonist and additional agent are released slowly and simultaneously from the formulation into the systemic circulation.

In any of the embodiments or aspects described herein, wherein at least one of: (1) the anti-PD1 antibody is at least one agent selected from the group consisting of Nivolumab, pembrolizumab, pidilizumab, or any other anti-PD1 antibody known or that becomes known to one skilled in the art; (2) the bRAF inhibitor is at least one agent selected from the group consisting of Dabrafenib, Sorafenib, Vemurafenib, or any other bRAF inhibitor known or that becomes known to one skilled in the art; (3) the ETBR antagonist is at least one of BQ788, BQ-017, A192621, a deuterated or fluorinated analog thereof, or a combination thereof; (4) the ETAR antagonist is BQ123; or (5) the caspase-8 inhibitor is a peptide with a sequence of Ac-AAVALLPAVLLAALAPIETD-CHO £SEQ ID NO:1).

In any of the embodiments or aspects described herein, at least one of: (1) the anti-PD1 antibody is at least one agent selected from the group consisting of Nivolumab, pembrolizumab, pidilizumab, or any other anti-PD1 antibody known or that becomes known to one skilled in the art; or (2) the bRAF inhibitor is at least one agent selected from the group consisting of Dabrafenib, Sorafenib, Vemurafenib, or any other bRAF inhibitor known or that becomes known to one skilled in the art; or (3) the ETBR antagonist is at least one of BQ788, BQ-017, A192621, a deuterated or fluorinated analog thereof, or a combination thereof; or (4) the ETAR antagonist is BQ123; or (5) the caspase-8 inhibitor is a peptide with a sequence of Ac-AAVALLPAVLLAALAPI-ETD-CHO (SEQ ID NO:1).

In any of the embodiments or aspects described herein, (1) the anti-PD1 antibody is at least one agent selected from the group consisting of Nivolumab, pembrolizumab, pidilizumab, or any other anti-PD1 antibody known or that becomes known to one skilled in the art; or (2) the bRAF inhibitor is at least one agent selected from the group consisting of Dabrafenib, Sorafenib, Vemurafenib, or any other bRAF inhibitor known or that becomes known to one skilled in the art; or (3) the ETBR antagonist is at least one of BQ788, BQ-017, A192621, a deuterated or fluorinated analog thereof, or a combination thereof; or (4) the ETAR antagonist is BQ123; or (5) the caspase-8 inhibitor is a peptide with a sequence of Ac-AAVALLPAVLLAALAPI-ETD-CHO (SEQ ID NO:1).

In any of the embodiments or aspects described herein, (1) the anti-PD1 antibody is at least one agent selected from the group consisting of Nivolumab, pembrolizumab, pidilizumab, or any other anti-PD1 antibody known or that becomes known to one skilled in the art; and/or (2) the bRAF inhibitor is at least one agent selected from the group consisting of Dabrafenib, Sorafenib, Vemurafenib, or any other bRAF inhibitor known or that becomes known to one skilled in the art; and/or (3) the ETBR antagonist is at least one of BQ788, BQ-017, A192621, a deuterated or fluorinated analog thereof, or a combination thereof; and/or (4) the ETAR antagonist is BQ123; and/or (5) the caspase-8 inhibitor is a peptide with a sequence of Ac-AAVALLPAV-LLAALAPIETD-CHO (SEQ ID NO:1).

In any of the embodiments or aspects described herein, the anti-PD1 antibody is at least one agent selected from the group consisting of Nivolumab, pembrolizumab, pidilizumab, and a combination thereof.

In any of the embodiments or aspects described herein, the bRAF inhibitor is at least one agent selected from the group consisting of Dabrafenib, Sorafenib, Vemurafenib, and a combination thereof.

In any of the embodiments or aspects described herein, the ETBR antagonist is at least one of BQ788, A192621 or a combination thereof.

In any of the embodiments or aspects described herein, the ETAR antagonist is BQ123.

In any of the embodiments or aspects described herein, the caspase-8 inhibitor is a peptide with a sequence of Ac-AAVALLPAVLLAALAPIETD-CHO (SEQ ID NO:1).

In any of the embodiments or aspects described herein, the delivery system is selected from the groups consisting of: (1) a biocompatible polymer is selected from the group consisting of poly(lactides), poly(glycolides), poly(lactide-co-glycolides), poly(lactic acid)s, poly(glycolic acid)s, poly (lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof; (2) a liposome preparation selected from the group consisting of phosphatidylethanolamines (PE) such as dipalmitoyl PE (DPPE), and partially unsaturated phosphatidylcholine (PC), such as egg PC (EPC) or SPC, Fully unsaturated PC such as HSPC, PG, phosphatidylserine (PS) and phosphatidylinositol (PI), a partially unsaturated PG, Dipalmitoylphosphatidylglycerol (DPPG), cholesterol, DSPE-PEG2000; (3) a DMSO solution; (4) LyoCell®; and (5) a solid lipid nanoparticle preparation selected from the group consisting of triglycerides (Compritol 888 ATO and Dynasan 112), carnauba wax, beeswax, cetyl alcohol, emulsifying wax, cholesterol, cholesterol butyrate and poly(ethylene)glycol (PEG) derivatives.

In any of the embodiments or aspects described herein, the delivery system is selected from the groups consisting of: (1) a biocompatible polymer; (2) a liposome preparation; (3) a DMSO solution; (4) LyoCell®; and (5) a solid lipid nanoparticle preparation.

In any of the embodiments or aspects described herein, the biocompatible polymer is selected from the group consisting of poly(lactides), poly(glycolides), poly(lactide-co-glycolides), poly(lactic acid)s, poly(glycolic acid)s, poly (lactic acid-co-glycolic acid)s, polycaprolactone, polycarbonates, polyesteramides, polyanhydrides, poly (amino acids), polyorthoesters, polycyanoacrylates, poly(p-dioxanone), poly(alkylene oxalate)s, biodegradable polyurethanes, blends and copolymers thereof.

In any of the embodiments or aspects described herein, the liposome preparation is selected from the group consisting of phosphatidylethanolamines (PE) such as dipalmitoyl PE (DPPE), and partially unsaturated phosphatidylcholine (PC), such as egg PC (EPC) or SPC, Fully unsaturated PC such as HSPC, PG, phosphatidylserine (PS) and phosphatidylinositol (PI), a partially unsaturated PG, Dipalmitoylphosphatidylglycerol (DPPG), cholesterol, DSPE-PEG2000

In any of the embodiments or aspects described herein, the solid lipid nanoparticle preparation is selected from the group consisting of triglycerides (Compritol 888 ATO and Dynasan 112), carnauba wax, beeswax, cetyl alcohol, emulsifying wax, cholesterol, cholesterol butyrate and poly(ethylene)glycol (PEG) derivatives In any of the embodiments or aspects described herein, the DMSO solution is about 5% to about 100% DMSO.

In any of the embodiments or aspects described herein, a dosage of at least one of the ETBR antagonist, the ETAR antagonist, the anti-PD1 antibody, the bRAF inhibitor, the niacinamide, and the caspase-8 inhibitor is about 0.1 µg to about 5000 µg and/or a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the embodiments or aspects described herein, a dosage of at least one of the ETBR antagonist, the ETAR antagonist, the anti-PD1 antibody, the bRAF inhibitor, the niacinamide, and the caspase-8 inhibitor is about 0.1 µg to about 5000 µg.

In any of the embodiments or aspects described herein, a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the embodiments or aspects described herein, a dosage of at least one of the ETBR antagonist, the ETAR antagonist, the anti-PD1 antibody, the bRAF inhibitor, the niacinamide, or the caspase-8 inhibitor is from about 100 µg to about 4000 µg and/or a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the embodiments or aspects described herein, a dosage of at least one of the ETBR antagonist, the ETAR antagonist, the anti-PD1 antibody, the bRAF inhibitor, the niacinamide, or the caspase-8 inhibitor is from about 100 µg to about 4000 µg.

In any of the embodiments or aspects described herein, a concentration of at least one of the ETBR antagonist, the ETAR antagonist, the anti-PD1 antibody, the bRAF inhibitor, the niacinamide, and the caspase-8 inhibitor is about 0.01 µg/mL to about 1000 mg/mL of the composition.

In any of the embodiments or aspects described herein, the formulation further comprising an excipient selected from the group consisting of Intravail®, Protek®, and Aegis Hydrogel™

In an additional aspect, a method for treating cancer in a patient is provided. The method comprises administering to a patient in need thereof the composition of the present disclosure.

In any of the embodiments or aspects described herein, the composition or formulation is delivered intranasally or intravenously or intracranially.

In a further aspect, a method for treating cancer in a patient comprising administering to a patient in need thereof the formulation of the present disclosure.

In any of the embodiments or aspects described herein, the composition or formulation is delivered intranasally or intravenously or intracranially.

In yet another aspect, a method of determining sensitivity of cancer cells to an endothelin receptor antagonist is provided. The method comprises: a) providing a cancer tissue sample from a patient; b) incubating the tissue sample in the presence of an antibody that binds specifically to ET-1 and/or an antibody that binds specifically to ET-3; and c) detecting the amount of antibody bound to ET-1 and/or ET-3, wherein when ET-1 and/or ET-3 are actively expressed in the cancer, the cancer will be sensitive to an endothelin receptor antagonist therapy.

In any of the embodiments or aspects described herein, detecting the amount of antibody bound to ET-1 and/or ET-3 is performed with a secondary antibody conjugated to a detectable label.

In any of the embodiments or aspects described herein, following c) detecting, the method further comprises d) administering an effective amount of at least one of an endothelin receptor antagonist or an inhibitor of ETBR signaling (such as a caspase-8 inhibitor).

In any of the embodiments or aspects described herein, the endothelin receptor antagonist is a selective ETBR antagonist and/or a selective ETAR antagonist.

In any of the embodiments or aspects described herein, the endothelin receptor antagonist is BQ788, BQ-017, a deuterated or fluorinated analog of BQ788, a deuterated or fluorinated analog of BQ-017, and/or BQ123.

In a further aspect, a method of determining sensitivity of cancer cells to an endothelin receptor antagonist is provided. The method comprising: a) providing a tissue sample from cancer cells from a patient that has a cancer; b) fixing the sample in formalin, c) embedding in paraffin, d) cutting sections with a microtome and transferring sections to glass slides suitable for immunohistochemistry; e) incubating the slides in the presence of an antibody that detects the presence of ET-1 and/or an antibody that detects the presence of ET-3, at least one additional secondary antibody which binds to the antibody that binds to ET-1 and/or ET-3 and is conjugated to a molecule that allows for visualization of the bound antibody complex, thereby determining that ET-1 and/or ET-3 are actively expressed in the tumor and thus indicating that inhibition of ET-1 and/or ET-3 binding to an endothelin receptor will exert a therapeutic effect.

In any of the embodiments or aspects described herein, the endothelin receptor antagonist is a selective ETBR antagonist and/or a selective ETAR antagonist.

In any of the embodiments or aspects described herein, the endothelin receptor antagonist is BQ788, BQ-017, a deuterated or fluorinated analog of BQ788, a deuterated or fluorinated analog of BQ-017, and/or BQ123.

In an aspect, a method for treating ETBR-related metastatic brain cancer is provided. The method comprises administering an effective amount to a subject in need thereof the composition of claim 1, wherein the composition is effective for treating or ameliorating a symptom of ETBR-related metastatic brain cancer.

In any of the embodiments or aspects described herein, the ETBR-related metastatic brain cancer is metastatic melanoma-related brain cancer, metastatic squamous cell carcinoma-related brain cancer, glioblastoma or a combination thereof.

In any of the embodiments or aspects described herein, the composition or formulation is administered intranasally or sublingually.

In an additional aspect, a method for treating ETBR-related metastatic brain cancer is provided. The method comprises administering an effective amount to a subject in need thereof of the formulation of the present disclosure, wherein the formulation is effective for treating or ameliorating a symptom of ETBR-related metastatic brain cancer.

In an additional aspect, a method of determining sensitivity of cancer cells to an immune based therapy is provided. The method comprises: a) providing a tissue sample from cancer cells from a patient that has a cancer; b) incubating the tissue sample in the presence of an antibody that binds ET-1 and/or an antibody that binds ET-3; and c)

detecting the amount of antibody bound to ET-1 and/or ET-3, wherein when ET-1 and/or ET-3 are actively expressed in the tumor and thus indicating that the cancer will not be responsive to the immune based therapy.

In any of the embodiments or aspects described herein, detecting the amount of antibody bound to ET-1 and/or ET-3 is performed with at least one secondary antibody conjugated to a detectable label.

In any of the embodiments or aspects described herein, following c) detecting, the method further comprises d) administering an effective amount of an endothelin receptor antagonist.

In any of the embodiments or aspects described herein, the immune based therapy is selected from the group consisting of an immune checkpoint inhibitor, a cancer vaccine, and a Chimeric Antigen Receptor T-Cell (CAR-T) therapy.

In any of the embodiments or aspects described herein, the immune checkpoint inhibitor is an anti-PD-1 antibody.

In yet a further aspect, a method of determining sensitivity of cancer cells to an immune based therapy is provided. The method comprises: a) providing a tissue sample from cancer cells from a patient that has a cancer; b) fixing the sample in formalin, c) embedding in paraffin, d) cutting sections with a microtome and transferring sections to glass slides suitable for immunohistochemistry; e) incubating the slides in the presence of an antibody that detects the presence of ET-1 and/or an antibody that detects the presence of ET-3, at least one additional secondary antibody which binds to the antibody that binds to ET-1 and/or ET-3 and is conjugated to a molecule that allows for visualization of the bound antibody complex, thereby determining that ET-1 and/or ET-3 are actively expressed in the tumor and thus indicating that the cancer will not be responsive to the immune based therapy.

In any of the embodiments or aspects described herein, the immune based therapy is selected from the group consisting of an immune checkpoint inhibitor, a cancer vaccine, and a Chimeric Antigen Receptor T-Cell (CAR-T) therapy.

In any of the embodiments or aspects described herein, the immune checkpoint inhibitor is an anti-PD-1 antibody.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

REFERENCES

The following references are incorporated herein by reference in their entirety for all purposes.

1. American Cancer Society. Cancer Facts & Figures 2015. Atlanta: American Cancer Society; 2015.
2. How Significant Can Keytruda Be For Merck? Forbes, 10/14, http://www.forbes.com/sites/greatspeculations/2014/10/03/how-significant-can-keytruda-be-for-merck/
3. Howlader N, Noone A M, Krapcho M, Garshell J, Miller D, Altekruse S F, Kosary C L, Yu M, Ruhl J, Tatalovich Z, Mariotto A, Lewis D R, Chen H S, Feuer E J, Cronin K A (eds). SEER Cancer Statistics Review, 1975-2012, National Cancer Institute. Bethesda, Md., http://seer.cancer.gov/csr/1975 2012/(http://seer.cancer.gov/csr/)
4. Asundi, J. et al MAPK pathway inhibition enhances the efficacy of an anti-endothelin B receptor drug conjugate by inducing target expression in melanoma. Mol Cancer Ther 2014: 13 (6): 1599-610 (http://mct.aacrjournals.org/content/13/6/1599.full.pdf+html)
5. Sosman J., Immunotherapy of advanced melanoma with immune checkpoint inhibition, Up To Date literature review (http://www.uptodate.com/contents/immunotherapy-of-advanced-melanoma-with-immune-checkpoint-inhibition).
6. Sosman, J. Molecularly targeted therapy for metastatic melanoma, Up to Date Literature review (http://www.uptodate.com/contents/molecularly-targeted-therapy-for-metastatic-melanoma)
7. Sampson J H, Carter J H Jr, Friedman A H, Seigler H F. Demographics, prognosis, and therapy in 702 patients with brain metastases from malignant melanoma. J Neurosurg 1998; 88:11.
8. Fife K M, Colman M H, Stevens G N, et al. Determinants of outcome in melanoma patients with cerebral metastases. J Clin Oncol 2004; 22:1293.
9. Samlowski, W. et al, Management of brain metastases in melanoma, Up To Date literature review (http://www.uptodate.com/contents/management-of-brain-metastases-in-melanoma)
10. Saldana-Caboverde et al, Pigment Cell and Melanoma Research; 23(2): p160-170, April 2010 http://onlinelibrary.wiley.com/doi/10.1111/j 0.1755-148X.2010.00678.x/full
11. Jamal, S. et al, Journal of clinical investigation. 2002: 110(4):443-452.
12. Mangahas et al, Journal of investigative dermatology. 2004:123(6):1135-1139.
13. Cruz-Munoz, W. et al., Roles for Endothelin Receptor B and BCL2A1 in Spontaneous CNS Metastasis of Melanoma. Cancer Research 2012; 72(19):4909-19.
14. Kamino H, Tam S T. Immunoperoxidase technique modified by counterstain with azure B as a diagnostic aid in evaluating heavily pigmented melanocytic neoplasms. J Cutan Pathol 1991; 18:436-439.
15. Tang L, Su M, Zhang Y, Ip W, Martinka M, Huang C, Zhou Y. Endothelin-3 is produced by metastatic melanoma cells and promotes melanoma cell survival. J Cutan Med Surg 2008; 12:64-70.
16. Jamal S. Endothelin-1 down-regulates E-cadherin in melanocytic cells by apoptosis-independent activation of caspase-8. J Am Acad Dermatol 2000; 43:703-704.
17. Jamal S, Schneider R J. UV-induction of keratinocyte endothelin-1 downregulates E-cadherin in melanocytes and melanoma cells. J Clin Invest 2002; 110:443-452.

18. Mangahas C R, dela Cruz G V, Schneider R J, Jamal S. Endothelin-1 upregulates MCAM in melanocytes. J Invest Dermatol 2004; 123:1135-1139.
19. Mangahas C R, dela Cruz G V, Friedman-Jimenez G, Jamal S. Endothelin-1 induces CXCL1 and CXCL8 secretion in human melanoma cells. J Invest Dermatol 2005; 125:307-311.
20. Bagnato A, Rosana L, Spinella F, Di Castro V, Tecce R, Natali P G. Endothelin B receptor blockade inhibits dynamics of cell interactions and communications in melanoma cell progression. Cancer Res 2004; 64:1436-1443.
21. Asundi J, Lacap J A, Clark S, Nannini M, Roth L, Polakis P. MAPK pathway inhibition enhances the efficacy of an anti-endothelin B receptor drug conjugate by inducing target expression in melanoma. Mol Cancer Ther 2014; 13:1599-1610.
22. Moretti S, Pinzi C, Spallanzani A, Berti E, Chiarugi A, Mazzoli S, et al. Immunohistochemical evidence of cytokine networks during progression of human melanocytic lesions. Int J Cancer 1999; 84:160-168.
23. Ehrenreich H, Rieckmann P, Sinowatz F, Weih K A, Arthur L O, Goebel F D, et al. Potent stimulation of monocytic endothelin-1 production by HIV-1 glycoprotein 120. J Immunol 1993; 150:4601-4609.
24. Chiriboa L, Meehan S, Osman I, Glick M, de al Cruz Gelo, Howell B S, Friedman-Jimenez G, Schneider R J, Jamal S. Endothelin-1 in the tumor microenvironment correlates with melanoma invasion. Melanoma Research 2016; 00(00): 1-9.
25. Yohn J J, Smith C, Stevens T, Hoffman T A, Morelli J G, Hurt D L, et al. Human melanoma cells express functional endothelin-1 receptors. Biochem Biophys Res Commun 1994; 201:449-457
26. Bohm M, Schiller M, Nashan D, Stadler R, Luger T A, Metze D. Diffuse melanosis arising from metastatic melanoma: pathogenetic function of elevated melanocyte peptide growth factors. J Am Acad Dermatol 2001; 44:747-754.
27. Nelson J, Bagnato A, Battistini B, Nisen P. The endothelin axis: emerging role in cancer. Nat Rev Cancer 2003; 3:110-116.
28. Bagnato A, Natali P G. Endothelin receptors as novel targets in tumor therapy. J Transl Med 2004; 2:16.
29. Imokawa G, Kobayashi T, Miyagishi M, Higashi K, Yada Y. The role of endothelin-1 in epidermal hyperpigmentation and signaling mechanisms of mitogenesis and melanogenesis. Pigment Cell Res 1997; 10:218-228.
30. Saldanha G, Purnell D, Fletcher A, Potter L, Gillies A, Pringle J H. High BRAF mutation frequency does not characterize all melanocytic tumor types. Int J Cancer 2004; 111:705-710.
31. Gray-Schopfer V C, da Rocha Dias S, Marais R. The role of B-RAF in melanoma. Cancer Metastasis Rev 2005; 24:165-183.
32. Ross D T, Scherf U, Eisen M B, Perou C M, Rees C, Spellman P, et al. Systematic variation in gene expression patterns in human cancer cell lines. Nat Genet 2000; 24:227-235.
33. Bittner M, Meltzer P, Chen Y, Jiang Y, Seftor E, Hendrix M, et al. Molecular classification of cutaneous malignant melanoma by gene expression profiling. Nature 2000; 406:536-540.
34. Chiriboga et al. Endothelin-1 in the tumor microenvironment correlates with melanoma invasion. Melanoma Res. 2016 June; 26(3):236-44

What is claimed is:

1. A method for treating ETBR-related metastatic brain cancer in a human subject in need thereof, comprising administering to the human subject:
   (a) an endothelin B receptor (ETBR) antagonist, and
   (b) an immune checkpoint inhibitor;
in amounts effective for treating the cancer.

2. The method of claim 1, wherein the ETBR antagonist and the immune checkpoint inhibitor are administered to the human subject at different times.

3. The method of claim 1, further comprising administering a caspase-8 inhibitor.

4. The method of claim 1, wherein the ETBR antagonist is formulated in a pharmaceutically acceptable carrier that comprises dimethyl sulfoxide (DMSO).

5. The method of claim 1, wherein the ETBR-related metastatic brain cancer is metastatic melanoma-related brain cancer, metastatic squamous cell carcinoma-related brain cancer, or any combination thereof.

6. The method of claim 1, wherein the ETBR antagonist is BQ788, A192621, or a combination thereof.

7. The method of claim 1, wherein the ETBR antagonist is BQ788.

8. The method of claim 1, wherein the ETBR antagonist is formulated as nanoparticles.

* * * * *

UNITED STATES PATENT AND TRADEMARK OFFICE
CERTIFICATE OF CORRECTION

| | |
|---|---|
| PATENT NO. | : 10,695,400 B2 |
| APPLICATION NO. | : 15/227792 |
| DATED | : June 30, 2020 |
| INVENTOR(S) | : Sumayah Jamal |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 468 days.

Signed and Sealed this
Thirteenth Day of December, 2022

*Katherine Kelly Vidal*

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylation
<220> FEATURE:
<221> NAME/KEY: MISC_FEATURE
<222> LOCATION: (20)..(20)
<223> OTHER INFORMATION: Carboxylation

<400> SEQUENCE: 1

Ala Ala Val Ala Leu Leu Pro Ala Val Leu Leu Ala Ala Leu Ala Pro
1               5                   10                  15

Ile Glu Thr Asp
            20
```